United States Patent
DiBenedetto et al.

(10) Patent No.: US 8,200,323 B2
(45) Date of Patent: Jun. 12, 2012

(54) PROGRAM PRODUCTS, METHODS, AND SYSTEMS FOR PROVIDING FITNESS MONITORING SERVICES

(75) Inventors: Christian DiBenedetto, North Plains, OR (US); Maya Ann Powch, Portland, OR (US); Stephen John Black, Portland, OR (US)

(73) Assignee: adidas AG, Herzogenaurach (DE)

( * ) Notice: Subject to any disclaimer, the term of this patent is extended or adjusted under 35 U.S.C. 154(b) by 317 days.

(21) Appl. No.: 12/468,025

(22) Filed: May 18, 2009

(65) Prior Publication Data
US 2010/0292600 A1    Nov. 18, 2010

(51) Int. Cl.
*A61B 5/04* (2006.01)
(52) U.S. Cl. ............... 600/519; 600/520; 482/8
(58) Field of Classification Search .......... 600/519–523; 482/1, 8, 9, 901
See application file for complete search history.

(56) References Cited

U.S. PATENT DOCUMENTS

| | | | |
|---|---|---|---|
| 3,742,937 A | 7/1973 | Manuel et al. | |
| 3,802,698 A | 4/1974 | Burian et al. | |
| 3,838,684 A | 10/1974 | Manuel et al. | |
| 3,978,849 A | 9/1976 | Geneen | |
| 4,027,663 A | 6/1977 | Fischler et al. | |
| 4,038,976 A | 8/1977 | Hardy et al. | |
| 4,120,294 A | 10/1978 | Wolfe | |
| 4,120,296 A | 10/1978 | Prinz | |
| 4,221,223 A | 9/1980 | Linden | |
| 4,248,244 A | 2/1981 | Charnitski et al. | |
| 4,252,128 A | 2/1981 | Kane | |
| 4,436,096 A | 3/1984 | Dyck et al. | |
| 4,647,217 A | 3/1987 | Havel | |
| 4,653,498 A | 3/1987 | New, Jr. et al. | |
| 4,776,323 A | 10/1988 | Spector | |
| 4,788,983 A | 12/1988 | Brink et al. | |
| 4,938,228 A | 7/1990 | Righter et al. | |
| 5,314,389 A | 5/1994 | Dotan | |
| 5,735,799 A | 4/1998 | Baba et al. | |
| 5,769,755 A * | 6/1998 | Henry et al. ............ 482/8 |
| 5,857,939 A | 1/1999 | Kaufman | |
| 5,891,042 A | 4/1999 | Sham et al. | |

(Continued)

FOREIGN PATENT DOCUMENTS
WO    WO02067449    8/2002

(Continued)

OTHER PUBLICATIONS

U.S. Appl. No. 12/467,944, Olesen et al., Portable Fitness Monitoring Systems, and Applications Thereof, filed May 18, 2009.

(Continued)

*Primary Examiner* — Brian T Gedeon
(74) *Attorney, Agent, or Firm* — Sterne, Kessler, Goldstein & Fox P.L.L.C.

(57) ABSTRACT

Program products, methods, and systems for providing fitness monitoring services are disclosed. In an embodiment, a method for providing heart rate information to a user of a portable fitness monitoring service includes: (a) defining a plurality of heart rate zones as ranges of percentages of a maximum heart rate; (b) associating a color with each of said heart rate zones; (c) receiving heart rate information from the user; and (d) providing a graphical display of the heart rate information, wherein a color of a portion of the graphical display corresponds with the color associated with one of said heart rate zones, wherein steps (a)-(d) are executed using at least one processor.

24 Claims, 47 Drawing Sheets

U.S. PATENT DOCUMENTS

| | | | |
|---|---|---|---|
| 5,976,083 A | 11/1999 | Richardson et al. | |
| 6,002,982 A | 12/1999 | Fry | |
| 6,010,430 A * | 1/2000 | Mankovtiz | 482/8 |
| 6,013,007 A | 1/2000 | Root et al. | |
| 6,080,110 A | 6/2000 | Thorgersen | |
| 6,080,111 A | 6/2000 | Pao-Lang | |
| 6,104,947 A | 8/2000 | Heikkila et al. | |
| 6,133,722 A | 10/2000 | Havel | |
| 6,135,951 A | 10/2000 | Richardson et al. | |
| 6,148,262 A | 11/2000 | Fry | |
| 6,163,718 A | 12/2000 | Fabrizio | |
| 6,230,047 B1 | 5/2001 | McHugh | |
| 6,251,048 B1 | 6/2001 | Kaufman | |
| 6,345,197 B1 | 2/2002 | Fabrizio | |
| 6,394,960 B1 | 5/2002 | Shinogi et al. | |
| 6,463,385 B1 | 10/2002 | Fry | |
| 6,572,636 B1 | 6/2003 | Hagen et al. | |
| 6,582,342 B2 | 6/2003 | Kaufman | |
| 6,585,622 B1 | 7/2003 | Shum et al. | |
| 6,607,493 B2 | 8/2003 | Song | |
| 6,716,139 B1 | 4/2004 | Hosseinzadeh-Dolkhani et al. | |
| 6,734,837 B1 | 5/2004 | Havel | |
| 6,736,759 B1 | 5/2004 | Stubbs et al. | |
| 6,745,069 B2 | 6/2004 | Nissila et al. | |
| 6,753,882 B2 | 6/2004 | Nakazawa et al. | |
| 6,758,816 B1 | 7/2004 | Tsubata et al. | |
| 6,798,378 B1 | 9/2004 | Walters | |
| 6,823,036 B1 | 11/2004 | Chen | |
| 6,832,109 B2 | 12/2004 | Nissila | |
| 6,837,827 B1 | 1/2005 | Lee et al. | |
| 6,853,955 B1 | 2/2005 | Burrell et al. | |
| 6,882,955 B1 | 4/2005 | Ohlenbusch et al. | |
| 7,057,551 B1 | 6/2006 | Vogt | |
| 7,062,225 B2 | 6/2006 | White | |
| 7,076,291 B2 | 7/2006 | Pulkkinen et al. | |
| 7,081,809 B1 * | 7/2006 | Mix et al. | 340/321 |
| 7,085,678 B1 | 8/2006 | Burrell et al. | |
| 7,097,588 B2 | 8/2006 | Watterson et al. | |
| 7,192,402 B2 | 3/2007 | Amano et al. | |
| 7,220,220 B2 | 5/2007 | Stubbs et al. | |
| 7,251,454 B2 | 7/2007 | White | |
| 7,254,516 B2 * | 8/2007 | Case et al. | 702/182 |
| 7,264,554 B2 * | 9/2007 | Bentley | 473/222 |
| 7,292,867 B2 | 11/2007 | Werner et al. | |
| 7,383,081 B2 | 6/2008 | Butt et al. | |
| 7,398,151 B1 | 7/2008 | Burrell et al. | |
| 7,480,512 B2 | 1/2009 | Graham et al. | |
| 7,518,054 B2 | 4/2009 | McKinney et al. | |
| 7,519,327 B2 | 4/2009 | White | |
| 7,603,255 B2 | 10/2009 | Case, Jr. et al. | |
| 7,689,283 B1 * | 3/2010 | Schecter | 607/18 |
| 7,771,320 B2 * | 8/2010 | Riley et al. | 482/9 |
| 7,909,737 B2 * | 3/2011 | Ellis et al. | 482/8 |
| 8,052,580 B2 * | 11/2011 | Saalasti et al. | 482/8 |
| 8,068,858 B2 * | 11/2011 | Werner et al. | 455/456.3 |
| 2001/0003542 A1 | 6/2001 | Kita | |
| 2002/0068873 A1 | 6/2002 | Nissila | |
| 2003/0069108 A1 * | 4/2003 | Kaiserman et al. | 482/8 |
| 2003/0171189 A1 | 9/2003 | Kaufman | |
| 2003/0224337 A1 | 12/2003 | Shum et al. | |
| 2004/0046692 A1 | 3/2004 | Robson et al. | |
| 2004/0102931 A1 | 5/2004 | Ellis et al. | |
| 2004/0116784 A1 | 6/2004 | Gavish | |
| 2004/0171956 A1 | 9/2004 | Babashan | |
| 2004/0199056 A1 | 10/2004 | Husemann et al. | |
| 2005/0049113 A1 | 3/2005 | Yueh et al. | |
| 2005/0124463 A1 | 6/2005 | Yeo et al. | |
| 2005/0195094 A1 | 9/2005 | White | |
| 2005/0197063 A1 | 9/2005 | White | |
| 2005/0256416 A1 | 11/2005 | Chen | |
| 2005/0266961 A1 | 12/2005 | Shum et al. | |
| 2006/0136173 A1 | 6/2006 | Case, Jr. et al. | |
| 2006/0169125 A1 | 8/2006 | Ashkenaze et al. | |
| 2006/0189360 A1 | 8/2006 | White | |
| 2006/0253210 A1 | 11/2006 | Rosenberg | |
| 2007/0006489 A1 | 1/2007 | Case, Jr. et al. | |
| 2007/0011919 A1 | 1/2007 | Case, Jr. | |
| 2007/0021269 A1 | 1/2007 | Shum | |
| 2007/0159926 A1 | 7/2007 | Prstojevich et al. | |
| 2007/0260421 A1 | 11/2007 | Berner, Jr. et al. | |
| 2008/0002528 A1 | 1/2008 | Andren et al. | |
| 2008/0004510 A1 | 1/2008 | Tanzawa et al. | |
| 2008/0009275 A1 | 1/2008 | Werner et al. | |
| 2008/0051993 A1 | 2/2008 | Graham et al. | |
| 2008/0058971 A1 | 3/2008 | Graham et al. | |
| 2008/0059064 A1 | 3/2008 | Werner et al. | |
| 2008/0065319 A1 | 3/2008 | Graham et al. | |
| 2008/0096726 A1 | 4/2008 | Riley et al. | |
| 2008/0101161 A1 | 5/2008 | Imai et al. | |
| 2008/0103689 A1 | 5/2008 | Graham et al. | |
| 2008/0171636 A1 | 7/2008 | Usui et al. | |
| 2008/0200310 A1 | 8/2008 | Taliabue | |
| 2008/0319661 A1 | 12/2008 | Werner et al. | |
| 2009/0047645 A1 | 2/2009 | Dibenedetto et al. | |
| 2009/0048044 A1 | 2/2009 | Oleson et al. | |
| 2009/0048070 A1 | 2/2009 | Vincent et al. | |
| 2009/0233770 A1 | 9/2009 | Vincent et al. | |
| 2010/0292050 A1 * | 11/2010 | DiBenedetto et al. | 482/9 |
| 2010/0292599 A1 * | 11/2010 | Oleson et al. | 600/519 |

FOREIGN PATENT DOCUMENTS

| | | | |
|---|---|---|---|
| WO | WO 2008/0101168 A2 | 8/2008 | |
| WO | WO2009033034 | 3/2009 | |

OTHER PUBLICATIONS

U.S. Appl. No. 12/467,948, Oleson et al., Portable Fitness Monitoring Systems With Displays and Applications Thereof, filed May 18, 2009.

* cited by examiner

FIG. 5

| ZONE | COLOR | % OF MAX HR |
|---|---|---|
| ENERGY | BLUE | 65-75% |
| ENDURANCE | GREEN | 75-85% |
| STRENGTH | YELLOW | 85-90% |
| POWER | RED | 90-95% |

FIG. 8

HOME > EQUIPMENT

WHAT'S THE DIFFERENCE BETWEEN THESE? WE'LL HELP YOU FIGURE OUT THE RIGHT TRAINING EQUIPMENT TO HELP YOU ACHIEVE YOUR GOAL.

JUMP IN & SIGN UP!
(ALREADY REGISTERED? LOG IN)
> CHECKOUT PLANS

| | MOBILE APPLICATION | +MP3 PLAYER | | WATCH | MP3 PLAYER |
|---|---|---|---|---|---|
| | >SEE DETAILS | >SEE DETAILS | >SEE DETAILS | >SEE DETAILS | >SEE DETAILS |
| I WANT... | ...THE COACHING AND I ALREADY HAVE A COMPATIBLE DEVICE. | ...THE COACHING BUT I ALREADY HAVE A MUSIC PLAYER I LIKE. | ...TO SELF TRAIN WITH A SIMPLE DEVICE THAT DISPLAYS ZONES. | ...A SIMPLE DEVICE THAT JUST TRACKS MY VITALS. | ...ALL THE COACHING FEATURES WITH MUSIC, BUT NOT A NEW PHONE. |
| TRAINING FEATURES | ADVANCED COACHING NARRATION; GPS LOCATION DATA | COACHING NARRATION | | | ADVANCED COACHING NARRATION |
| WEBSITE INTEGRATION | | | NONE | USB DATA UPLOAD ONLY | USB DATA UPLOAD/DOWNLOAD |
| ADDITIONAL FEATURE | | PERSONAL MUSIC DEVICE COMPATIBLE | | TIME DEVICE | PLAYS MUSIC |
| ADDITIONAL TRAINING COMPONENTS | | | NONE | | |
| SOFTWARE DOWNLOAD | MOBILE APP MANAGER | MANAGER | | MANAGER | MANAGER |

LOOKING FOR THE PHONE OR SYNCHRONIZER DOWNLOAD? SEE THE PHONE INFORMATION PAGE.

LEARN TO RUN

PRACTICE RUNNING FREELY. MASTER THE BASICS OF HEART RATE TRAINING, PROPER FORM AND NEW TERMINOLOGY. LEARN TO ENJOY RUNNING!

CHOOSE THE LEVEL OF DIFFICULTY

| 1 | 2 | 3 | 4 | 5 | 6 | 7 |

314

LEVEL 2 - START HERE IF YOU CAN ONLY RUN FOR SHORT 5-MINUTE BURSTS OR LESS. ← 316

WHAT TO EXPECT
START WITH 1-MINUTE RUNNING BURSTS AND SLOWLY BUILD UP TO LONGER SEGMENTS.

BENEFITS
BUILD THE ENDURANCE TO RUN FOR 10 MINUTES, BE READY FOR LEVEL 3!

PLAN AT A GLANCE

⊙ PREVIEW WORKOUT LIST

RECOMMENDED SCHEDULE

| WORKOUTS | PER WEEK | WEEKS |
|----------|----------|-------|
| 34 | 3 | 12 |

NEXT STEP-PERSONALIZE

SHOP   SIGN UP   UNITED STATES   STORE FINDER
◉ GO BACK

204

START | PLAN | SCHEDULE | TRACK | SUPPORT

HELP/CONTACT US   ABOUT US   CAREERS   PRESS   PARTNERS   CORPORATE INFORMATION   LEGAL   STORE LOCATOR   WARNING: EMAIL SCAM

HI, RICH!   LOG OUT

DONE

*FIG. 12*

BE FIT—IN THE GYM

ADD VARIETY TO YOUR BASELINE GYM ROUTINE WITH INTERVAL WORKOUTS AND MULTIPLE CARDIO MACHINE OPTIONS.

314

CHOOSE THE LEVEL OF DIFFICULTY

| 1 | 2 | 3 | 4 | 5 | 6 | 7 |

LEVEL 4 - YOU SPEND 25 MINUTES OR LESS ON CARDIO: YOU'RE READY TO TAKE IT UP A NOTCH. — 316

WHAT TO EXPECT
GET TO KNOW THE WORLD OF YELLOW ZONE SPRINTS AND HIGHER-INTENSITY WORKOUTS.

BENEFITS
DEEPEN YOUR CARDIO AND HAVE FUN AT THE SAME TIME. WORK TOWARDS A MUCH STRONGER FOUNDATION.

PLAN AT A GLANCE

⊙ PREVIEW WORKOUT LIST

RECOMMENDED SCHEDULE

| WORKOUTS | PER WEEK | WEEKS |
|---|---|---|
| 34 | 4 | 9 |

NEXT STEP—PERSONALIZE

FINISH FASTER—MARATHON

GET READY TO DIG DEEP AND BASK IN THE RESULTS! THIS PLAN WILL CHALLENGE YOUR BODY TO IMPROVE YOUR LONG-DISTANCE AEROBIC CAPACITY. TARGET THE MARATHON TIME!

CHOOSE THE LEVEL OF DIFFICULTY

| 1 | 2 | 3 | 4 | 5 | 6 | 7 |

314

316 — LEVEL 6: YOU'VE GONE THE DISTANCE, NOW CONQUER THE 03:35: MARATHON.

WHAT TO EXPECT
BE PREPARED TO BUILD A BASE OF 30+ MILES PER WEEK AND RUN ABOUT 40+ MILES PER WEEK AT YOUR PEAK. PRACTICE YELLOW ZONE THRESHOLD WORKOUTS. THIS ISN'T EASY, BUT YOUR HARD WORK WILL PAY OFF ON RACE DAY!

BENEFITS
PREPARE FOR A FINISHING TIME UNDER 03:35 HOURS.

PLAN AT A GLANCE

⊚ PREVIEW WORKOUT LIST

RECOMMENDED SCHEDULE

| WORKOUTS | PER WEEK | WEEKS |
|----------|----------|-------|
| 124 | 6 | 21 |

NEXT STEP—PERSONALIZE

⊚ GO BACK

SHOP    SIGN UP    STORE FINDER    UNITED STATES

204 — START  PLAN  SCHEDULE  TRACK  SUPPORT

HELP/CONTACT US  ABOUT US  CAREERS  PRESS  PARTNERS  CORPORATE INFORMATION  LEGAL  STORE LOCATOR  WARNING: EMAIL SCAM

HI, RICH!    LOG OUT

DONE

FIG. 17

RUN A RACE – 10K RACE

STEP 1: OK. HOW WOULD YOU LIKE TO SCHEDULE YOUR PLAN?

⦿ BY RACE DATE ○ BY START DATE

DAY OF THE RACE [07/04/2009] 📅 DAY TO START TRAINING [04/21/2009] 📅

STEP 2: HOW MANY DAYS PER WEEK DO YOU WANT TO WORK OUT?

[SUN] [MON] [TUE] [WED] [THU] [FRI] [SAT]

STEP 3: NAME YOUR PLAN AND YOU'RE READY TO START. [RUN A RACE – 10K RACE]

COACH TIP:
4 TIMES A WEEK SHOULD GET YOU 10K STRONG. AIM FOR REST DAYS IN BETWEEN. BELIEVES IN REST AFTER RUNNING. IF YOU CHOOSE THE MAX 7 DAYS A WEEK, THE 7TH DAY WILL BE A REST DAY.

⊙ GO BACK

MY SCHEDULE
DURATION: TUE, 21 APR 2009 – SAT, 4 JUL 2009

| WORKOUTS | PER WEEK | WEEKS |
|---|---|---|
| 42 | 4 | 11 |

NEXT STEP – COMPLETE

WORKOUT JOURNAL FOR APR 2009 – FEB 2008

| DATE | NAME | TIME | CALORIES | DISTANCE | HEART RATE | AVERAGE PACE | STRIDE RATE | RATING | NOTES |
|---|---|---|---|---|---|---|---|---|---|
| SAT, 28 FEB 2009 | RUN0004 | 43:50 | 472 | 5.91 MILES | 164 BPM | 07:18 MIN/MI | 169 STEPS/MIN | ★★★ | THIS WAS A FUN RUN! |
| SUN, 1 MAR 2009 | RUN0005 | 01:14:06 | 787 | 9.76 MILES | 162 BPM | 07:23 MIN/MI | 167 STEPS/MIN | | |
| MON, 2 MAR 2009 | RUN0006 | 31:18 | 233 | 4.06 MILES | 143 BPM | 07:32 MIN/MI | 171 STEPS/MIN | | |
| WED, 4 MAR 2009 | RUN0007 | 37:34 | 339 | 5.14 MILES | 153 BPM | 07:11 MIN/MI | 170 STEPS/MIN | | |
| FRI, 6 MAR 2009 | RUN0008 | 01:07:11 | 528 | 8 MILES | 146 BPM | 08:24 MIN/MI | 163 STEPS/MIN | ★★★ | |
| SAT, 7 MAR 2009 | RUN0009 | 25:35 | 280 | 3.8 MILES | 165 BPM | 06:44 MIN/MI | 172 STEPS/MIN | | |
| MON, 9 MAR 2009 | RUN0010 | 54:05 | 593 | 8 MILES | 167 BPM | 06:46 MIN/MI | 169 STEPS/MIN | | |
| TUE, 10 MAR 2009 | RUN0011 | 45:05 | 505 | 6.6 MILES | 168 BPM | 06:49 MIN/MI | 169 STEPS/MIN | ★★ | |
| WED, 11 MAR 2009 | RUN0012 | 02:33 | 3 | 4.2 MILES | 0 BPM | 00:35 MIN/MI | 0 STEPS/MIN | | |
| FRI, 13 MAR 2009 | RUN0013 | 35:37 | 326 | 5 MILES | 0 BPM | 07:06 MIN/MI | 167 STEPS/MIN | | |
| SUN, 15 MAR 2009 | RUN0014 | 59:58 | 326 | 9.3 MILES | 0 BPM | 06:26 MIN/MI | 171 STEPS/MIN | | |
| FRI, 27 MAR 2009 | RUN0015 | 42:55 | 314 | 5.21 MILES | 144 BPM | 08:14 MIN/MI | 165 STEPS/MIN | | |
| TUE, 31 MAR 2009 | RUN0016 | 24:23 | 168 | 3 MILES | 136 BPM | 07:40 MIN/MI | 168 STEPS/MIN | | |
| TUE, 7 APR 2009 | RUN0017 | 23:42 | 240 | 3.5 MILES | 161 BPM | --:-- MIN/MI | 0 STEPS/MIN | | |
| WED, 8 APR 2009 | RUN0018 | 26:05 | 294 | 3.92 MILES | 170 BPM | 06:39 MIN/MI | 168 STEPS/MIN | | |

FIG. 23

| PERSONAL INFO | WORKOUT SETTINGS | DEVICE SETTINGS | PRIVACY AND SHARING |

① ▶ UNITS OF MEASURE

DISTANCE UNITS  ⊙ MILES  ○ KILOMETERS

HEIGHT/WEIGHT UNITS  ⊙ FEET POUNDS  ○ CENTIMETERS KILOGRAMS

TIME FORMAT  ⊙ 12 HOUR  ○ 24 HOUR

START WEEK ON  ⊙ SUNDAY  ○ MONDAY

② ▶ FITNESS INFO

YOUR FITNESS INFORMATION HELPS BETTER ANALYZE YOUR PERFORMANCE. HEIGHT AND WEIGHT WILL HELP MORE ACCURATELY CALCULATE YOUR CALORIES BURNED. REMEMBER, CHANGING YOUR MAX. HEART RATE AFFECTS YOUR PLANS, SO BE SURE TO RE-SYNC YOUR PHONE.

\* WEIGHT  [165] LBS

\* HEIGHT  [5] FT [10] IN

\* MAX. HEART RATE  [190] BPM  ②Ⓐ ⓘ

②Ⓑ ▶ [UPDATE YOUR ZONES]

②Ⓒ YOUR ZONES

RED: 171–180 BPM
YELLOW: 162–170 BPM
GREEN: 143–161 BPM
BLUE: 114–142 BPM

②Ⓓ ▶ [zone chart image]

CLICK ON EACH ZONE COLOR FOR DETAILS

③ ▶ PACE ZONES

IF YOU KNOW THEM, SET YOUR CUSTOM ZONES HERE. YOU MAY FILL OUT AS MANY OR AS LITTLE AS YOU LIKE.

PACE UNITS: [MIN/MILE ▾]

1: RELAXED  ⓘ  [11 ▾] [00 ▾] MIN/MILE
2: SLOWER   ⓘ  [-- ▾] [-- ▾] MIN/MILE
3: SLOW     ⓘ  [-- ▾] [-- ▾] MIN/MILE
4: MEDIUM   ⓘ  [8 ▾]  [30 ▾] MIN/MILE
5: FAST     ⓘ  [7 ▾]  [55 ▾] MIN/MILE
6: FASTER   ⓘ  [-- ▾] [-- ▾] MIN/MILE
7: FASTEST  ⓘ  [6 ▾]  [50 ▾] MIN/MILE

*FIG. 41*

| PERSONAL INFO | WORKOUT SETTINGS | DEVICE SETTINGS | PRIVACY AND SHARING |

DEVICES

① ☐ I HAVE A _____ PHONE (MODEL NNN-NNNN)

② ▸ NARRATION VOICE OPTIONS (CHOOSE UP TO 5)

```
CHINESE-CANTONESE: MALE          ENGLISH-UK: FEMALE
CHINESE-MANDARIN: FEMALE         ENGLISH-UK: MALE
FRENCH: FEMALE                   ENGLISH-US: FEMALE
GERMAN: MALE                     ENGLISH-US: MALE
ITALIAN: FEMALE
JAPANESE: FEMALE         ADD >
KOREAN: FEMALE
PORTUGESE-BRAZIL: FEMALE  < REMOVE
RUSSIAN: MALE
SPANISH: FEMALE
```

③ ▸ ☐ SKIP WARM UP/COOL DOWN EXERCISES ON ALL WORKOUTS ⓘ

④ ▸ ☑ I HAVE _____ (MODEL NNN-NNNN)

NARRATION VOICE OPTIONS

[ ENGLISH - UK  ▾ ]

⑤ ▸ STATS UPDATE ANNOUNCEMENTS DURING WORKOUT

DURING YOUR WORKOUT, YOUR VITALS WILL BE ANNOUNCED WHEN YOU CHOOSE TO HEAR AN UPDATE AND AUTOMATICALLY AFTER REACHING 25%, 50%, 75%, AND COMPLETION OF YOUR WORKOUT. CHOOSE WHICH STATS ARE ANNOUNCED DURING THESE UPDATES.

☐ REPEAT THE LATEST COACHING INSTRUCTION
☑ TIME ELAPSED
☑ CALORIES BURNED
☑ DISTANCE TRAVELED
☐ HEART RATE ZONE AT THE TIME
☐ HEART RATE VALUE AT THE TIME
☐ PACE AT THE TIME
☐ STRIDE RATE AT THE TIME

ACCESSORIES

⑥ ▸ SELECT THE ACCESSORIES YOU WILL BE WORKING OUT WITH SO KNOWS TO CONNECT TO THEM DURING YOUR WORKOUT.

☐ STRIDE RATE MONITOR (MODEL NNN-NNNN)

☐ HEART RATE MONITOR (MODEL NNN-NNNN)

FIG. 42

① CONNECT WITH FACEBOOK
YOUR ACCOUNT IS SUCCESSFULLY CONNECTED TO YOUR FACEBOOOK ACCOUNT, <USER'S EMAIL ADDRESS>, USING FACEBOOK CONNECT.

QUESTIONS ABOUT HOW THIS WORKS? CHECK OUT THE FACEBOOK CONNECT HELP SECTION FOR DETAILS.

[X DISCONNECT] ◄─①A

② FACEBOOK CONNECT SETTINGS

②A ► CHECK WHEN IS ALLOWED TO PUBLISH TO YOUR FACEBOOK FEED.

☑ WHEN SYNC IS COMPLETED [EACH TIME ▸]

☑ WHEN WORKOUT STATS WERE MANUALLY ENTERED [DAILY ▸]

☑ WHEN A PLAN IS CREATED [WEEKLY ▸]

②B ► CHECK WHAT YOU WOULD LIKE TO AUTOMATICALLY PUBLISH TO YOUR FACEBOOK FEED.

☑ ACHIEVEMENTS
(CALORIES YOU BURNED OVER YOUR LIFETIME ON HOURS EXCERCISED, ETC.)

☑ MILESTONES
(RAN ANOTHER 100 MILES OR REACHED THE LENGTH OF THE CHANNEL, ETC.)

☑ PERSONAL RECORD (PR)
(REACHED A NEW FASTEST MILE PACE, ETC.)

②C ☑ PLAN PROGRESS
(PERCENTAGE OF PLAN COMPLETED, NUMBER OF WORKOUTS DONE, PLAN STATS, ETC.)

☑ WORKOUT STATS
(COMPLETED WORKOUT STATS INCLUDING DISTANCE, TIME, CALORIES, AND MORE)

③ ► PROFILE PRIVACY SETTINGS (NATIVE COMMUNITY)
CHECK ELEMENTS YOU WOULD LIKE TO DISPLAY ON YOUR PROFILE. BY DEFAULT, YOUR SCREEN NAME WILL BE SHOWN.

☑ PERSONAL INFORMATION
(FULL NAME, AGE, GENDER, LOCATION)

☑ PHOTO / AVATAR
CHOOSE PHOTO / AVATAR: [_____] [BROWSE]

[AVATAR]

☑ WORKOUTS
(LATEST COMPLETED WORKOUT CHART, IF ANY)

☑ PROGRESS
(PLAN PROGRESS, CUMULATIVE STATS, ACHIEVEMENTS AREA)

④ ► PROFILE CUSTOM URL (NATIVE COMMUNITY)

MAKE PROFILE
⦿ PUBLIC – ANYONE CAN SEE
PUBLIC URL: http://_____.com/
○ PRIVATE – ONLY PARTICIPANTS OF JOINT CONTESTS CAN SEE

PROGRAM PRODUCTS, METHODS, AND SYSTEMS FOR PROVIDING FITNESS MONITORING SERVICES

This application is related to commonly owned U.S. patent application Ser. No. 12/467,944, titled "Portable Fitness Monitoring Systems, and Applications Thereof," filed on the same day herewith, and commonly owned U.S. patent application Ser. No. 12/467,948, titled "Portable Fitness Monitoring Systems With Displays, and Applications Thereof," filed on the same day herewith, each of which is incorporated herein by reference in its entirety.

FIELD OF THE INVENTION

The present invention generally relates to fitness monitoring services. More particularly, the present invention relates to program products, methods, and systems for providing fitness monitoring services.

BACKGROUND OF THE INVENTION

Exercise is important to maintaining a healthy lifestyle and individual well-being. Accordingly, many individuals want to participate in an exercise program. The most successful exercise programs are ones tailored to a fitness level of an individual and aimed at assisting the individual to achieve one or more specific fitness or exercise goals.

Sports trainers, as well as other exercise and fitness professionals, are available to assist individuals in developing exercise programs appropriate for their individual fitness levels and their specific fitness or exercise goals. Hiring such professionals, however, can be expensive. Furthermore, the busy schedules of many individuals make it difficult for these individuals to set aside time to meet with an exercise and fitness professional on a routine basis. Thus, many individuals forego using the services of exercise and fitness professionals, and they never achieve the benefits that can be obtained from an exercise program tailored, for example, to one's fitness level.

Technology has resulted in the development of systems capable of transferring performance information obtained from a user during a workout to a remote computer for further analysis. These systems often provide a user interface that allows the user to review their past performance data.

What is needed are improved program products, methods, and systems for providing fitness monitoring services that will allow athletes to, among other thing, better use data generated from past performances to gauge their improvement, to set goals for the future, to share their performance data with others, to stay motivated, and/or to enable them to exercise at intensities appropriate for their current fitness level and goals.

BRIEF SUMMARY OF THE INVENTION

Embodiments of the present invention relate to a method for providing heart rate information to a user of a portable fitness monitoring service includes: (a) defining a plurality of heart rate zones as ranges of percentages of a maximum heart rate; (b) associating a color with each of said heart rate zones; (c) receiving heart rate information from the user; and (d) providing a graphical display of the heart rate information, wherein a color of a portion of the graphical display corresponds with the color associated with one of said heart rate zones, wherein steps (a)-(d) are executed using at least one processor.

Embodiments of the present invention also relate to a tangible computer program product including a computer readable medium having computer program logic recorded thereon for causing at least one processor to: graphically display first performance parameter information to a user regarding an athlete's performance during a workout, wherein the first performance parameter information is displayed as a function of an interval parameter; and graphically display second performance parameter information to a user regarding an athlete's performance during a workout, wherein the second performance parameter information is displayed as a function of an interval parameter, wherein the second performance parameter information is overlaid on top of the first performance parameter information.

Embodiments of the present invention further relate to a tangible computer program product including a computer readable medium having computer program logic recorded thereon for causing at least one processor to: graphically display performance parameter information to a user regarding an athlete's performance during a workout, wherein the performance parameter information is displayed as a function of an interval parameter; provide first and second analysis boundary markers capable of being manipulated by the user to define a subset of the graphically displayed performance parameter information; and in response to the user manipulation, display numerical performance parameter information corresponding to only the subset of graphically displayed performance parameter information defined by the analysis boundary markers.

Further embodiments, features, and advantages of the present invention, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate the present invention by way of example, and not by way of limitation, and, together with the description, further serve to explain the principles of the invention and to enable a person skilled in the pertinent art to make and use the invention.

FIG. 5 is an exemplary GUI window according to an embodiment of the present invention.

FIG. 8 is a table that illustrates heart rate zone ranges according to an embodiment of the present invention.

FIG. 9 is an exemplary GUI window according to an embodiment of the present invention.

FIG. 11 is an exemplary GUI window according to an embodiment of the present invention.

FIG. 12 is an exemplary GUI window according to an embodiment of the present invention.

FIG. 13 is an exemplary GUI window according to an embodiment of the present invention.

Figure 14:
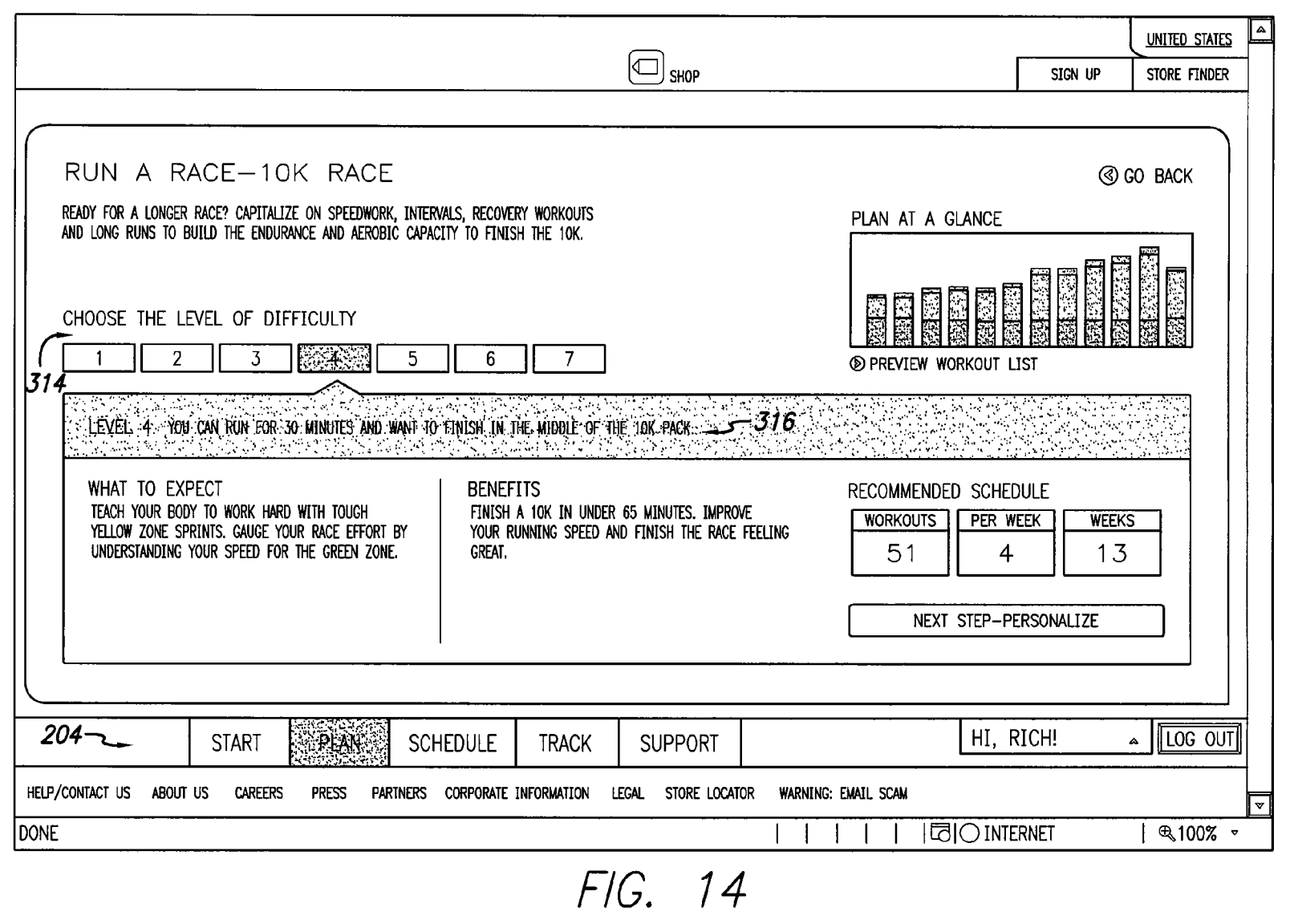

FIG. 14 is an exemplary GUI window according to an embodiment of the present invention.

Figure 15:
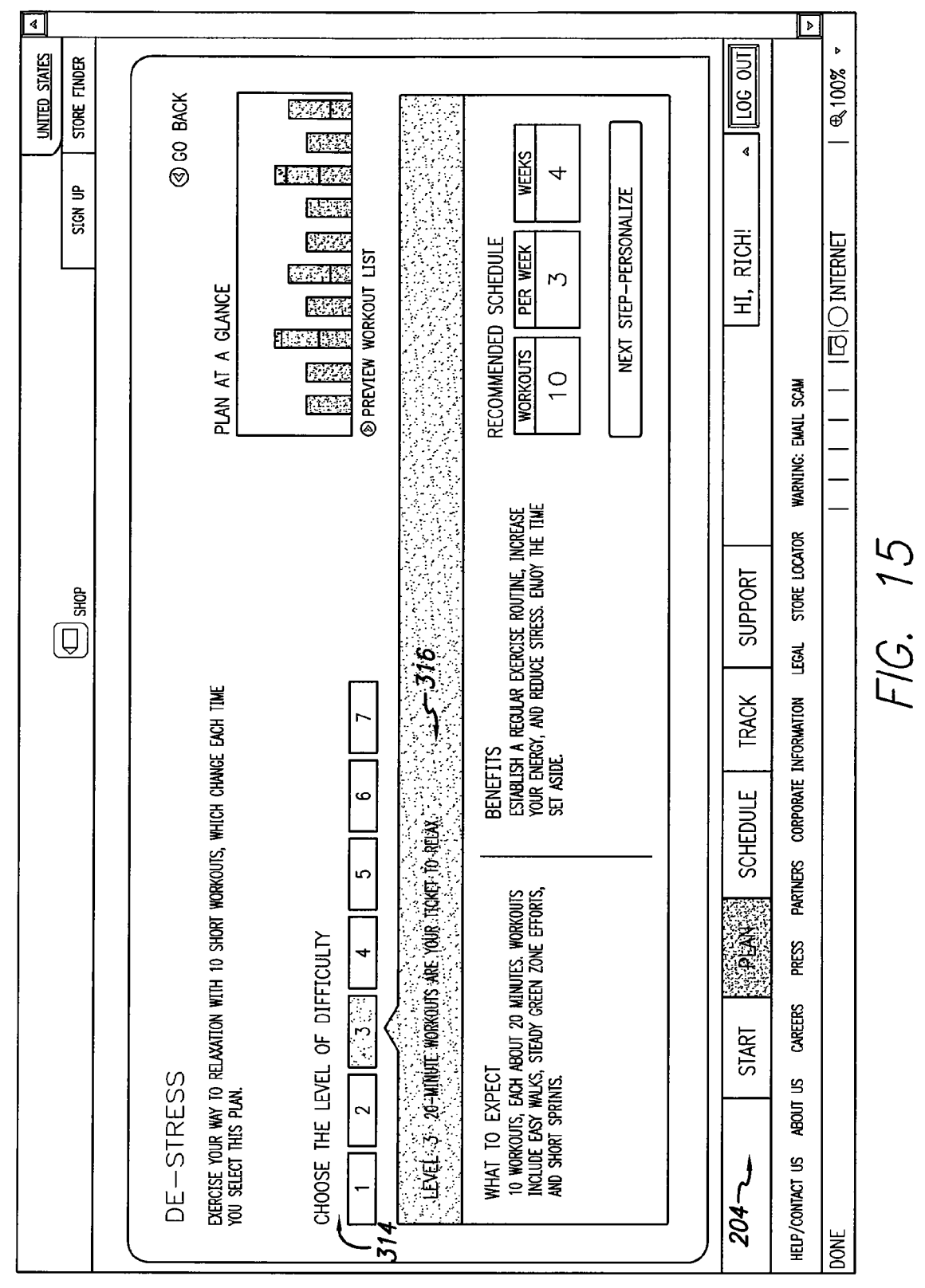

FIG. 15 is an exemplary GUI window according to an embodiment of the present invention.

Figure 16:
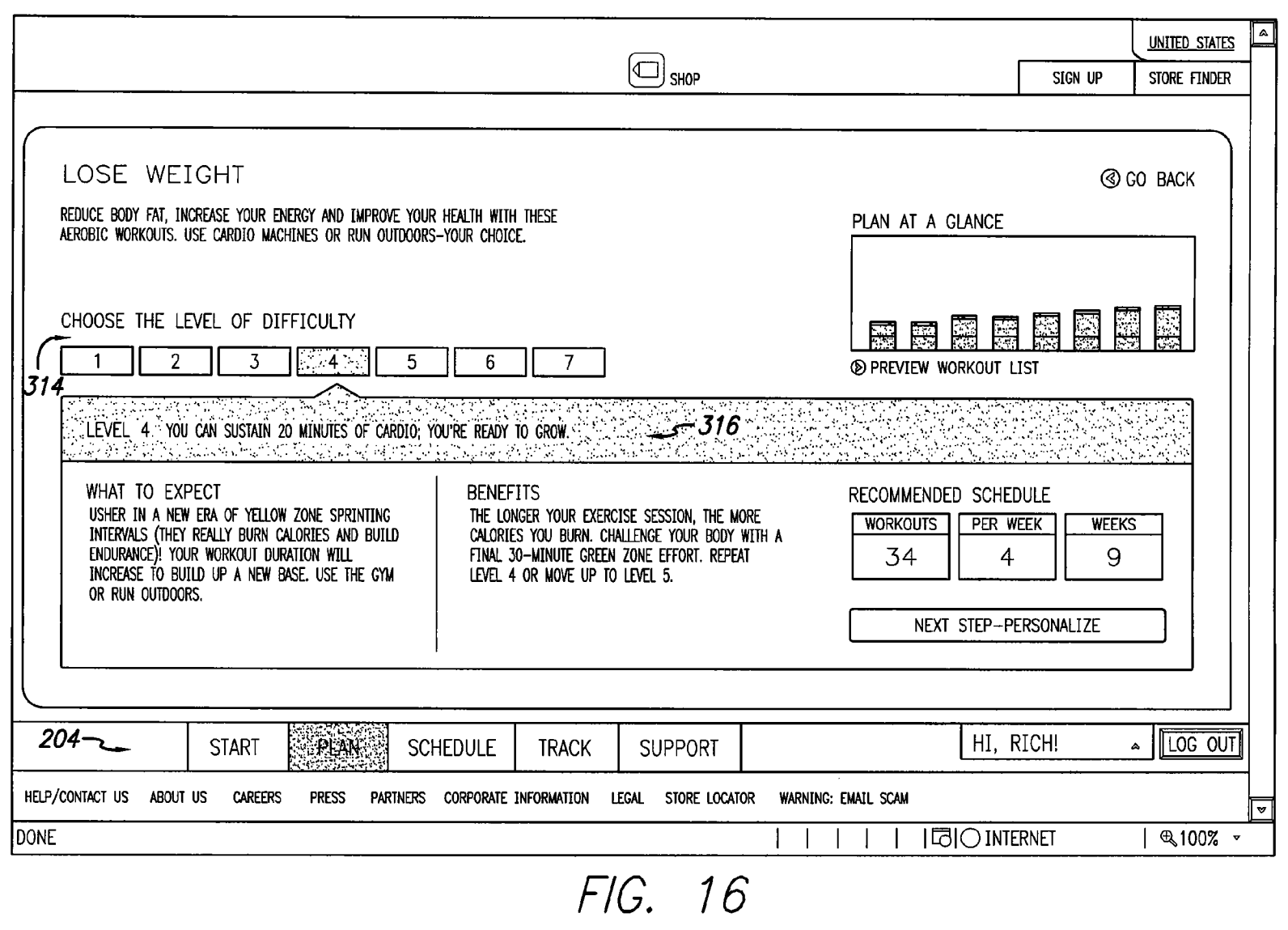

FIG. 16 is an exemplary GUI window according to an embodiment of the present invention.

FIG. 17 is an exemplary GUI window according to an embodiment of the present invention.

FIG. 19 is an exemplary GUI window according to an embodiment of the present invention.

FIG. 20 is an exemplary GUI window according to an embodiment of the present invention.

FIG. 23 is an exemplary GUI window according to an embodiment of the present invention.

FIG. 24 is an exemplary GUI window according to an embodiment of the present invention.

FIG. 36 is an exemplary GUI window according to an embodiment of the present invention.

FIG. 37 is an exemplary GUI window according to an embodiment of the present invention.

FIG. 40 is an exemplary GUI window according to an embodiment of the present invention.

FIG. 41 is an exemplary GUI window according to an embodiment of the present invention.

FIG. 42 is an exemplary GUI window according to an embodiment of the present invention.

FIG. 43 is an exemplary GUI window according to an embodiment of the present invention.

FIG. 45 is an exemplary GUI window according to an embodiment of the present invention.

FIG. 47 is an exemplary GUI window according to an embodiment of the present invention.

DETAILED DESCRIPTION OF THE INVENTION

The present invention will now be described in detail with reference to embodiments thereof as illustrated in the accompanying drawings. References to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The program products, methods, and systems of the present invention may be used to provide fitness monitoring services to athletes 100. Athletes 100 who utilize embodiments of the present invention may actively participate in a variety of physical activities including, but not limited to, running, walking, biking, skating, swimming, skiing, performing aerobic exercises, weight lifting, or participating in various individual or team sports. Accordingly, terms such as, for example, "athlete," "runner," "exercising individual," and "user" may be referred to herein interchangeably.

Furthermore, the term "user" may also be used herein to refer to a user other than the athlete 100 conducting the physical activities of interest. In other words, as described in further detail below, other users besides the athlete user, such as coaches or friends may be able to interact with the system of the present invention.

Figure 1:
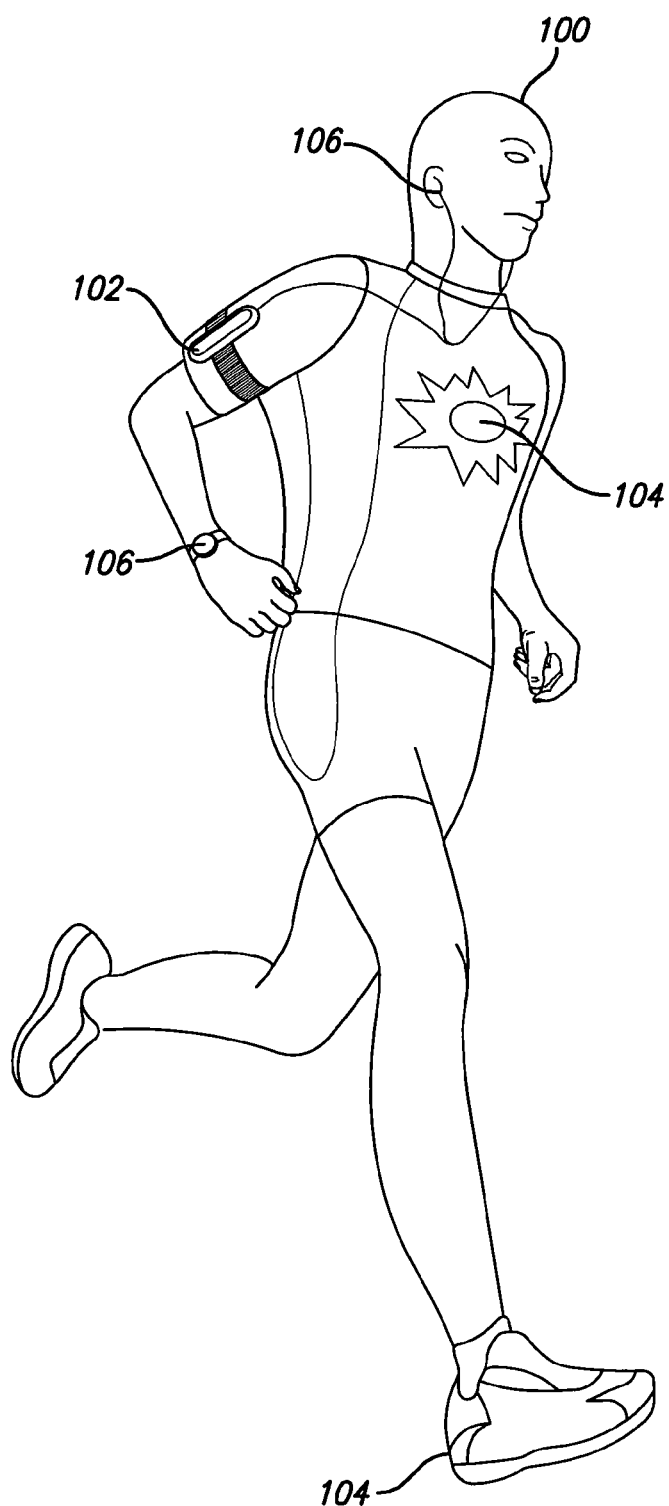
FIG. 1 is an illustration of a fitness monitoring system according to an embodiment of the present invention.

As illustrated in FIG. 1, an athlete 100 engaged in physical activity may be equipped with a portable fitness monitoring device 102. The portable fitness monitoring device 102 may be worn, carried, or otherwise supported by the athlete 100 during the physical activity. The portable fitness monitoring device 102 may be adapted to measure and/or process various performance parameters associated with the athlete's 100 physical activity. The term "performance parameters" may include both physical parameters and physiological parameters associated with the athlete's 100 physical activity. Physical parameters measured may include, for example, time, distance, speed, pace, stride count, stride length, and stride rate. Physiological parameters measured may include, for example, heart rate, respiration rate, blood oxygen level, blood flow, hydration status, calories burned, muscle fatigue, and body temperature.

In an embodiment, performance parameters may also include mental or emotional parameters such as, for example, stress level or motivation level. Mental and emotional parameters may be measured directly or indirectly either through posing questions to the athlete 100 or by measuring things such as, for example, trunk angle or foot strike characteristics while running.

The portable fitness monitoring device 102 may be a device such as, for example, a mobile phone, a personal digital assistant, a music file player (e.g. and MP3 player), an intelligent article for wearing (e.g. a fitness monitoring garment, wrist band, or watch), a dongle (e.g. a small hardware device that protects software) that includes a fitness monitoring mode, a dedicated portable fitness monitoring device 102, or a non-dedicated portable fitness monitoring device 102, such as, for example, the devices disclosed in commonly owned U.S. patent application Ser. No. 12/467,944, titled "Portable Fitness Monitoring Systems, and Applications Thereof".

The portable fitness monitoring device 102 may communicate with one or more sensors 104 for detecting the performance parameters. The sensors 104 may be in wired or wireless communication with the portable fitness monitoring device 102. In one embodiment of the present invention, as shown in FIG. 1, a sensor 104 for detecting heart rate is coupled to the athlete's 100 chest, while a sensor 104 for detecting speed is coupled to the athlete's 100 shoe. Other sensors 104 including, but not limited to, an accelerometer, a pedometer, a pulsimeter, a thermometer, or other sensor 104 for detecting a user 100 performance parameter may be used. The portable monitoring device 102 and the one or more sensors 104 may communicate using known protocols, including, but not limited to, ANT and ANT+, by Dynastream Innovations, Bluetooth LE, Bluetooth LET, or BlueRobin. Other known communication protocols may be used.

The portable fitness monitoring device 102 may also communicate with one or more portable displays 106. The portable displays 106 may be in wired or wireless communication with the portable fitness monitoring device 102. The portable displays 106 may be adapted to convey information to the athlete 100 in a variety of ways such as, for example, visually, audibly, or tactilely (e.g. via a vibrating element), either alone or in combination. In an embodiment of the present invention, as shown in FIG. 1, a separate audible display 106 (e.g. headphones) and a separate visual display 106 (e.g. a wrist band) are provided. In other embodiments, visual, audible, and/or tactile displays 106 may be included as physically separate elements, or one or more of these elements may be integrated into a single physical display device 106. Tactile displays 106 may include means for vibrating the display 106, such as, for example, a piezoelectric actuator, for providing tactile sensory output to the athlete 100. In some embodiments, the portable display 106 may be integral with the portable fitness monitoring device 102.

According to an embodiment of the present invention, information may be communicated between an athlete 100 equipped with a portable fitness monitoring device 102 and one or more external elements. These external elements may include, for example, a personal computer 114, a network 110, and/or a server 112. In one embodiment, personal computer 114 and server 112 may be a single component.

Figure 2:
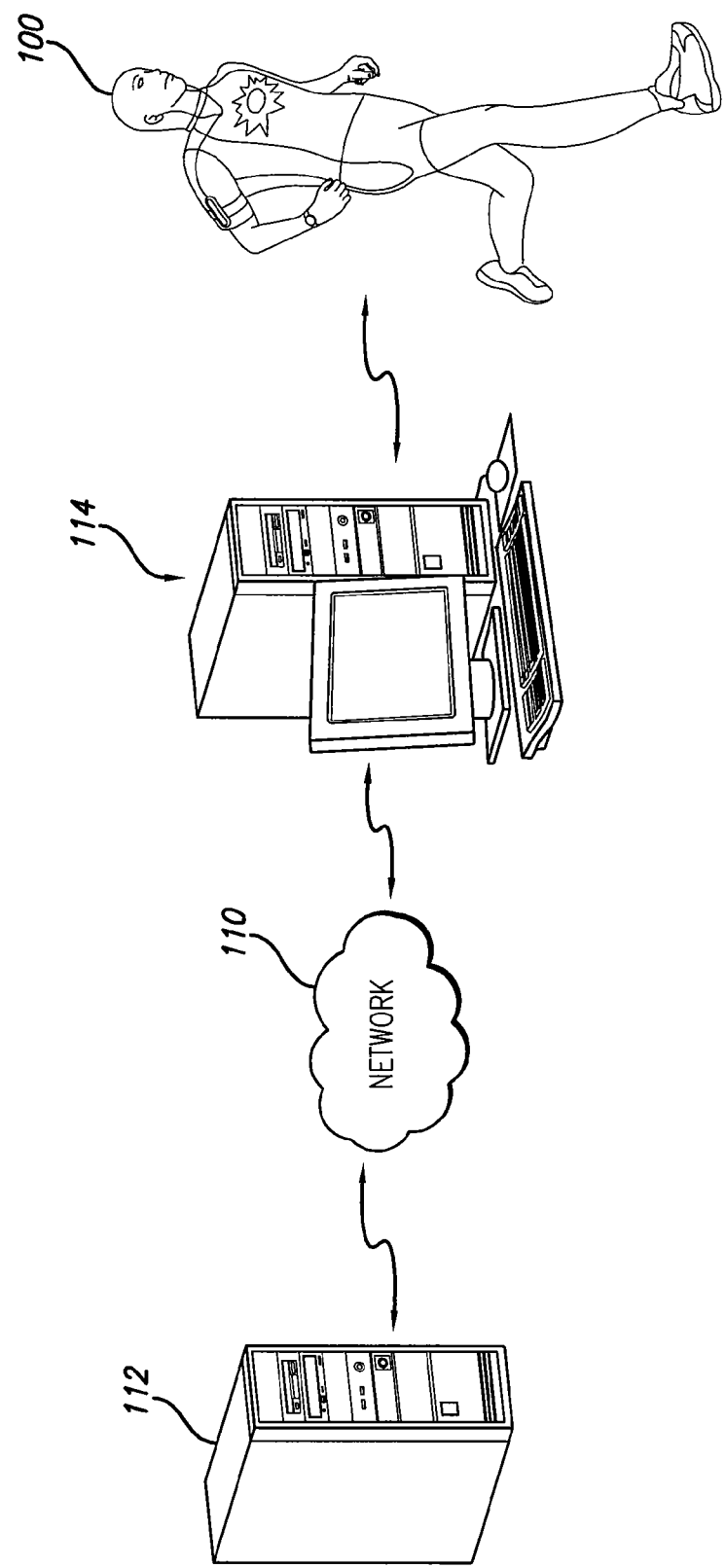
FIG. 2 is an illustration of an athlete communicating with a computer and/or a server.

In one embodiment, as shown in FIG. 2, the athlete 100 equipped with a portable fitness monitoring device 102 may communicate with a personal computer 114 using wired or wireless communications. As will be appreciated by those of ordinary skill in the art, wired communication between the portable fitness monitoring device 102 and the personal computer 114 may be achieved, for example, by placing the portable fitness monitoring device 102 in a docking unit that is attached to the personal computer 114 using a communications wire plugged into a communications port of the personal computer 114.

In another embodiment, wired communication between the portable fitness monitoring device 102 and the personal computer 114 may be achieved, for example, by connecting a cable between the portable fitness monitoring device 102 and the computer 114. A computer input/output of the portable fitness monitoring device 102 and a communications port of the computer 114 may include USB ports. The cable connecting the portable fitness monitoring device 102 and the computer 114 may be a USB cable with suitable USB plugs including, but not limited to, USB-A or USB-B regular, mini, or micro plugs.

Wireless communication between the portable fitness monitoring device 102 and the personal computer 114 may be achieved, for example, by way of a wireless wide area network (WWAN—such as, for example, the Internet), a wireless local area network (WLAN), or a wireless personal area network (WPAN) (collectively, wireless area networks or WANs). As is well known to those skilled in the art, there are a number of known standard and proprietary protocols that are suitable for implementing WANs (e.g. TCP/IP, IEEE 802.16, and Bluetooth). Accordingly, the present invention is not limited to using any particular protocol to communicate between the portable fitness monitoring device 102 and the various external elements of the fitness monitoring service of the present invention.

In one embodiment, the portable fitness monitoring device 102 may communicate with a WWAN communications system such as that employed by mobile telephones. For example, a WWAN communication system may include a plurality of geographically distributed communication towers and base station systems. Communication towers may include one or more antennae supporting long range two-way radio frequency communication wireless devices, such as the portable fitness monitoring device 102. The radio frequency communication between antennae and the portable fitness monitoring device 102 may utilize radio frequency signals conforming to any known or future developed wireless protocol, for example, CDMA, GSM, EDGE, 3G, IEEE 802.x (e.g., IEEE 802.16 (WiMAX)), etc. The information transmitted over-the-air by the base station systems and the cellular communication towers to the portable fitness monitoring device 102 may be further transmitted to or received from one or more additional circuit-switched or packet-switched communication networks, including, for example, the Internet.

As shown in FIG. 2, communication may also occur between the personal computer 114 and a server 112 via a network 110. In an embodiment, the network 110 is the Internet. The Internet is a worldwide collection of servers, routers, switches and transmission lines that employ the Internet Protocol (TCP/IP) to communicate data. As indicated above, the Internet may also be employed for communication between the portable fitness monitoring device 102 and the personal computer 114. In one embodiment of the present invention, information may be directly communicated between the portable fitness monitoring device 102 and the server 112 via the network 110, thus bypassing the personal computer 114.

According to embodiments of the fitness monitoring service of the present invention, a wide variety of information may be communicated between any of the athlete 100, the personal fitness monitoring device 102, the personal computer 114, the network 110, and the server 112. Such information may include, for example, performance parameters, training advice, training plans, calendar data, route information, music, videos, text, images, voice communications, settings, software, and firmware.

Communication among the various elements of the present invention may occur before a physical activity is commenced, after a physical activity has been completed, and/or in real time during the physical activity. In addition, the interaction between, for example, the personal fitness monitoring device 102 and the personal computer 114, and the interaction between the personal computer 114 and the server 112 may occur at different times.

Information communicated to and stored by the server 112 may be accessible to the athlete 100 at a later time via the network 110. For example, the athlete could access post-activity performance information communicated to the server 112 from their personal fitness monitoring device 102 at a later time from their personal computer. In another embodiment of the present invention, a third party (e.g. a trainer, coach, friend, or family member) stationed at a personal computer 114 may be able to access real-time or historical performance information regarding the athlete's performance via the server 112 over the network 110.

Figure 3:
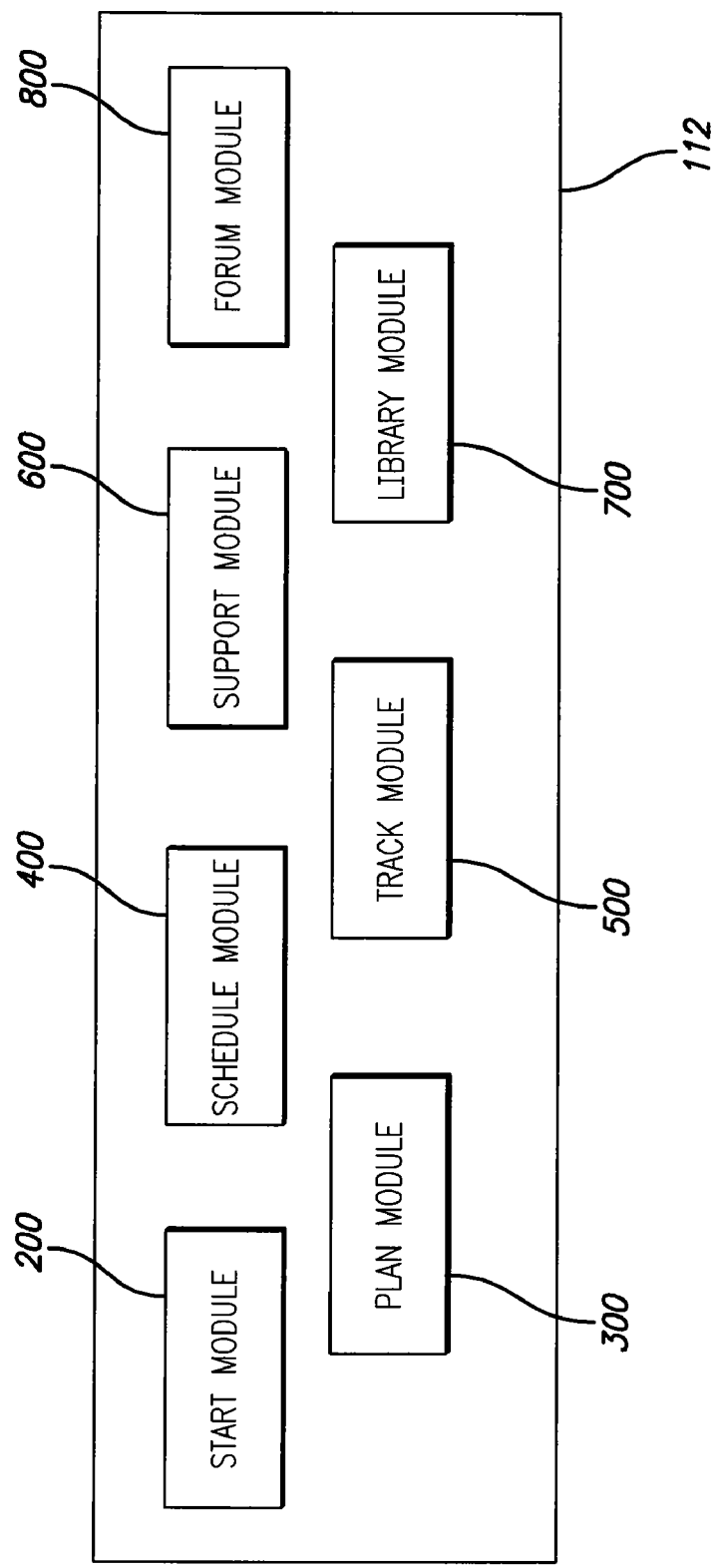
FIG. 3 is a block diagram of an exemplary software configuration of a server according to an embodiment of the present invention.

FIG. 3 is a diagram of an exemplary software configuration of server 112. The application software of server 112 includes a number of different modules capable of providing fitness monitoring services to athletes 100. In one embodiment of the present invention, these modules include a start module 200, and plan module 300, a schedule module 400, a track module 500, a support module 600, a library module 700, and a forum module 800. Each module supports one or more graphical user interfaces (GUIs) capable of being presented to users at one or more remote personal computers 114.

As is known by those of skill in the art, a GUI may use a combination of technologies and devices to provide a platform the user 100 can interact with via a computer 114. A GUI may offer, for example, graphical elements, visual indicators, and text to represent information and actions available to the user 100. Graphical elements may include, for example, windows, menus, radio buttons, check boxes, and icons. The user 100 may use a physical input device, such as a mouse, to control the position of a cursor 206 on their computer 114 screen.

Those skilled in the art will appreciate that alternative or additional modules and sub-modules may be implemented within the server 112 system in order to provide or extend the described or additional functionalities. For example, the software configuration of server 112 may include an operating system, which may be one of the commercially available operating systems such as, for example, Windows, UNIX, LINUX, Mac OSX, or AIX. The operating system may also have an associated application programming interface through which middleware and application programs may access the services of the operating system. In addition, a hypertext transport protocol (HTTP) server may run on top of the operating system. As is well known in the art, HTTP server may communicate data over the Internet using HTTP.

Figure 4:
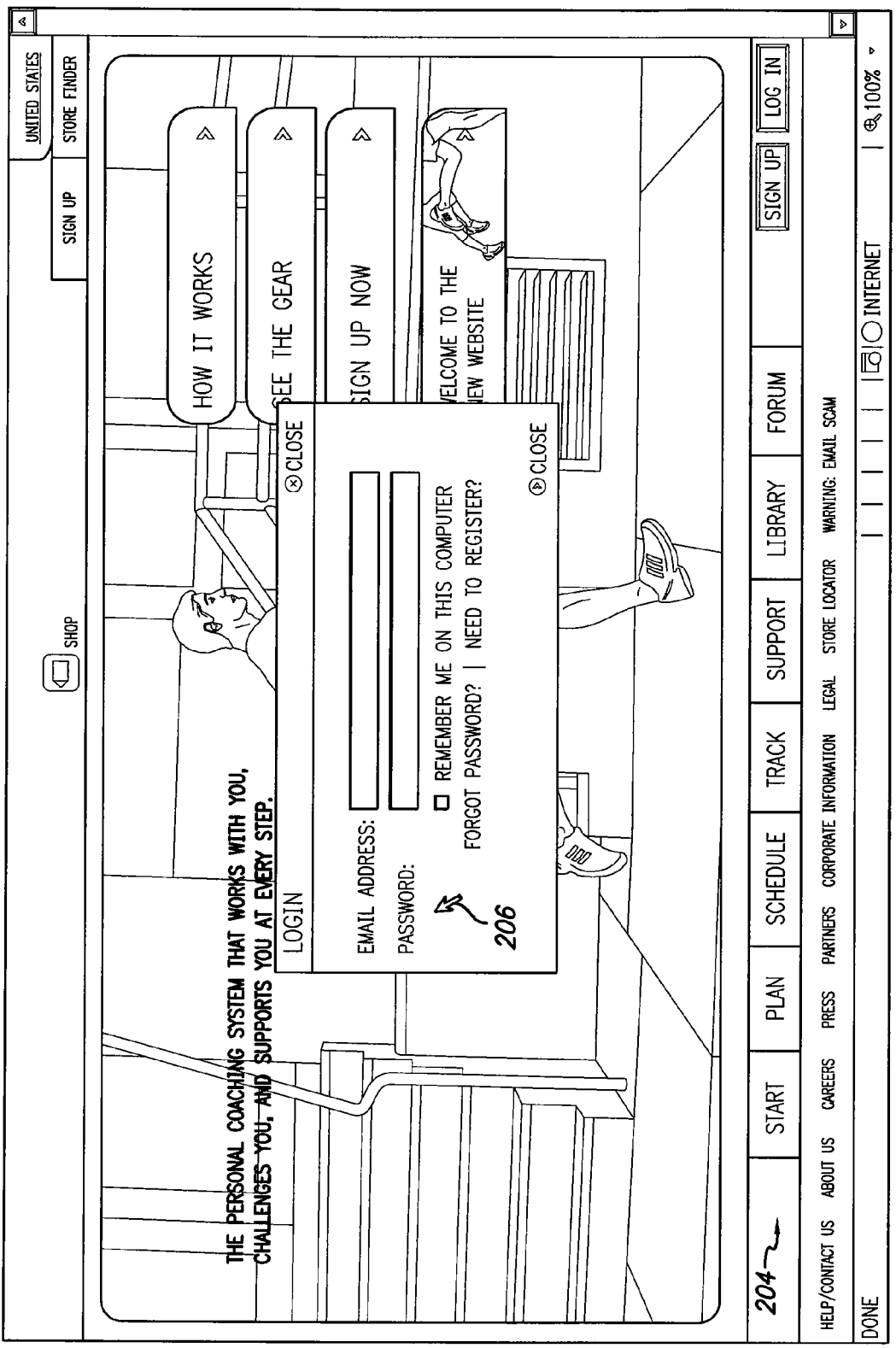
FIG. 4 is an exemplary GUI window according to an embodiment of the present invention.

According to one embodiment of the present invention, FIG. 4 illustrates a GUI window presented by start module 200 to a user of a remote personal computer 114 system.

As illustrated by FIGS. 4-7, 9-37, and 39-47, the various modules of the fitness monitoring service of the present invention may support GUIs through which a user 100 can interact with the fitness monitoring service. As will be appreciated by those of skill in the art, in one embodiment the GUIs may appear as webpages provided by a server 112 via a website that may be accessible to the user over the Internet 110 using a web browser on their computer 114. In other embodiments, the GUIs may be generated by a processor based only on information stored on the personal computer 114, a CD-ROM, a mobile phone, or other computer readable media accessible locally to the user 100. In embodiments of the present invention, users 100 can, among other things, use data generated from past performances to gauge their improvement, set goals for the future, share their performance data with others, and/or assist themselves in exercising at intensities appropriate for their current fitness level and goals.

With reference to FIG. 4, a menu bar 204 may be present near one of the edges of a GUI window of the present invention. The menu bar 204 may include several icons or indicia corresponding to the start 200, plan 300, schedule 400, track 500, support 600, library 700, and forum 800 modules. In one embodiment, the menu bar 204 may be present on every GUI page presented to the user by the server. After logging in to the server 112, the user 100 may be able to navigate to areas of the website supported by different modules by selecting their corresponding icons with a cursor 206. Additional icons corresponding to sub-modules or program wizards associated with a particular module may pop up or otherwise be displayed to the user 100 if the user 100 selects or hovers the cursor 206 over a module icon.

In order to access the features of embodiments of the present invention, a user 100 stationed at a remote personal computer 114 may log into the server 112 via the internet 110. As is well known to those skilled in the art, the login process, which may be controlled by a log in wizard 202 run by start module 200, typically includes the entry by the remote user 100 of a login ID and password or other authentication information to the server 112, which then authenticates the identity of the user 100 by reference to a user database or the like. Embodiments of the fitness monitoring services of the present invention may be offered to a plurality of athletes 100 or other users 100 forming a user community, may be restricted to users 100 that have been issued login IDs and passwords for accessing the server 112, and/or may further be offered in exchange for a subscription fee.

Figure 5:
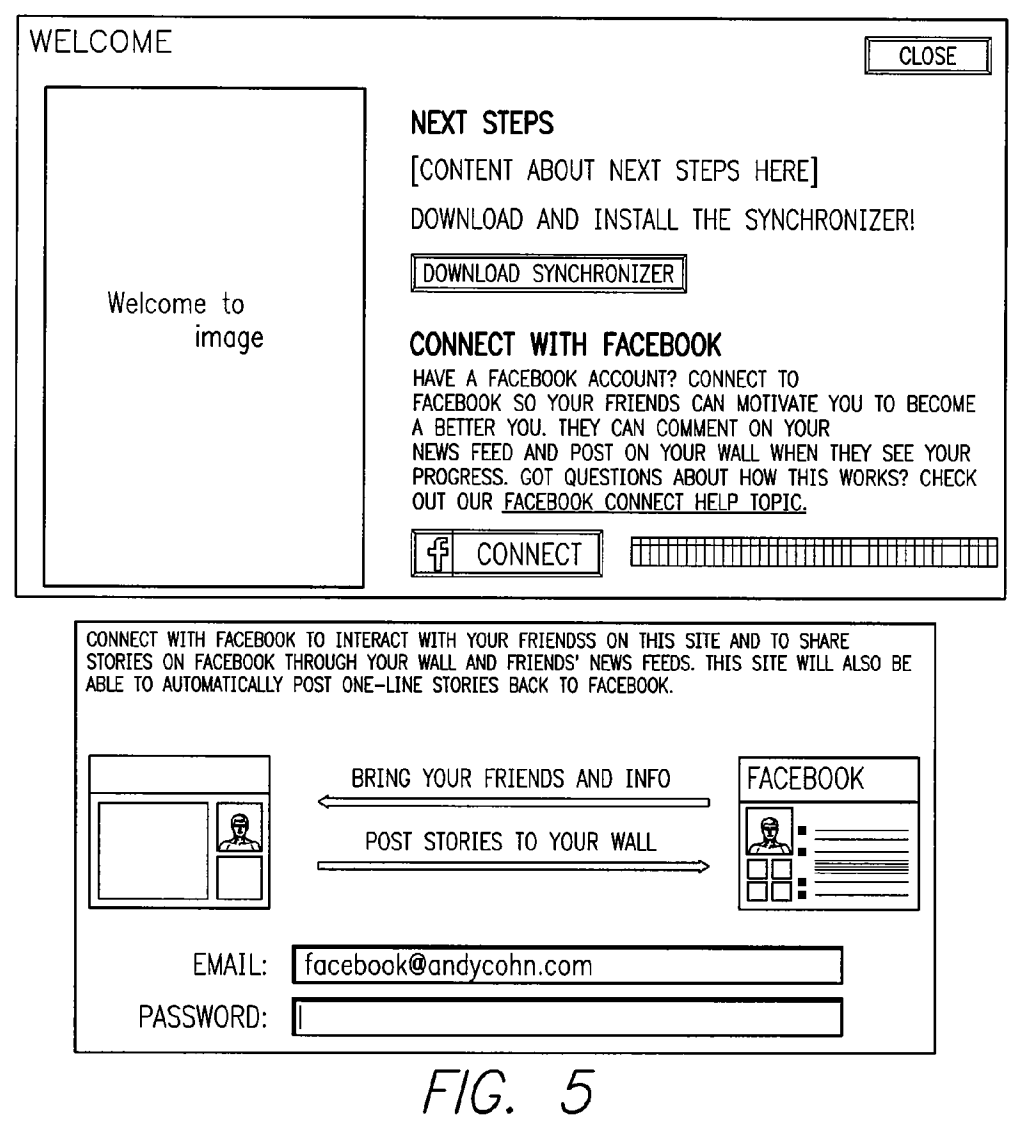
Figure 6:
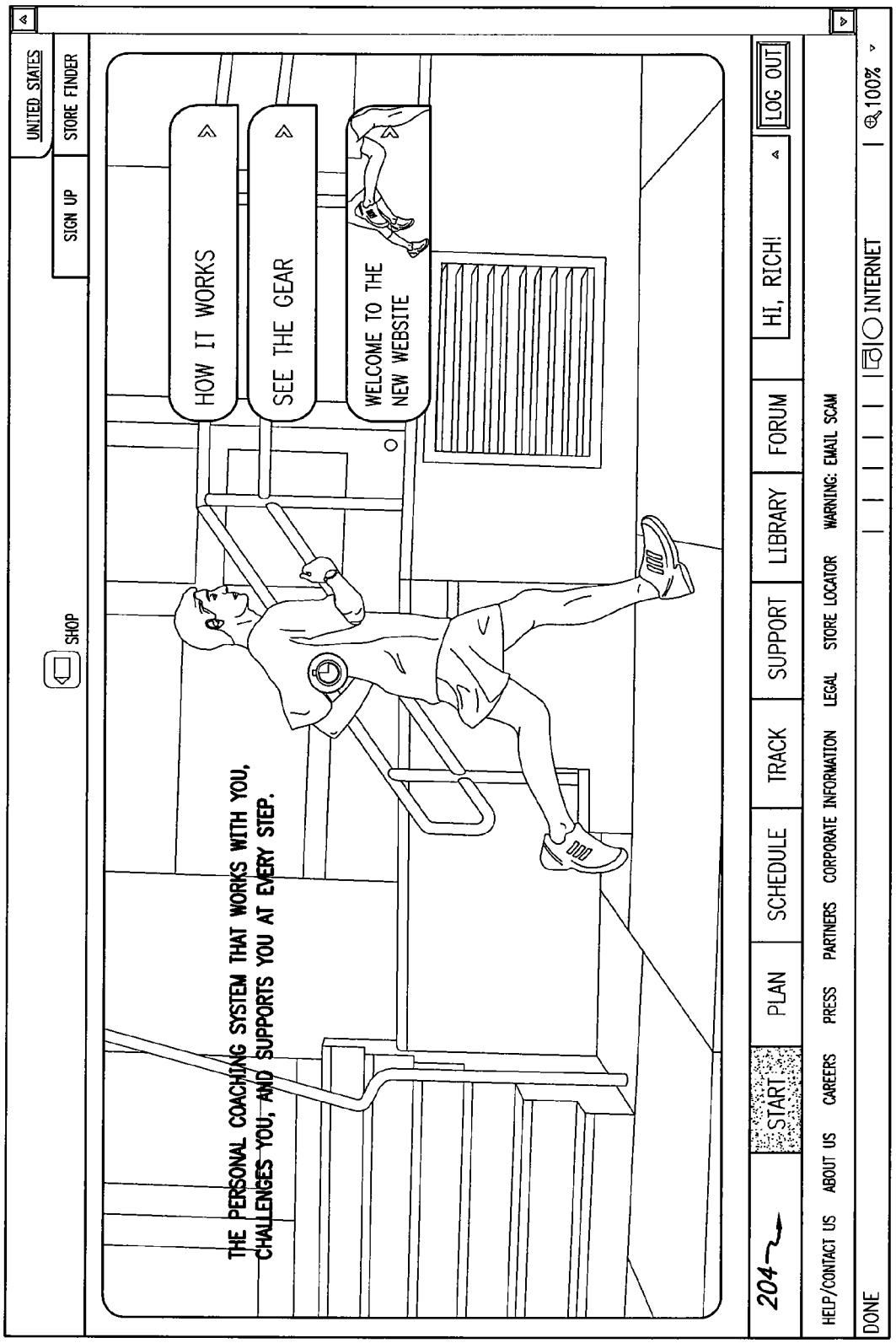
FIG. 6 is an exemplary GUI window according to an embodiment of the present invention.

Following the preliminary authentication process via the log in wizard 202, as illustrated in FIG. 5, a social networking wizard 208 run by the start module 200 may invite the user to link their fitness monitoring account to a social networking site, such as, for example, Facebook, MySpace, Twitter, Friendster, LinkedIn, or the like. As explained in further detail below, linking to a social networking site may provide the user 100 with added benefits and features. If the user declines the initial opportunity to link to a social networking site, they may be able to create such a link at a later time. Upon completion of the social networking wizard 208, start module 200 may present a home page, as illustrated in FIG. 6.

In an embodiment, the user 100 stationed at a remote personal computer 114 may alternatively choose to interact with the server 112 via a software widget. As is known by those of skill in the art, a software widget is a software application including portable code intended for one or more different software platforms. The term "software widget" implies that either the application, user interface, or both, may be relatively simple and easy to use, as exemplified by a desk accessory or applet.

In one embodiment, the software widget may be a desktop widget that is a specialized GUI widget intended to run on a computer desktop. In another embodiment, the software widget may be a mobile widget that can operate on mobile devices (e.g. smart phones). The widget may present a simplified version of the user interfaces explained in further detail herein, and may provide alternative means for the user to log in to the server 112. The widget may allow the user to review summary information about their past performance, and may allow the user to view, for example, a calendar of upcoming workouts, as described in further detail below.

From the home page, the user 100 may be able to navigate to different modules, sub-modules, or wizards by selecting their corresponding icons from the menu bar 204 with the cursor 206. In one embodiment, by hovering the cursor 206 over the start module 200 icon, the user 100 may be able to select an introductory sub-module 210, an equipment sub-module 212, or a device download sub-module 214.

Figure 7:
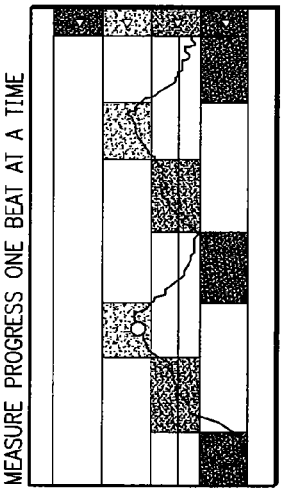
FIG. 7 is an exemplary GUI window according to an embodiment of the present invention.

FIG. 7 is an exemplary GUI window that may be displayed by the introductory sub-module 210. The introductory page may contain general information about the fitness monitoring system of the present invention, including a brief description of the system, its intended users, and the potential benefits available to those users.

For example, the introductory page may contain information about the planning, scheduling, and tracking capabilities of the fitness monitoring system. In one embodiment of the present invention, some aspects of the planning, scheduling, and tracking functions may be tied to a color-coded heart rate zone system. In other embodiments, some aspects of the planning, scheduling, and tracking functions may be tied to color-coded zone systems based on zones of other parameters including, but not limited to, speed, pace, stride rate, calories, respiration rate, blood oxygen level, blood flow, hydration status, or body temperature. A graphical representation and a brief description of such a color-coded system may be provided on the introductory page and in personal settings, as illustrated in FIG. 7.

In an embodiment of the present invention, the color of certain graphical information provided by the server 112 via the various GUIs presented may be dictated by detected or targeted heart rate information. Various modules of the fitness monitoring service of the present invention may be programmed with algorithms for establishing one or more heart rate ranges or "zones." Each zone may be associated with a particular color. Zones may be defined, for example, as ranges of percentages of an athlete's 100 maximum heart rate. Accordingly, each zone may be associated with a particular level of effort.

FIG. 8 is an exemplary illustration of the zone definitions according to one embodiment of the present invention. An energy zone, ranging from 65% to 75% of an athlete's 100 maximum heart rate, is associated with the color blue. An endurance zone, ranging from 75% to 85% of an athlete's 100 maximum heart rate, is associated with the color green. A strength zone, ranging from 85% to 90% of an athlete's 100 maximum heart rate, is associated with the color yellow. Finally, a power zone, ranging from 90% to 95% of an athlete's 100 maximum heart rate, is associated with the color red. These ranges and color combinations are exemplary only; numerous other ranges and/or colors could be used.

In an embodiment, an additional zone (for example, a pink zone) may also be provided that overlaps the ranges of the blue, green, and yellow zones. The pink zone may primarily be used for setting intensity goals for beginners. In a further embodiment, the colors may change in character from relatively light or dim colors to relatively dark or intense colors as values associated with the zone colors increase from the lower to upper limits of the zone.

The zones may be assigned based on predetermined fitness goals. For example, in the embodiment of FIG. 8, the energy zone (blue) may be associated with a heart rate range that allows an athlete 100 to build their aerobic base. The endurance zone (green) may be associated with a heart rate range that allows an athlete 100 to build cardiovascular strength and burn calories. The strength zone (yellow) may be associated with a heart rate range that allows an athlete 100 to improve their aerobic threshold, endurance, and metabolism. The power zone (red) may be associated with a heart rate range that allows an athlete 100 to improve their anaerobic threshold, endurance, and metabolism.

For planning purposes, that zones can be presented to the user 100 as an indication of the difficulty of a particular workout. For monitoring and tracking purposes, the zones may be established for a particular user 100 based on a maximum heart rate. An athlete's 100 maximum heart rate may not be an indication of their fitness level, it usually may not change significantly with training, and it may be set by the athlete's 100 genetics. An athlete's 100 maximum heart rate can be provided to the fitness monitoring service of the present invention in a number of ways.

Returning to the functionality of the start module 200, FIG. 9 is an exemplary GUI window that may be displayed by the equipment sub-module 212. The equipment page may contain an overview of the different pieces of equipment that are compatible with the fitness monitoring system of the present invention. Such pieces of equipment may include, for example, mobile fitness phones, dedicated portable fitness monitoring devices, non-dedicated portable fitness monitoring devices, sports mode-enabled MP3 players, sports mode-enabled dongles, sports watches, display devices, exercise machines in fitness centers, and sensors (e.g. pedometers or heart rate sensors). A broad overview of each piece of equipment and/or more detailed specifications may be provided. A table or interactive equipment wizard 216 may further be provided to help the athlete 100 select the equipment that best suits the athlete's 100 needs and fitness goals.

The equipment wizard 216 may pose a series of questions to the athlete 100 or the athlete's 100 coach such as, for example, "What are your personal fitness goals?", "Do you already have a dedicated portable fitness monitoring device?", "Do you want to receive performance feedback and/or coaching during your activity?", "Do you want to log performance data during your activity?", "Would you like to be able to listen to music during your activity?", "Would you like to monitor your heart rate?", "Would you like to monitor your speed?", "Would you like to use GPS-enabled features?", and "Would you like to be able to transmit and receive data to and from your device in real-time?". Other interactive questions for determining and/or fulfilling the needs of the user 100 may be included.

The equipment page provided by the equipment sub-module 212 may further prompt or allow user's 100 to purchase the equipment through the equipment page, may provide links to other websites where the user 100 could purchase the equipment, and/or may provide information about physical retail outlets where the user 100 could purchase the equipment.

Figure 10:
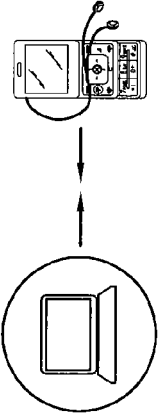
FIG. 10 is an exemplary GUI window according to an embodiment of the present invention.

FIG. 10 is an exemplary GUI window that may be displayed by the device download sub-module 214. The device download page may contain software and firmware downloads and or updates for users 100. For example, a synchronizer program could be downloaded to a user's 100 personal computer 114 that could manage communications between the portable fitness monitoring device 102 and the personal computer 114. The user 100 could activate the synchronizer program while using their personal computer 114, and utilize it to transfer software and firmware updates to the portable fitness monitoring device 102 or to update settings or options on the portable fitness monitoring device 102. Like the application software of the server 112, the synchronizer program running on the user's 100 personal computer 114 could also support one or more GUIs capable of being presented to the user 100 at the computer 114. Thus, the user 100 may be able to, among other things, update settings or options on the portable fitness monitoring device 102 without being connected to the server 112 via the network 110. In embodiments of the present invention, portable fitness monitoring device 102 settings and options may also be adjustable directly via the portable fitness monitoring device 102 itself, depending on its particular configuration.

As indicated above, in embodiments of the present invention, the menu bar 204 may be present on every GUI page presented to the user by the server 112. Accordingly, at any time, the user 100 may be able to navigate to portions of the website supported by different modules, sub-modules, or wizards by selecting their corresponding icons from the menu bar 204 with the cursor 206. In one embodiment, the user 100 may be able to select an icon corresponding to the plan module 300 from the menu bar 204.

Figure 11:
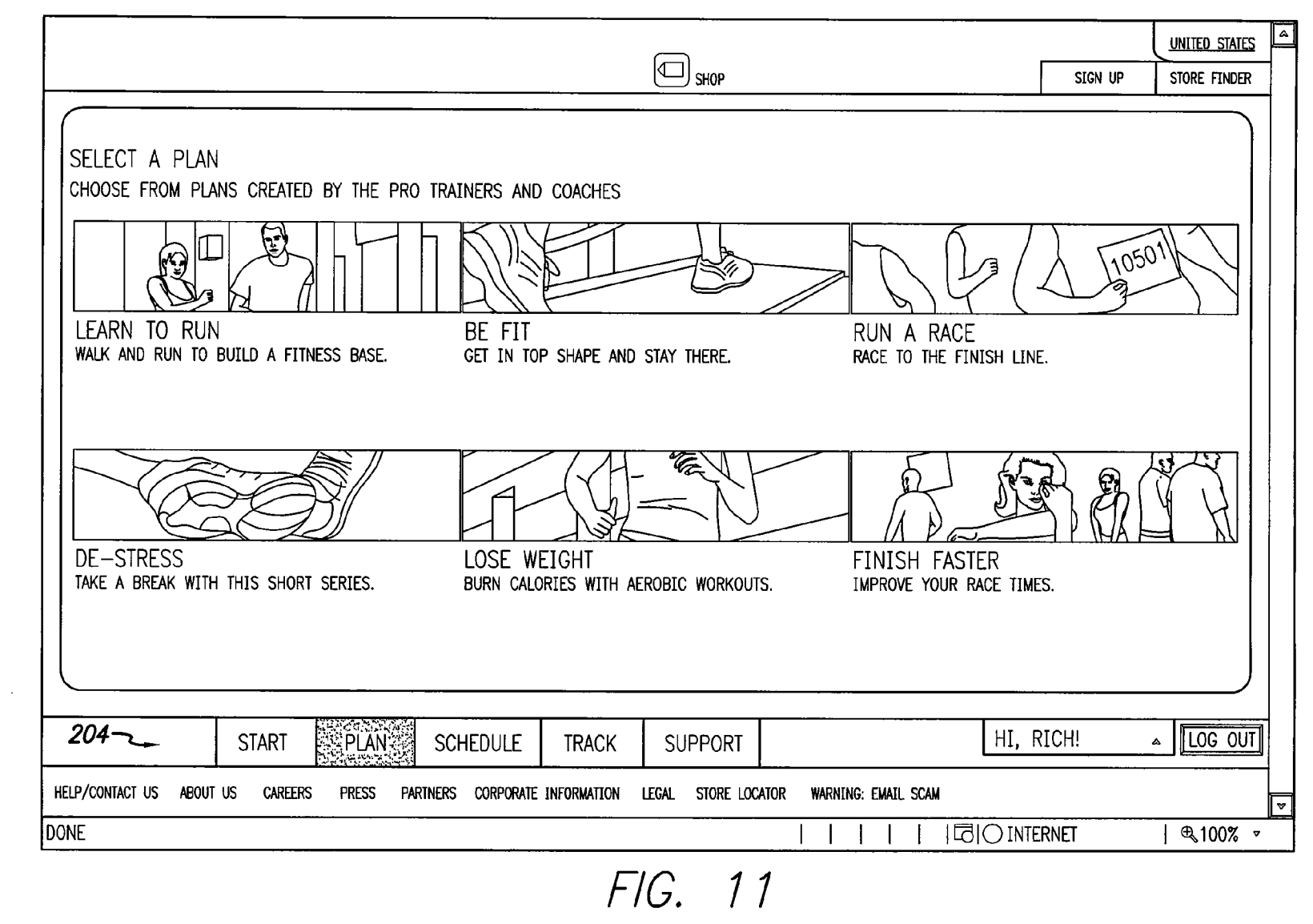

FIG. 11 is an exemplary GUI window that may be displayed by the plan module 300. From the main plan module page, the user 100 may be able to select from one of a plurality of icons corresponding to training plans. Additional icons corresponding to training sub-plans may pop up or otherwise be displayed to the user 100 if the user 100 selects or hovers the cursor 206 over a training plan icon.

In one embodiment of the present invention, from the main plan page, the plan module 300 may enable the user 100 to select training plan icons with the cursor 206 associated with various training plan sub-modules, such as, for example, a Learn to Run sub-module 302, a Be Fit sub-module 304, a Run a Race sub-module 306, a De-Stress sub-module 308, a Lose Weight sub-module 310, and a Finish Faster sub-module 312.

FIGS. 12-17 are exemplary GUI windows that may be displayed by the various plan module 300 sub-modules 302-312. Each plan module 300 sub-module may be associated with a different training plan having a different intended athlete user 100 audience and different goals. For example, the Learn to Run sub-module 302 may provide a plan where the beginner athlete 100 walks and runs at relatively easy paces in order to build their fitness base. An athlete 100 utilizing the Learn to Run program may be encouraged to master the basics of heart rate training, improve their running form, and/or learn to enjoy running.

The Be Fit sub-module 304 may provide a plan where the athlete 100 runs at slightly faster paces in order to improve their overall physical fitness. An athlete 100 utilizing the Be Fit program may be encouraged to, for example, increase their cardiovascular capacity and conduct interval training (i.e. sequentially running at different intensities for different periods of time or for different distances).

One or more of the plan module 300 sub-modules may also be designed for athletes 100 who are interested in physical activities besides—or in addition to—running. For example, the Be Fit sub-module 304 may also provide a plan where the athlete 100 works out in a gym using various machines and pieces of stationary exercise equipment to improve their overall physical fitness. An athlete 100 utilizing the Be Fit program may be encouraged to, for example, increase their cardiovascular capacity and conduct interval training on various machines and pieces of stationary exercise equipment.

The Run a Race sub-module 306 may provide a plan for athletes 100 interested in preparing for a race. In one embodiment of the invention, the Run a Race sub-module 306 may provide a plurality of different plans depending on the distance of the race the athlete 100 is planning to participate in. Plans may be provided, for example, for 5K, 10K, ½ marathon, and full marathon races. An athlete 100 utilizing one of the Run a Race programs may be encouraged to, for example, conduct interval or other speed work training, take long runs and recovery runs, and generally build their endurance and aerobic capacity so that they are able to successfully complete their race.

The De-Stress sub-module 308 may provide a plan where the user's 100 primary goal may be to reduce their overall stress, achieve relaxation, and increase energy. A user 100 participating in the De-Stress program may, for example, be guided through a series of workouts of varying intensities that are regularly scheduled, but of relatively short duration, so that the user 100 is able to de-stress on a regular basis yet will still be able to find time in their schedule to complete their workouts.

The Lose Weight sub-module 310 may provide a plan for users 100 interested in burning calories, reducing body fat, increasing energy, and improving overall health through aerobic workouts. Again, the particular physical activities performed by the user 100 are not limited. A user 100 participating in the Lose Weight program may, for example, be guided through a consistent workout schedule that starts at a relatively easy level to build the user's 100 athletic base and establish a regular routine, and that may gradually progress to more difficult workouts.

Like the Run a Race sub-module 306, the Finish Faster sub-module 312 may provide a plan for athletes 100 interested in preparing for a race. However, the finish faster module 312 may be more appropriate for athletes 100 who have significant race experience and are looking to improve upon their past race times. An athlete 100 participating in the Finish Faster program may be encouraged to conduct interval training and speed work, and push themselves to the limit by conducting longer and more intense workouts.

In another embodiment of the present invention, a Recover sub-module may provide a plan for users who need to recover from a difficult race (e.g. a marathon), from an injury, or from any other physically, mentally, or emotionally taxing event. An athlete 100 participating in the Recover program may be given different goals depending on the specific situation. Athletes 100 recovering from a difficult race may only need a short series of relatively easy recovery runs to get their legs back for resumed training. Athletes recovering from an injury may need a much longer recovery period, depending on the severity of the injury. Athletes recovering from mentally or emotionally taxing events may be provided with a variety of goals, some of which may be similar to those provided in a De-Stress plan.

FIGS. 12-17 are exemplary GUI windows that may be displayed by the various plan module 300 sub-modules 302-312. Each plan sub-module page may include a description of the plan, including its intended athletic users 100 and its goals. Each plan sub-module page may further include a level selector 314 and a plan preview 316. The particular information displayed by the plan preview 316 may depend on a level selected via the level selector 314.

When considering the selection of a particular training plan, the associated plan sub-module may allow the user 100 to select from a plurality of difficulty levels for their prospective program using the level selector 314. The level selector 314 may be an icon, a drop down menu, a slider, or any other GUI input device known in the art. In one embodiment, the user 100 may be able to choose from one of seven difficulty levels, where level 1 is the easiest and level 7 is the most difficult level.

In another embodiment, the user's 100 difficulty level options may be limited based on the particular training plan sub-module selected. For example, as illustrated in FIG. 12, the Learn to Run sub-module 302 may only be capable of presenting levels 1 through 3. Because a user 100 who is just learning to run or begin an exercising is not likely to desire a program of high difficulty, such a limitation may be appropriate. On the other hand, as illustrated in FIG. 17, the Finish Faster sub-module 312 may only be capable of presenting levels 6 and 7. Because a user 100 who has participated in several competitive races before has likely achieved a high level of physical fitness, such a limitation may also be appropriate.

In one embodiment, the user's 100 difficulty level options may be limited based on the particular training plan sub-module selected because of certain filters in place. In an embodiment, the user 100 may be able to deactivate or modify these filters in order to be able to choose from a wider variety of levels for a given plan. Alternatively, such filters may not be present, and a user 100 may be free to chose any level for any plan.

Once a difficulty level for a prospective plan has been selected via level selector 314, the particular training plan sub-module provides the plan preview 316 for the plan. The plan preview 316 may include a description of what to expect from the plan, a description of the benefits of the plan, and/or a sample schedule. The plan description may make reference to the particular color-coded heart rate zones that a user 100 may be prompted to exercise at as part of that plan. As illustrated in FIGS. 12-17, the sample schedule may include an indication of the number of total workouts in the plan, the number of workouts per week, and the total number of weeks.

Figure 18:
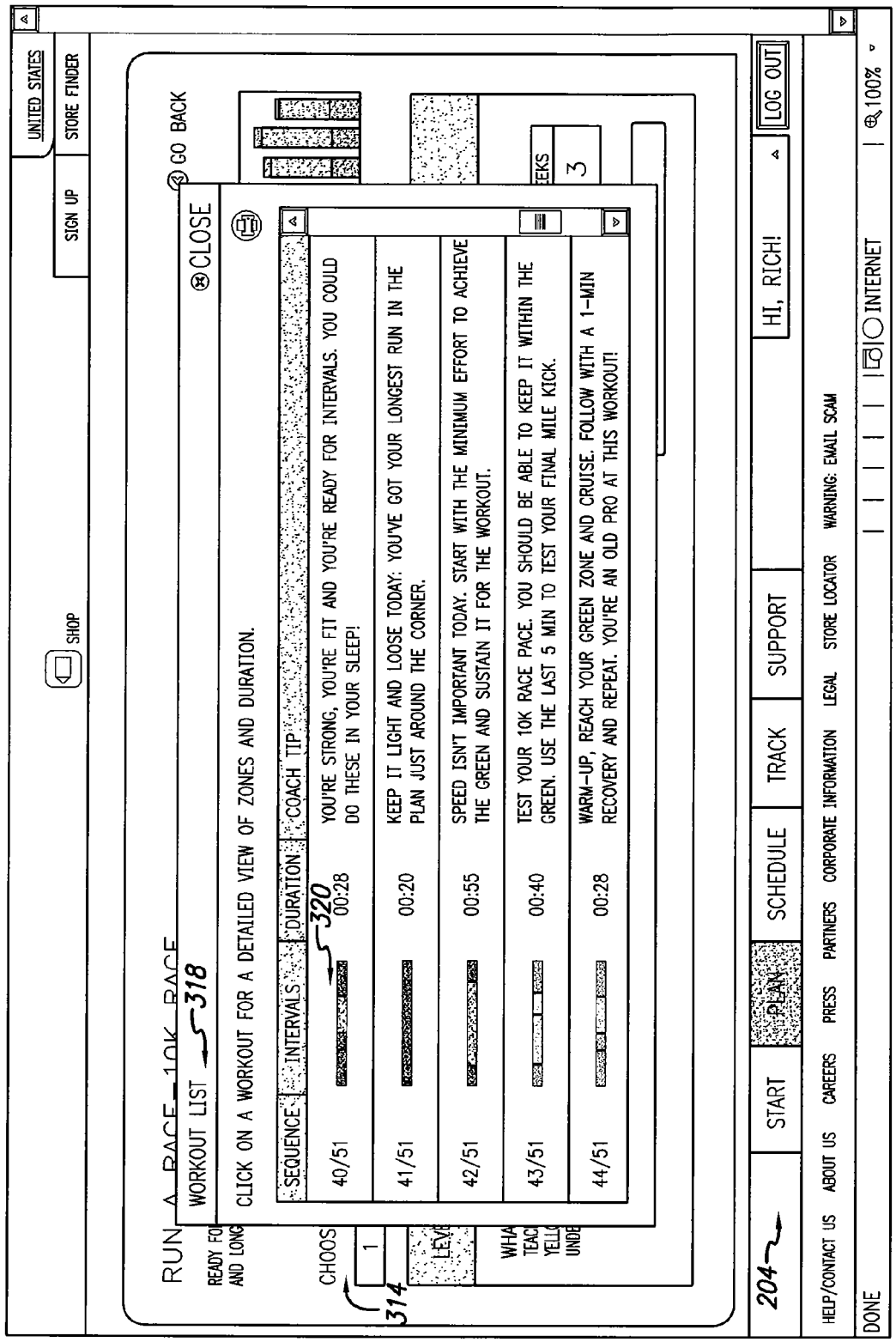
FIG. 18 is an exemplary GUI window according to an embodiment of the present invention.

The training plan sub-module may also provide a sample workout list 318 for a given plan. The user 100 may access the sample workout list 318 by selecting an appropriate icon with their cursor 206. In one embodiment, the icon may be a bar graph representing the relative durations and intensities of the individual workouts of the plan. The durations of the individual workouts may be proportional to the length of the bars displayed, while the intensities of the individual workouts may be indicated by a color corresponding to the heart rate zone at which the user 100 will be instructed to exercise. FIG. 18 shows an exemplary GUI pop-up window providing the sample workout list 318 provided by the Run a Race sub-module 306 for a user 100 who has selected a level 4 10K race program.

In one embodiment, for each workout, the list 318 provides the workout number in the series (e.g. 40 of 51), a zone bar indicator 320, the workout duration, calories, or distance targeted (e.g. 28 minutes, 400 calories, or 5 kilometers), and a coaching tip. The zone bar indicator 320 may communicate several pieces of information. It may indicate the number of intervals to be performed. It may also indicate the relative intensities of each interval to be performed, based on a target heart rate zone, as indicated by a color. For example, as illustrated in FIG. 18, workout number 41 consists of one time interval of blue training (corresponding to, for example, an energy zone ranging from 65% to 75% of an athlete's 100 maximum heart rate). Workout 42 consists of three time intervals of training—a long interval of green training (corresponding to, for example, an endurance zone ranging from 75% to 85% of an athlete's 100 maximum heart rate) preceded and followed by short intervals of blue training. Workout 43 consists of four time intervals of training, including two blue intervals, a green interval, and a yellow interval (corresponding to, for example, a strength zone, ranging from 85% to 90% of an athlete's 100 maximum heart rate). In this way, the athlete 100 can gauge the relative level of difficulty and suitability of a prospective training plan by examining the zone bar indicators 320 associated with the individual workouts making up a prospective plan.

The coaching notes included in the workout list 318 may provide motivation, point out a particular area of focus, or otherwise provide guidance to the athlete 100 related to the ultimate goal of their particular plan.

After determining which plan best suits their needs, the athlete 100 may select an icon that enables plan module 300 to launch a plan personalization wizard 322. The questions presented by the plan personalization wizard 322 may vary depending on the type of plan selected. FIG. 19 shows an exemplary personalization wizard 322 GUI window provided by the Run a Race sub-module 306 for a user 100 who has selected a level 4 10K race program.

The plan personalization wizard 322 may prompt the user 100 to select a start date for their training plan, so that the plan may be built forward from that date. For users 100 who select a race-oriented plan (such as those provided by the Run a Race sub-module 306 or the Finish Faster sub-module 312), personalization wizard 322 may prompt the user 100 to select the day of their race, so that the plan may be built backward from the race date.

The plan personalization wizard 322 may also prompt the user 100 to select which days of the week they want to conduct their workouts on. For example, as illustrated in FIG. 19, a user 100 may choose to workout four days per week on Sundays, Tuesdays, Thursdays, and Saturdays. In other embodiments, users 100 may be able to plan workouts to occur on different days during different weeks.

While personalizing their plan, the user 100 may be able to vary the number of workouts per week by adding removing a workout day from their selection. In an embodiment, the system may then dynamically alter the total number of workout and total weeks of the workout plan, and display this information via the plan personalization wizard 322. Depending on the overall goals of the plan selected by the user 100, the system may or may not increase or decrease the total number of workout and/or the total number of weeks of the plan in response to the user 100 adding or removing a workout day from their schedule. For example, if a user 100 personalizes a plan to include workouts on only two days per week, the system may extend the plan over a longer period of time and/or add more total workouts. In contrast, if the user 100 personalizes a plan to include workouts on 6 days a week, the system may reduce the number of weeks of the plan and/or decrease the total number of workouts.

The plan personalization wizard 322 may further prompt the user 100 to give their plan a name. In one embodiment, the wizard 322 may provide a default name. In this way, a user 100 who wishes to schedule multiple training plans may be able to distinguish one plan from another by the plans' names.

In one embodiment, after the user 100 finalizes their plan via the personalization wizard 322, schedule module 400 may populate a GUI calendar 402 with the user's 100 plan. In addition, at any other time when the user 100 is logged in to the server 112, the user 100 may be able to navigate to the GUI calendar 402 by selecting the icon corresponding to the schedule module 400 from the menu bar 204.

Figure 20:
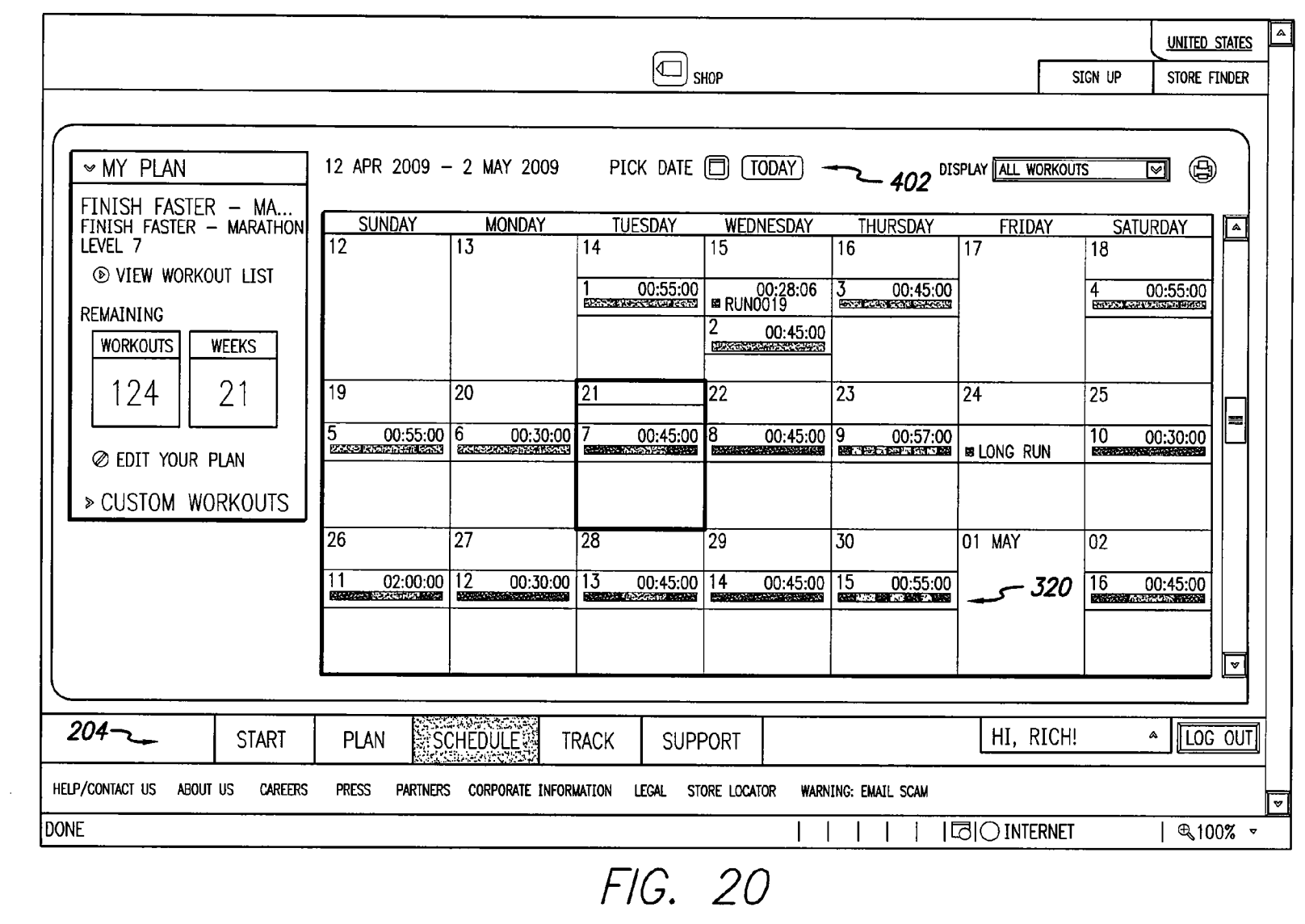

FIG. 20 is an exemplary GUI window according to an embodiment of the present invention containing the calendar 402 that may be displayed by the schedule module 400 for a user 100 who has selected a Finish Faster level 7 marathon race program. From the calendar 402 page, the user 100 may be able to view the individual workouts of their training plan populated throughout the calendar 402. The individual workouts populated into the calendar 402 may be represented by a zone bar indicator 320 similar to that provided by the plan module 300 via the sample workout list 318. The calendar 402 may also indicate the duration of each workout scheduled for each date. The GUI page containing the calendar 402 may also provide an indication of the number of workouts and/or number of weeks remaining for the current plan.

In one embodiment, the user may be able to access a workout list 318 containing a listing of all workouts of their currently selected plan by selecting an appropriate icon with their cursor 206. This workout list may be identical to one of the sample workout lists 318 provided by plan module 300.

The workout list is another way of presenting the workout information populated on to calendar 402.

From the calendar 402 page, the schedule module 400 may enable the user 100 to select icons with the cursor 206 associated with various schedule wizards, such as, for example, a plan editor wizard 404 and a custom workout wizard 406.

Figure 21:
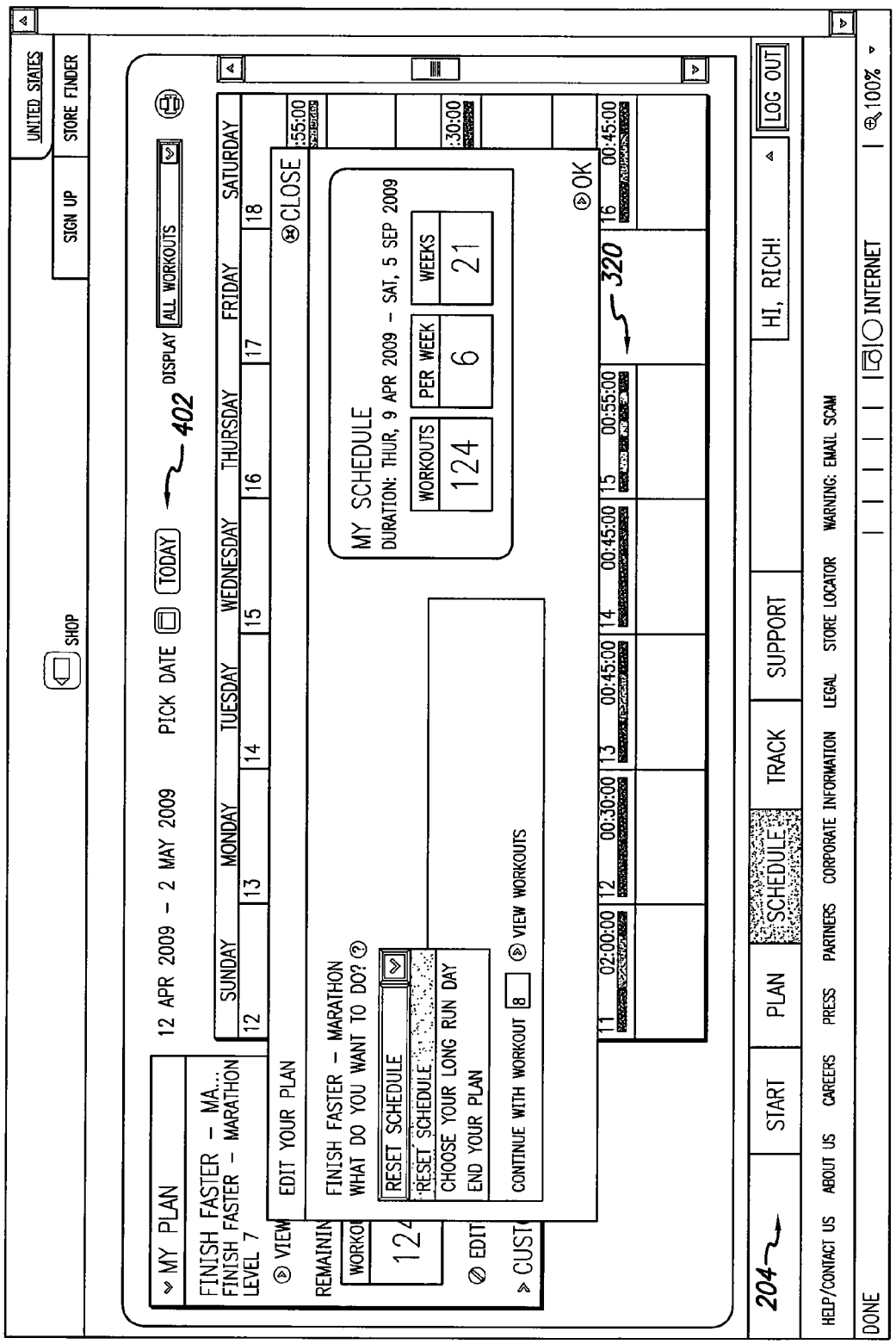
FIG. 21 is an exemplary GUI window according to an embodiment of the present invention.

FIG. 21 shows an exemplary plan editor wizard 404 GUI pop-up window, according to an embodiment of the present invention, that may be provided for a user 100 who has selected a Finish Faster level 7 marathon race program. The plan editor wizard 404 may allow the user 100 to, for example, reset their training schedule to start (or end) on a new date, choose a new day of the week for their long run, end their plan entirely, or adjust their schedule and calendar 402 to skip a given number of workouts in the plan.

Figure 22:
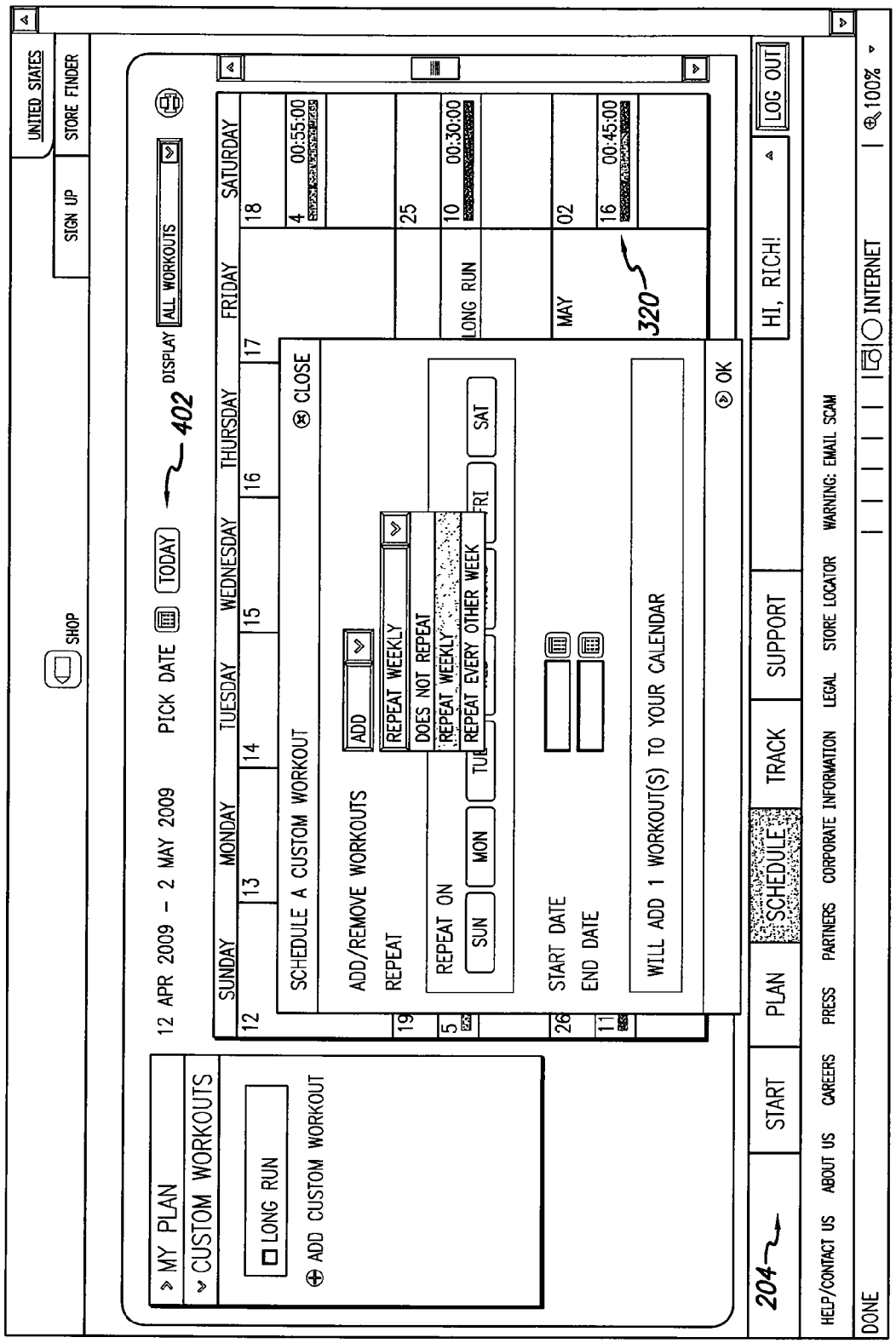
FIG. 22 is an exemplary GUI window according to an embodiment of the present invention.

FIG. 22 shows an exemplary custom workout wizard 406 GUI pop-up window, according to an embodiment of the present invention. The custom workout wizard 406 may allow a user to add workouts to their calendar 402 regardless of whether or not they are currently participating in a scheduled plan program. If a user 100 is participating in a scheduled plan program, the custom workout feature may be used to supplement the plan with additional workouts, remove workouts, or edit workouts as the user 100 desires. FIG. 22 shows an exemplary custom workout wizard 406 GUI pop-up window that may be provided for a user 100 who is already involved in a Finish Faster level 7 marathon race program. When a new workout is added, the wizard 406 may allow the user 100 to schedule the workout for a single date or schedule reoccurring instances of the workout on their calendar 402. For example, the user 100 could select to have the custom workout repeated weekly, or once every other week, on any day of the week. The user 100 may also be able to select a start and end date for any reoccurring workouts. The custom workout may also be named and saved. In one embodiment, while viewing the calendar 402 page, saved custom workouts may appear in a sidebar and the user 100 may drag and drop a custom workout into any date on the calendar 402 using their cursor 206.

In an embodiment, the custom workout created by the user may include one or more intervals of varying intensities according to the color-coded zone-based system described above. The custom workout wizard 406 may enable the user 100 to build an individual workout, for example, by assembling a series of zone intervals. The user may indicate the number of intervals to be performed and the relative intensities of each interval to be performed, based on a target heart rate zone (or other parameter-based zone), as indicated by a color. In one embodiment, the user 100 may assemble a custom workout with GUI elements that may resemble the graphical representation of the color-coded zone system as illustrated in FIG. 7. In an embodiment, the user 100 may originally be presented with a blank screen upon which they can drag, drop, stretch, or otherwise manipulate one or more colored boxes that represent intervals to be performed at specific intensities, as indicated by the color of the box. Stretching or shrinking the boxes may increase or decrease the duration of the interval associated with that box. In another embodiment, the user could numerically specify their desired number of intervals, their associated durations, and/or their associated intensities, and a GUI representation consisting of several colored boxes may automatically be produced. In an embodiment, the user 100 could specify a primary exercise interval and could click check boxes indicating that a warm-up and/or cool-down interval should also be inserted before or after their primary exercise interval, if desired. After a workout is finalized and saved, the workout built by the user 10 may be represented by a zone bar indicator 320, as described above.

In addition to creating customized individual workouts, in an embodiment, the user 10 may be able to create an entirely customized training plan from scratch. Via the plan module 400, the user 100 may be able to create an original plan by specifying, for example, the number of weeks, the number of workouts per week, and the characteristics of the individual workouts, as described with respect to the custom workout wizard above.

Once the athlete 100 has selected a training plan that has been populated onto the calendar 402, the athlete 100 may begin to engage in physical activities in accordance with the training plan. As illustrated in FIG. 1, the athlete 100 may be equipped with a portable fitness monitoring device 102. The portable fitness monitoring device 102 may be worn, carried, or otherwise supported by the athlete 100 during the physical activity. The portable fitness monitoring device 102 may also attach to a piece of exercise equipment such as a road bike traveling on a bike path or a stationary bike in the gym. The portable fitness monitoring device 102 may be capable of measuring and/or processing various performance parameters associated with the athlete's 100 physical activity. The portable fitness monitoring device 102 may communicate with one or more sensors 104, such as a heart rate sensor, for detecting the performance parameters. As discussed above with reference to FIG. 2, communication of performance parameters (such as heart rate or speed) may occur between two or more of the portable fitness monitoring device 102, the personal computer 114, and the server 112 via a network 110 (such as the Internet).

In an embodiment of the present invention, performance parameters for a plurality of athletes 100 may be stored on the server 112 and associated with particular user accounts by reference to a user database or the like. The track module 500 allows the users 100 to review and analyze their past performance data.

After completing a workout and uploading performance data to the server 112, the user 100 may log in to the server 112 to review and analyze their past performance data. In one embodiment, by hovering the cursor 206 over the track module 500 icon, the user may be able to select a workout journal sub-module 502 or a history sub-module 504. The user may also be provided with a link to view data from their latest workout via the history sub-module 504, as described in further detail, below.

FIG. 23 is an exemplary GUI window that may be displayed by the workout journal sub-module 502. In one embodiment, for each completed workout, the workout journal page may list the date the workout was completed, the name of the workout, and one or more performance details about the workout. For example, the workout journal page may list the elapsed time of the workout, the calories burned by the workout, the distance covered by the workout, the user's 100 average heart rate during the workout, the user's 100 average pace during the workout, the user's 100 average stride rate during the workout, a subjective user rating 506 of the workout and/or route, and any other notes 508 the user 100 wishes to record. The particular information displayed on the workout journal page may be set by the system or customized by the user 100. Various information columns may be added or removed by the user as desired.

In an embodiment, the workout journal sub-module 502 may provide a listing of all workouts completed by the user 100 using the portable fitness monitoring system. By default, the workouts may be listed in order by date. The user 100 may also be able to sort the displayed workout data by category. For example, if the user 100 wanted to sort all of their workouts by average heart rate, the user might click on the "heart rate" column header with the cursor 206, causing the workout journal sub-module 502 to sort the workout data accordingly. A user 100 may only want to view workouts from a specific date range. Accordingly, in one embodiment, the user 100 may be able to select a specific week, month, or year for which to view workout data. By selecting a particular listed workout with the cursor 206, the user 100 may be able to view more detailed data from that workout via the history sub-module 504, as described in further detail below, with respect to FIG. 27.

The subjective user rating 506 may be assigned by the user 100 immediately after the workout is completed, or at a later time. In one embodiment, the user 100 may rate a workout on a one to five star scale, with a one star workout being a poor workout and a five star workout being an excellent workout. In one embodiment, the user rating 506 may be entirely subjective. Alternatively, the user rating 506 may be assigned by track module 500 (or one of its sub-modules), based on various recorded performance parameters from the workout, historical user 100 performance, and/or user settings and options.

The user notes 508 may also be assigned by the user 100 immediately after the workout is complete or at a later time. User notes may include, for example, explanations of a user rating 506 assigned to the workout, or other subjective or objective observations about the workout, the user's 100 condition, the environment the workout was conducted in, or the route traversed.

In addition to (or in place of) being able to review and analyze past performance data via the workout journal sub-module 502, the user 100 may be able to select an icon capable of initiating the history sub-module 504. The history sub-module 504 may be capable of displaying a variety of GUI windows to the user such as, for example, those shown in FIGS. 24-35.

In one embodiment of the present invention, there may be overlap between the information displayed by the workout journal sub-module 502 and the history sub-module 504. The user 100 may prefer that information be displayed via one module for certain purposes and the other module for other purposes.

FIG. 24 is an exemplary GUI window according to an embodiment of the present invention that may be displayed by the history sub-module 504. History pages may include a dashboard 510, a primary display 512, and a sidebar 514. The dashboard 510 may provide icons that are correlated to particular performance parameters. Each icon itself may provide information about the performance parameters, and selecting a specific icon with the cursor 206 may alter the information displayed by the primary display 512. The sidebar 514 may provide additional information, icons, and/or options.

The information displayed on the history pages may be for a single workout or for a plurality of workouts falling within a particular date range. Information may be displayed on a yearly, monthly, weekly, or daily basis. The data range selected by the user 100 may affect the information displayed by the dashboard 510 icons, the information displayed on the primary display 512, as well as the content of the sidebar 514.

With reference to FIG. 24, for example, the user 100 may select and the history sub-module 504 may provide a history page displaying past performance information on a weekly basis from Jun. 29, 2008, through Sep. 20, 2008. The user 100 may have selected this date range by locating a workout in the workout journal display via workout journal sub-module 501, selecting that workout, and then selecting a weekly display via the history sub-module. Alternatively, the user 100 may have navigated directly to the history page via the history sub-module 504. A user 100 viewing a weekly history page may be able to move forward or backward in time to alter their display by selecting and dragging a scrollbar 516 with their cursor 206. The scrollbar 516 may be included, for example, within the primary display 512.

Figure 26:
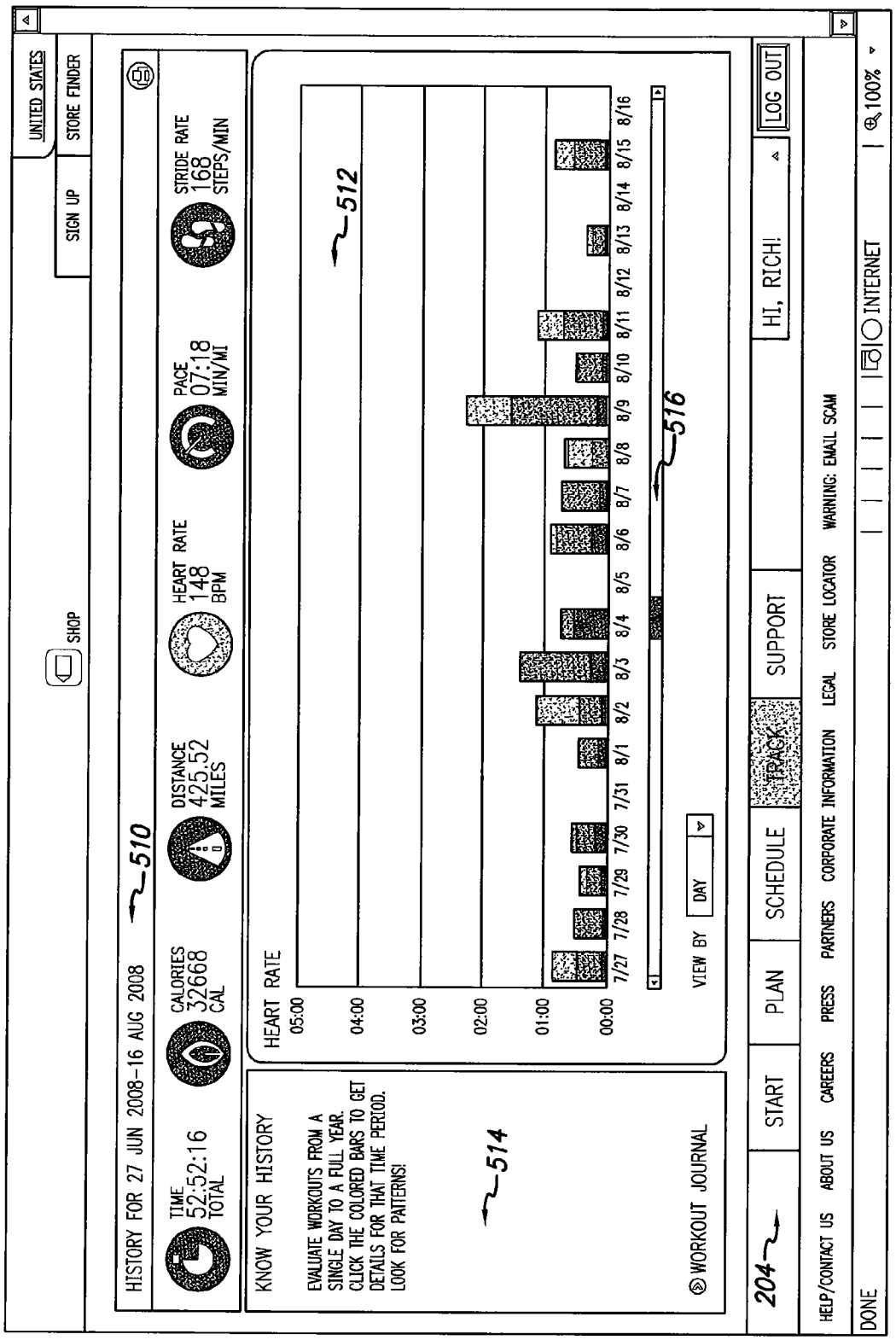
FIG. 26 is an exemplary GUI window according to an embodiment of the present invention.

The dashboard 510 shown in FIG. 26 includes display icons for time, calories, distance, heart rate, pace, and stride rate. The numerical information provided with the dashboard 510 icons corresponds to data associated with workouts from the date range selected. For example, as illustrated in FIG. 24, for the selected period of Jun. 29, 2008, through Sep. 20, 2008, the user's total workout time was 52 hours, 52 minutes, and 16 seconds. This value may also be provided in cumulative and/or average form over the selected time period.

Figure 25:
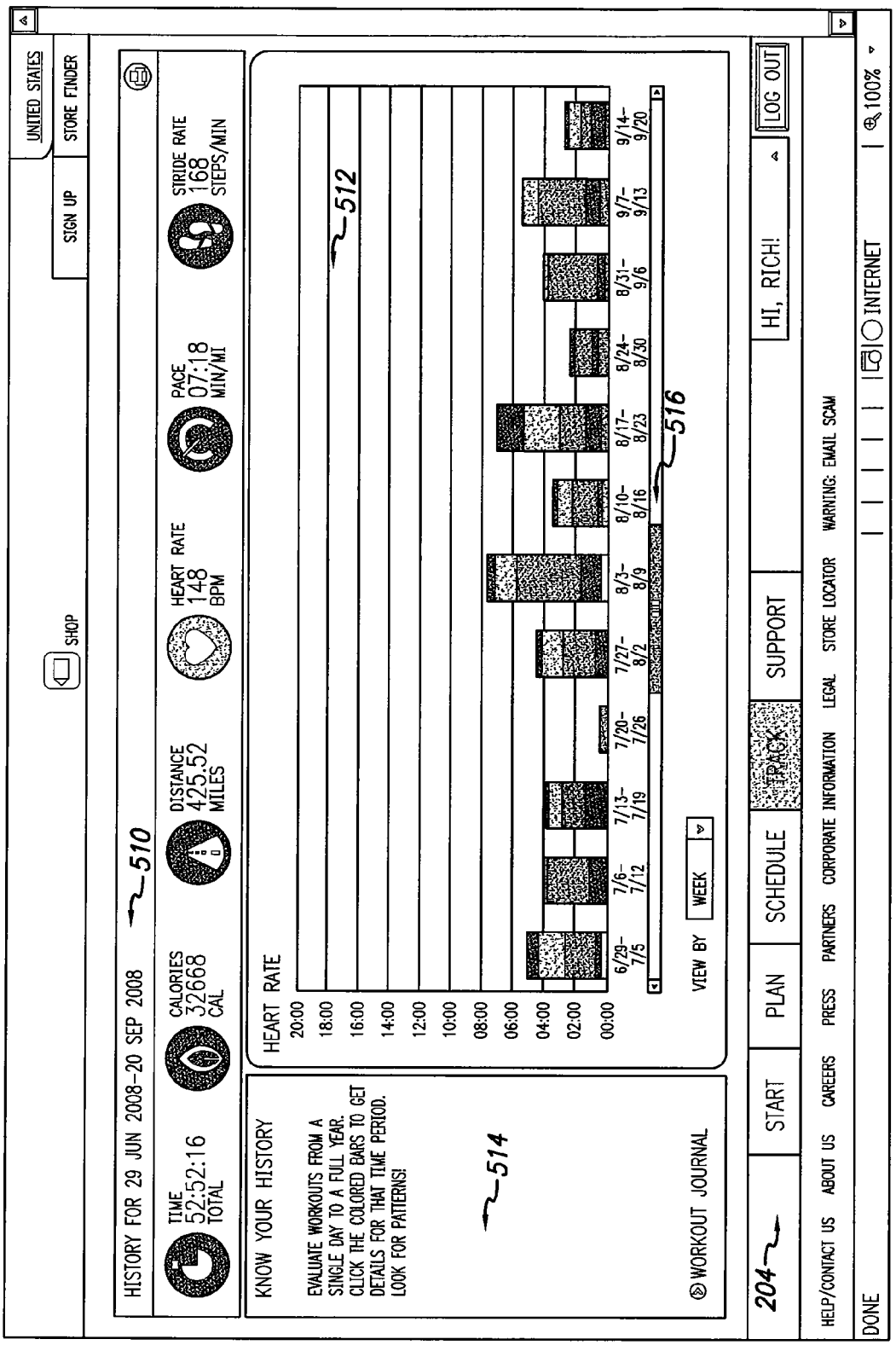
FIG. 25 is an exemplary GUI window according to an embodiment of the present invention.

While the information provided by the dashboard 510 icons may remain the same for a given date range, the information displayed by the primary display 512 may change depending on which dashboard 510 icon the user 100 has selected. For example, in FIG. 24, because the user 100 has selected the time icon in the dashboard 510, the history sub-module 504 displays time information in the primary display 512. In FIG. 25, because the user 100 has selected the heart rate icon in the dashboard 510, the history sub-module 504 displays heart rate information in the primary display 512. Note that in both FIGS. 24 and 25 the numerical information displayed by the dashboard 510 icons has not changed because the date range remains the same.

While the figures show the information displayed by the primary display 512 in the form of bar graphs, other suitable graphical displays such as, for example, line graphs, pie graphs, racecourse representations, animations, or videos may be provided in addition to or in place of the bar graphs. Moreover, although only time and heart rate graphs have been illustrated by the figures, any performance parameters listed in the dashboard 510 may be graphically displayed in the primary display 512.

As illustrated in FIG. 24, when a weekly display is selected, cumulative and/or average data for a plurality of weeks is displayed in the primary display 512. For example, for the selected period of Jun. 29, 2008, through Sep. 20, 2008, separate bars may be displayed for the weeks of June 29 through July 5, July 6 through July 12, July 13 through July 29, etc.

As shown in FIG. 25, when weekly heart rate information is displayed in the primary display 512 in bar graph form, the heart rate information may be conveyed based on the color-coded heart rate zone system described above with respect to FIGS. 7 and 8. Likewise, when weekly pace, stride rate, or other parameter information is displayed in the primary display 512 in bar graph form, the pace, stride rate, or other parameter information may be conveyed based on a color-coded zone system corresponding to these other parameters.

In one embodiment, as illustrated by FIG. 25, a color-coded bar may be provided for each week. The color-coded bar may include, for example, blue, green, yellow, and red regions associated with various heart rate zone ranges, as described above. The y-axis of the graph displayed in the primary display 512 may be time-based, and the total height of each weekly color-coded bar may correspond to the cumulative workout time for a weekly period. The relative heights of the individual color-coded regions within a given bar may be proportional to the amount of time the athlete 100 spent in that heart rate zone corresponding to each color for the weekly period.

For example, in the embodiment of FIG. 25, during the week of August 3 through August 9, the athlete 100 worked out for a time period of approximately eight hours and spent time working out in each of the four heart rate zones, but primarily worked out in the green heart rate zone.

An athlete 100 who wants to obtain more specific information about a period of time displayed within the primary display 512 may hover their cursor 206 over the appropriate graphic to display a GUI pop-up window containing such information. For example, for the weekly time display shown in FIG. 24, the athlete 100 has hovered their cursor 206 over the bar representing the week of July 13 through July 19. The displayed pop-up window may indicate the time, calories, distance, heart rate, pace, an/or stride rate information for only the specific week selected by the athlete 100. The particular information displayed in the pop-up window may be set by the system or customized by the user 100. Various information may be added or removed by the user as desired. Note that this information is taken from a smaller period of time than the information concurrently displayed in the dashboard 510.

In one embodiment, an athlete 100 who wishes to obtain more specific information about a period of time displayed within the primary display 512 may alternatively select the bar or other indicium representing the appropriate time period with their cursor 206 (e.g. by clicking on the bar or other indicium). For example, if the user 100 viewing the weekly GUI window of FIG. 25 wanted to obtain more specific information about the week of August 3 through August 9, the user 100 could select the bar representing that week, which may result in the history sub-module 504 displaying the daily GUI window shown in FIG. 26. The resulting window may show data for only the previously selected range (i.e. the week of August 3 through August 9), or it may show a slightly broader date range, as showing FIG. 26, which provides daily information from July 27 through August 16.

The history display shown in FIG. 26 is similar to that shown in FIG. 25 except that specific workout dates, as opposed to weeks, are displayed in the primary display 512. Accordingly, the cumulative and/or average information displayed in the dashboard 510 is also from a narrower date range.

An athlete 100 who wishes to obtain even more specific information about a period of time displayed within the primary display 512 may select the bar or other indicium representing the appropriate time period with their cursor 206 (e.g. by clicking on the bar or other indicium). For example, if the user 100 viewing the daily GUI window of FIG. 26 wanted to obtain more specific information about workouts conducted on Aug. 9, 2008, the user 100 could select the bar representing that day, which may result in the history sub-module 504 displaying the daily GUI window shown in FIG. 27.

Figure 27:
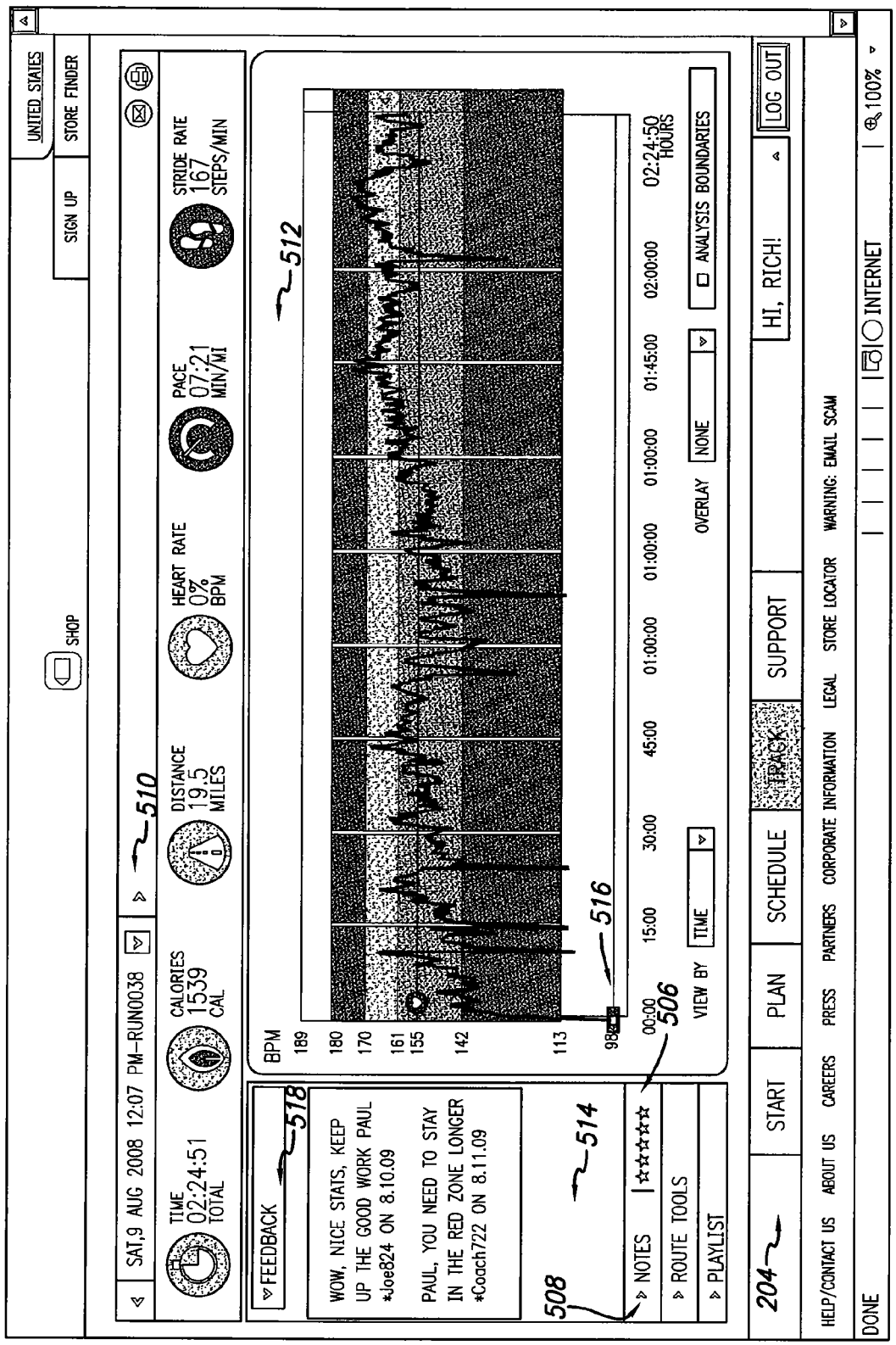
FIG. 27 is an exemplary GUI window according to an embodiment of the present invention.

The history display shown in FIG. 27 is similar to that shown in FIG. 26 in that the dashboard 510, primary display 512, and sidebar 514 are still present. However, FIG. 27 differs from FIG. 26 in that information provided in both the dashboard 510 and the primary display 512 is only associated with a single workout day. Additional functionality may also provided by the sidebar 514.

In one embodiment of the present invention, as shown in FIG. 27, the history sub-module 504 may provide a feedback 518 section in the sidebar 514. The feedback section may provide feedback from coaches, friends, or other individuals authorized to provide feedback to the athlete 100. All users of the system of the present invention having similar accounts through server 112 may be authorized to provide feedback to the athlete 100. Alternatively, only users of the system that are specifically authorized by the athlete 100 may provide feedback to the athlete 100. In an embodiment, users who are linked to the athlete 100 via a social networking site may also provide feedback to the athlete 100. Feedback may be provided through a GUI provided by sever 112, via email, via text message, via voice mail, or by any other suitable means known in the art. Feedback may be listed sequentially in the order that the feedback was posted, much like comments associated with a blog or other web article, as is known by those of skill in the art.

The history sub-module 504 may also provide a notes section in the sidebar 514. The notes section may provide a section for a user rating 506 and user notes 508. These ratings 506 and notes 508 may be similar to those described above with reference to FIG. 23.

The history sub-module 504 may provide a route tools section in the sidebar 514 that may be managed by a route tools sub-module 520. In one embodiment, the route tools sub-module 520 may allow the user 100 to associate specific routes with a workout when the workout involved the traversal of a particular geographic pathway. In one embodiment, the route tools sub-module may employ a web-based mapping service application, such as, for example, the Google Maps application provided by Google, Inc. of Mountain View, Calif. The mapping service application may utilize an application programming interface that allows the mapping service application, such as Google Maps, to be embedded into the GUI windows of the present invention.

Figure 28:
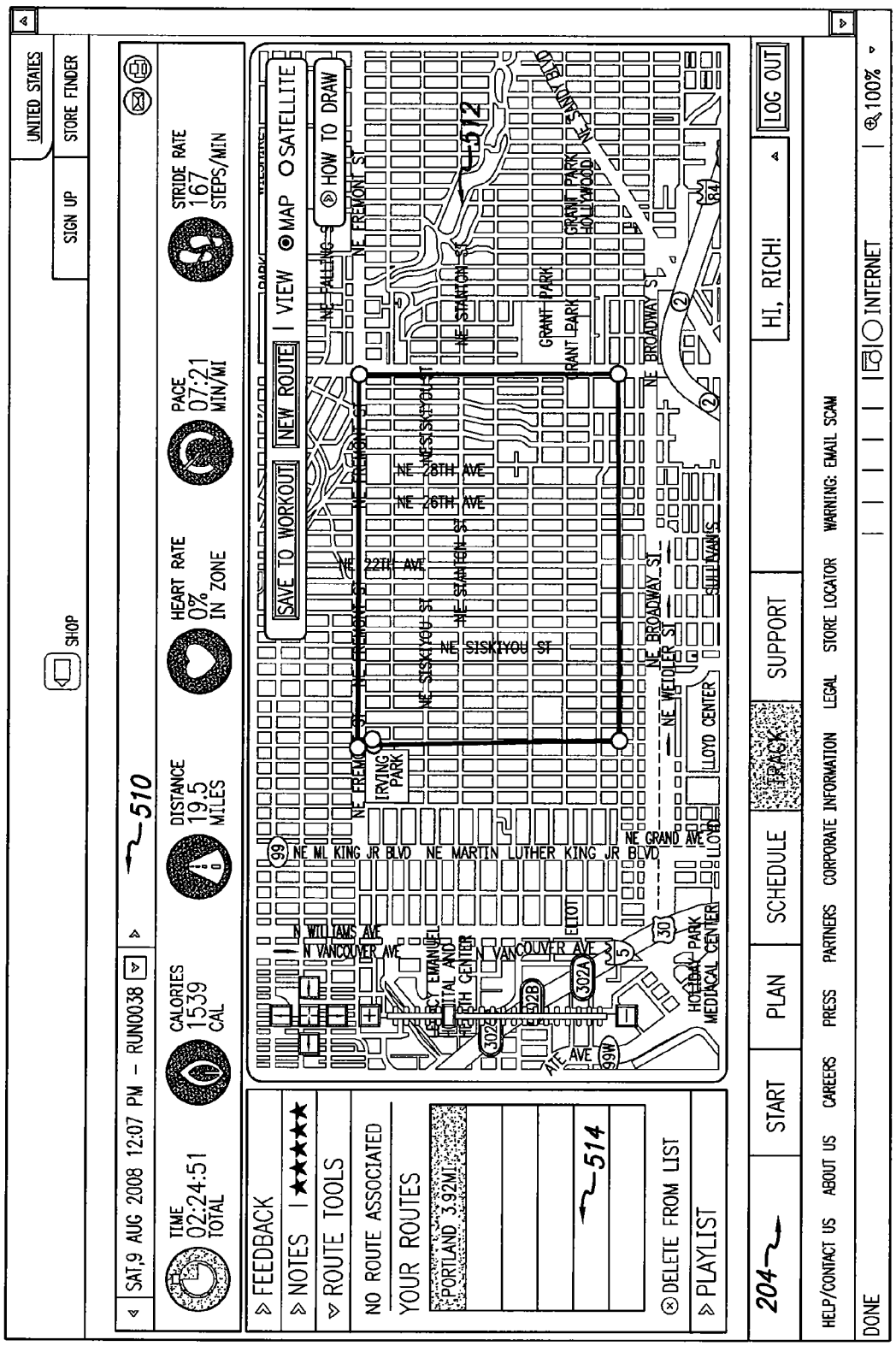
FIG. 28 is an exemplary GUI window according to an embodiment of the present invention.

As illustrated in FIG. 28, the route tools sub-module 520 may enable the user 100 to recreate the path they traversed during the workout by clicking, and/or dragging and dropping landmarks and paths over a street map using the cursor 206. The approximate area of the route may be found by, for example, entering a street address, a well-known landmark, or a zip code into the mapping service application interface. Alternatively, in an embodiment, the athlete 100 could conduct their workout using a GPS-enabled portable fitness monitoring device 102 capable of recording their geographic way points along the route traversed. Either during traversal of the route or after the route has been completed, the GPS data could then be uploaded to the server 112 and associated with other performance monitoring information collected during traversal of the route. Thus, the route tools sub-module 520 could automatically reconstruct the path traversed by the athlete 100.

In another embodiment, the route tools sub-module may allow the athlete 100 to create, store, share, and find route plans of interest. The route plan, which may or may not be associated with a particular workout, may be created or selected that specifies a particular route for the athlete 100 to travel. In an embodiment, the route plan may be downloaded to the portable fitness monitoring device 102. Athletes 100 may use route plans they themselves have created and stored on the sever 112. In one embodiment, other users 100 may post and share route plans with others. In one embodiment this functionality may be enabled by the forum module 800. Thus, a plurality of users 100 may be able to create, store, share, find, edit, rate, and comment on route plans of interest.

In an embodiment, the portable fitness monitoring device 102 may be able to guide the athlete 102 along a route, based on the route plan and, for example, the athlete's 102 current position based on GPS readings.

Figure 29:
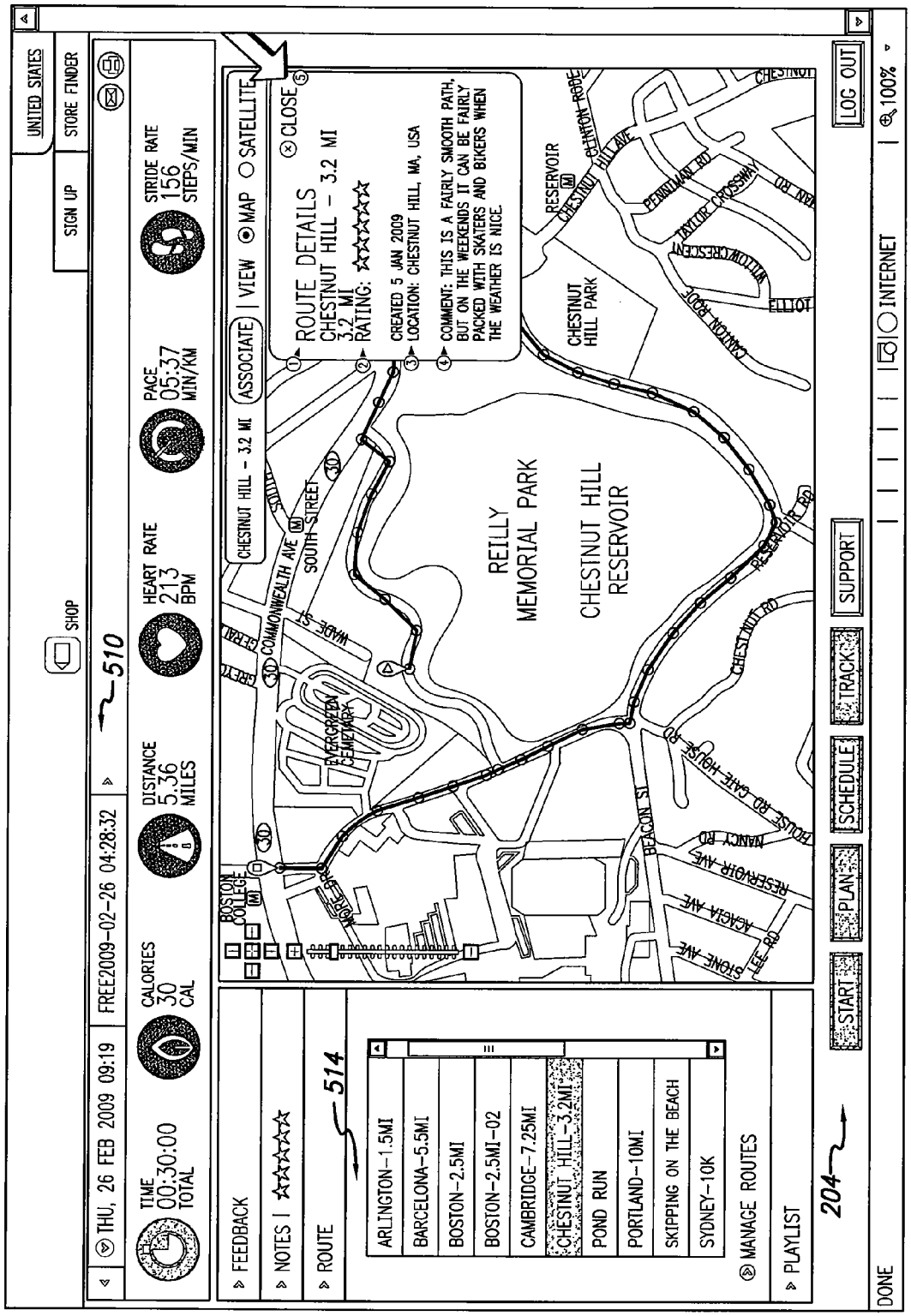
FIG. 29 is an exemplary GUI window according to an embodiment of the present invention.

In one embodiment, the user may save and name a route or route plan using the route tools sub-module 520. In the embodiment of FIG. 29, as shown in the sidebar 514, the user 100 has named and saved a plurality of routes or route plans to the server 112. In the event that a particular route or route plan has not been automatically assigned to a given workout record, the user 100 may wish to select a route or route plan with the cursor 206 to associate with their workout.

Saved routes or route plans may be displayed in primary display 512 if the user 100 selects an appropriate icon. Route details such as the route name, distance, and location may be provided in a GUI pop-up window. The user 100 may also be able to assign a subjective rating and include notes about the route. These features are analogous to the user rating 506 and user notes 508 features described above with respect to FIG. 23.

In an alternate embodiment of the present invention, the various route functionalities described herein may be provided through a separate route module of the application software of server 112 at the same functional level as the other primary modules illustrated in FIG. 3, such as the start module 200, the plan module 300, the schedule module 400, the track module 500, the support module 600, the library module 700, and the forum module 800. Accordingly, a route module icon may be provided on the menu bar 204.

Figure 30:
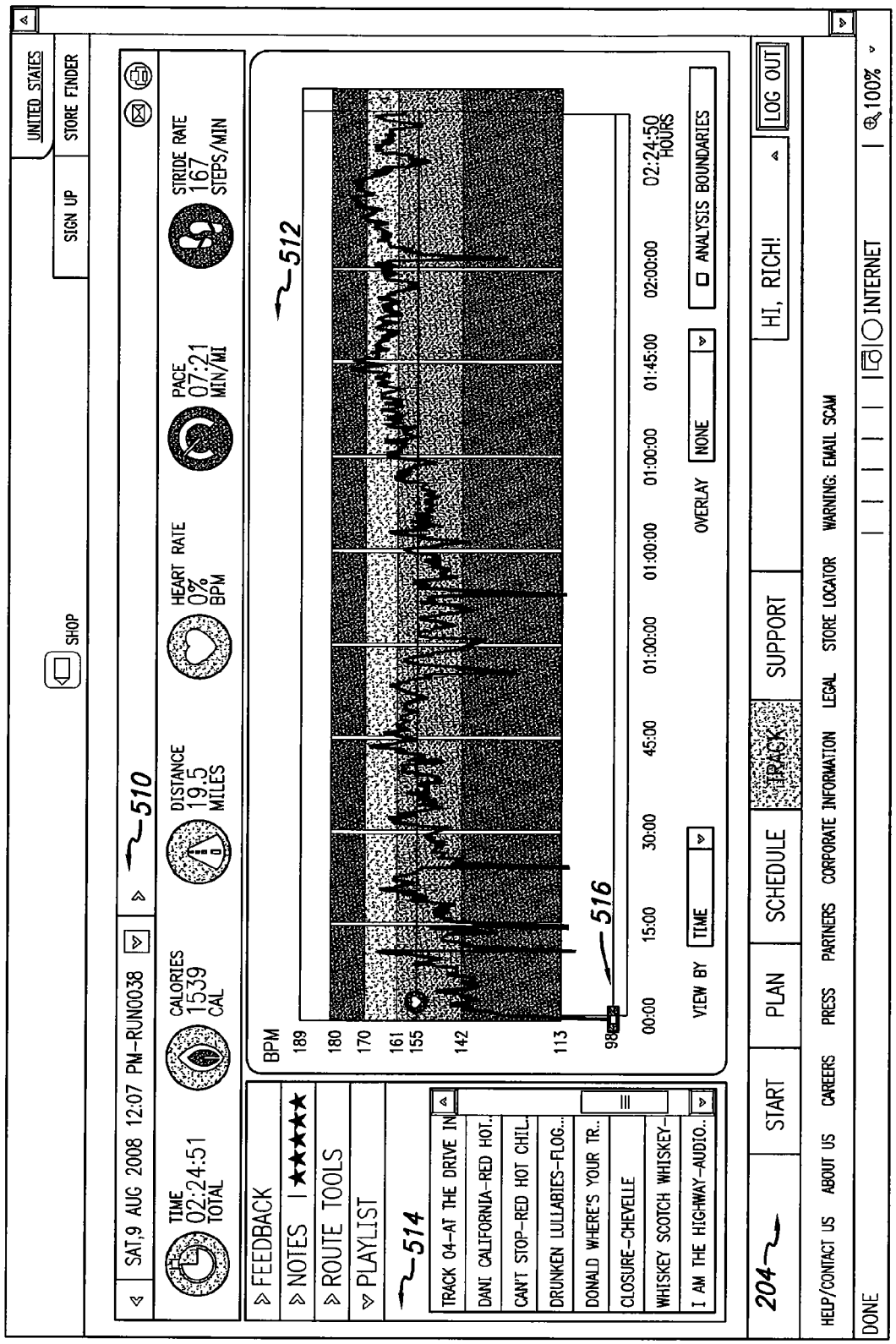
FIG. 30 is an exemplary GUI window according to an embodiment of the present invention.
Figure 31:
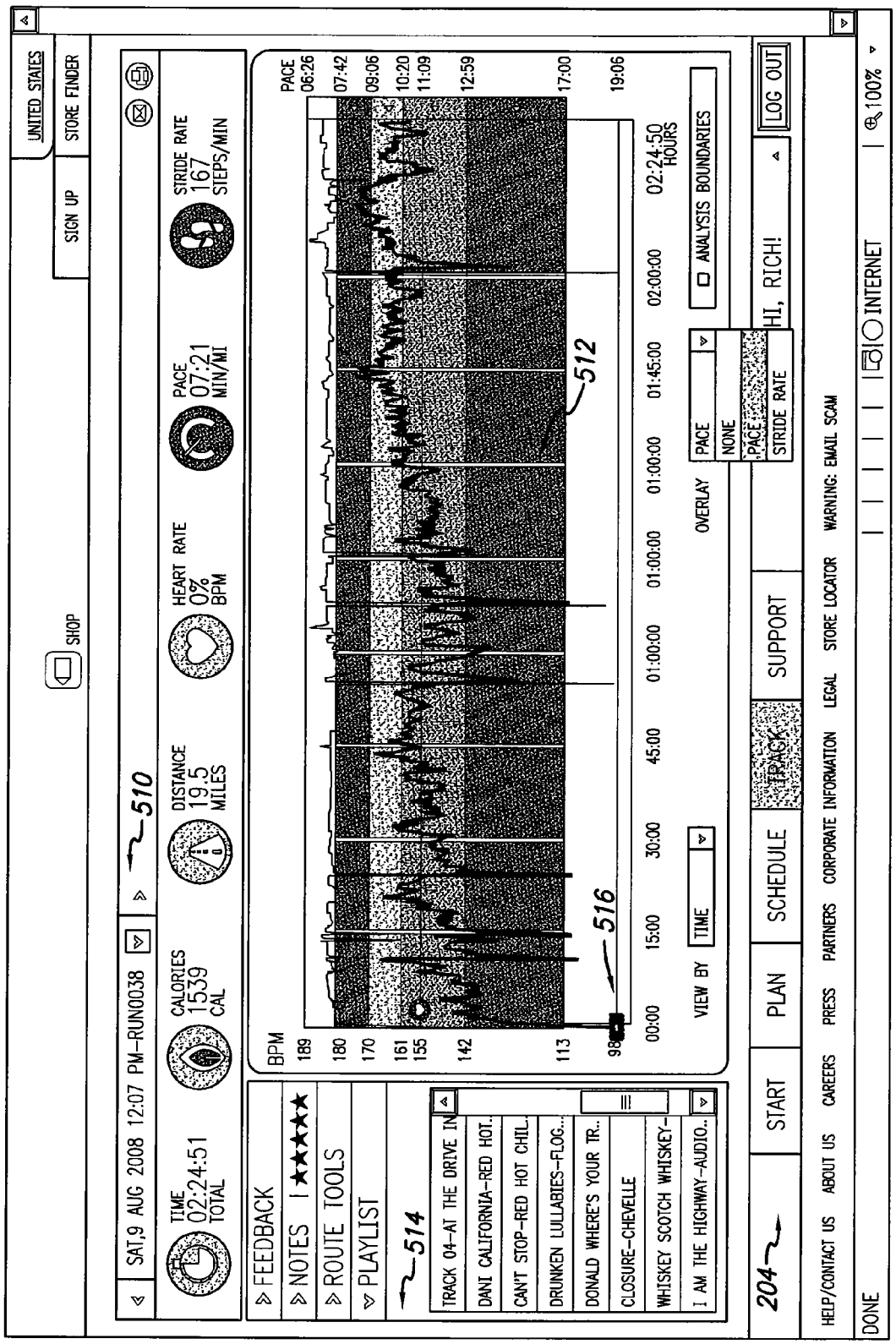
FIG. 31 is an exemplary GUI window according to an embodiment of the present invention.

In another embodiment of the present invention, as illustrated in FIG. 30, the history sub-module 504 may further provide a playlist 522 section in the sidebar 514. If the user 100 conducted a workout while listening to music on a music-enabled portable fitness monitoring device 102 (or with a portable fitness monitoring device coupled to a music device), the playlist 522 section may provide a listing of the musical audio tracks that the user 100 listened to during their workout.

In an embodiment, a particular play list may be associated with a particular route plan or workout so that the play list may be downloaded to the portable fitness monitoring device 102 simultaneously with the route plan and/or workout. Accordingly, the user 100 may be able to easily perform the same workout and/or traverse the same route while listening to the same play list. The athlete 100 could also fine tune their play list until the athlete felt that the play list provided appropriate entertainment, motivation, or other benefits during the physical activity.

As illustrated in, for example, FIGS. 27 and 30, the history sub-module 504 may be capable of displaying a variety of performance parameter information about a particular workout in the dashboard 510 and primary display 512 areas of a GUI window. As was the case with the weekly and daily summary displays of performance information shown in FIGS. 24-26, while the information provided by the dashboard 510 icons may remain the same for a given workout, the information displayed by the primary display 512 may change depending on which dashboard 510 icon the user 100 has selected. For example, in FIG. 30, because the user 100 has selected the heart rate icon in the dashboard 510, the history sub-module 504 displays heart rate information in the primary display 512.

In an embodiment, the heart rate information provided with the heart rate icon in the dashboard 510 is an average heart rate in beats per minute over the entire workout. In another embodiment, the heart rate information provided with the heart rate icon in the dashboard 510 is a percentage indicating how often the athlete 100 was exercising at the appropriate heart rate, as indicated by their workout plan for the given workout (i.e. their "percentage in zone"). The percentage in zone may be based on time or distance. For example, an athlete's 100 plan may call for a 30 minute jog in the blue zone followed by a 30 minute run in the green zone. The athlete 100 may cover 4 miles during the blue zone jog while staying in the proper zone 80% of the time, and 8 miles during the green zone run, while staying in the proper zone 40% of the time.

Accordingly the athlete's 100 percentage in zone for the entire run based on time would be 60%, while the athlete's 100 percentage in zone for the entire run based on distance would be approximately 53%. Percentage in zone based on one or both of time and distance may be displayed at a given time.

In one embodiment, a "success rate" may be calculated and provided to the user 100. In this manner, the user may receive performance feedback about a particular workout or series of workouts. The success rate may be displayed in the dashboard 510 and may be provided in cumulative and/or average form. In an embodiment, the success rate may be equal to the percentage in zone. In another embodiment, the success rate may be proportionate to the percentage in zone. Other factors may be used to calculate the success rate including, but not limited to, whether a personal best for a particular parameter (e.g. time, pace, distance, etc.) was achieved during a workout, whether the athlete 100 left a zone too early, whether the athlete's 100 heart rate appeared to recover quickly after completing a difficult zone interval, whether the athlete's 100 performance was consistent throughout the workout, and/or how the athlete performed during specific key interval training sessions.

Figure 38:
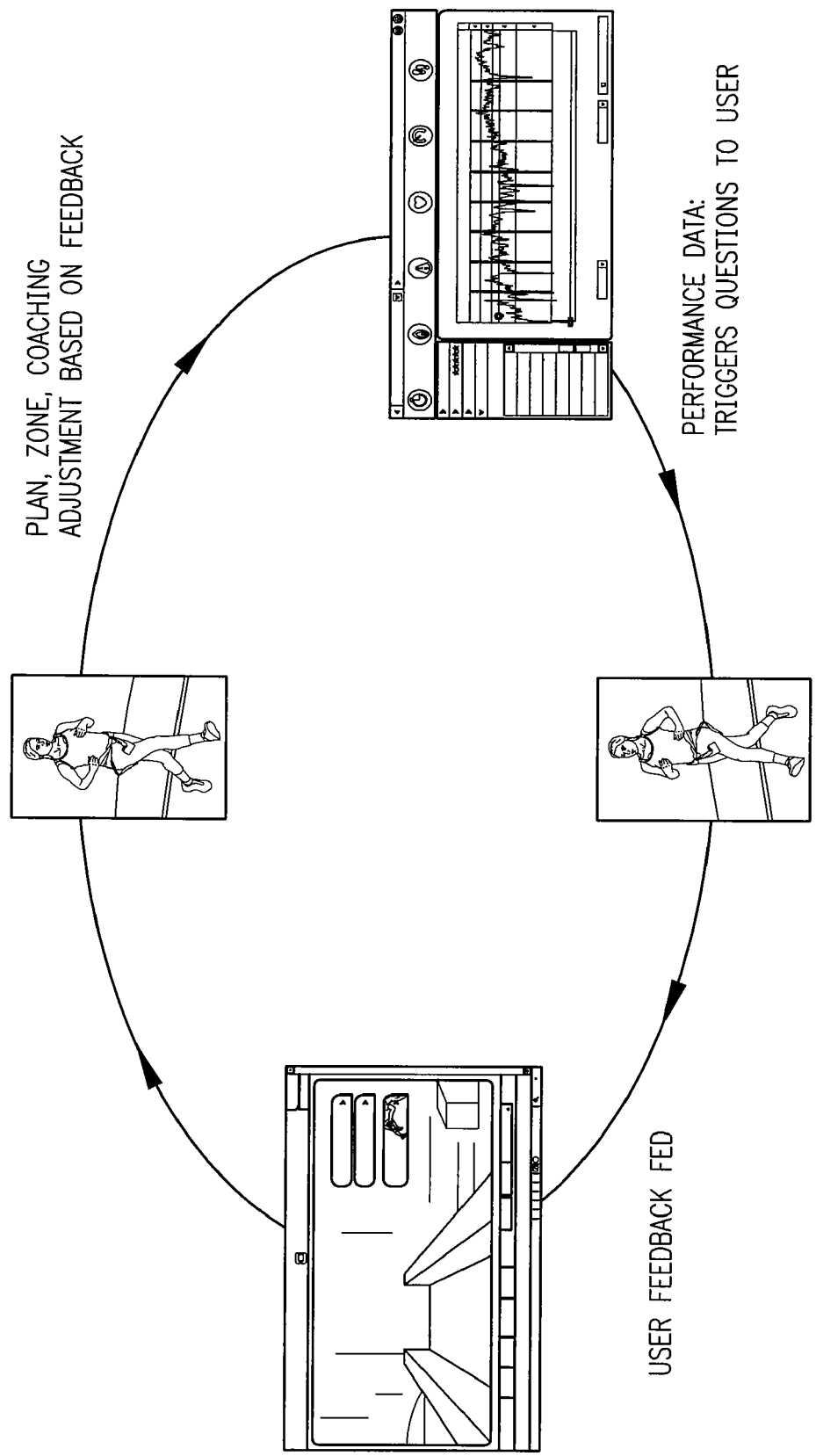
FIG. 38 is a diagram that illustrates the process of making zone adjustments based on feedback according to an embodiment of the present invention.

After the zones have been initially defined, the portable fitness monitoring system may be adapted to selectively adjust the limits of the zones in response to the athlete's 100 performance and/or feedback received from the athlete 100, if such adjustments are warranted, as illustrated in FIG. 38. In this manner, the portable fitness monitoring system may provide a training feedback loop. As described above, the zones may be defined based on user input. User 100 performance parameter data is detected during a physical activity via the sensors 104, as described above. The performance parameter data is transmitted to the personal computer 114 and/or the server 112 for processing. A determination is made as to whether the zones need to be adjusted. If adjustments are warranted, this data may be communicated back to a portable fitness monitoring device 102.

The determination as to whether or not the zones need to be adjusted may be based on, for example, the factors described above with respect to success rate calculations. In one embodiment, if the athlete 100 performs outside the specified heart rate zone for all or a portion of the interval, the heart rate zone may be adjusted. For example, if the athlete 100 is consistently above the specified zone, the zone range may be increased. If the athlete 100 is consistently below the specified zone, the zone range may be decreased.

Determinations may further be influenced by feedback provided by the athlete 100. For example, the athlete 100 may provide responses to questions posed by the portable fitness monitoring system. For example, upon uploading recently recorded performance parameter data, or upon logging in to the personal computer 114 and/or server 112, a GUI pop-up window may appear asking the user 100, for example, if they thought the workout routine was too difficult or too easy. If the user 100 responds that a workout routine was too difficult, the zone range may be incrementally decreased. If the user 100 responds that a workout routine was too easy, the zone range may be incrementally increased. The athlete's 100 answers to these questions may also influence the success rate calculations described above.

Returning to FIG. 30, in one embodiment, the performance information to be displayed in the primary display 512, based on the selected dashboard 510 icon, may be displayed on a line graph whose x-axis is either time or distance based, and whose y-axis is correlated to the value of the measured performance parameter. For example, as shown in FIG. 30, a line graph charts heart rate information as a function of time during the workout.

Average lines may also be plotted parallel to the x-axis across the graphs. For example, in FIG. 30, an average heart rate line representing the athlete's 100 average heart rate of 155 beats per minute during the workout is plotted across the graph.

In an embodiment, certain performance parameters may be simultaneously plotted or overlaid on top of other performance parameters. For example, in FIG. 31, the athlete's 100 pace has been plotted on top of the athlete's 100 heart rate as a function of time.

Figure 32:
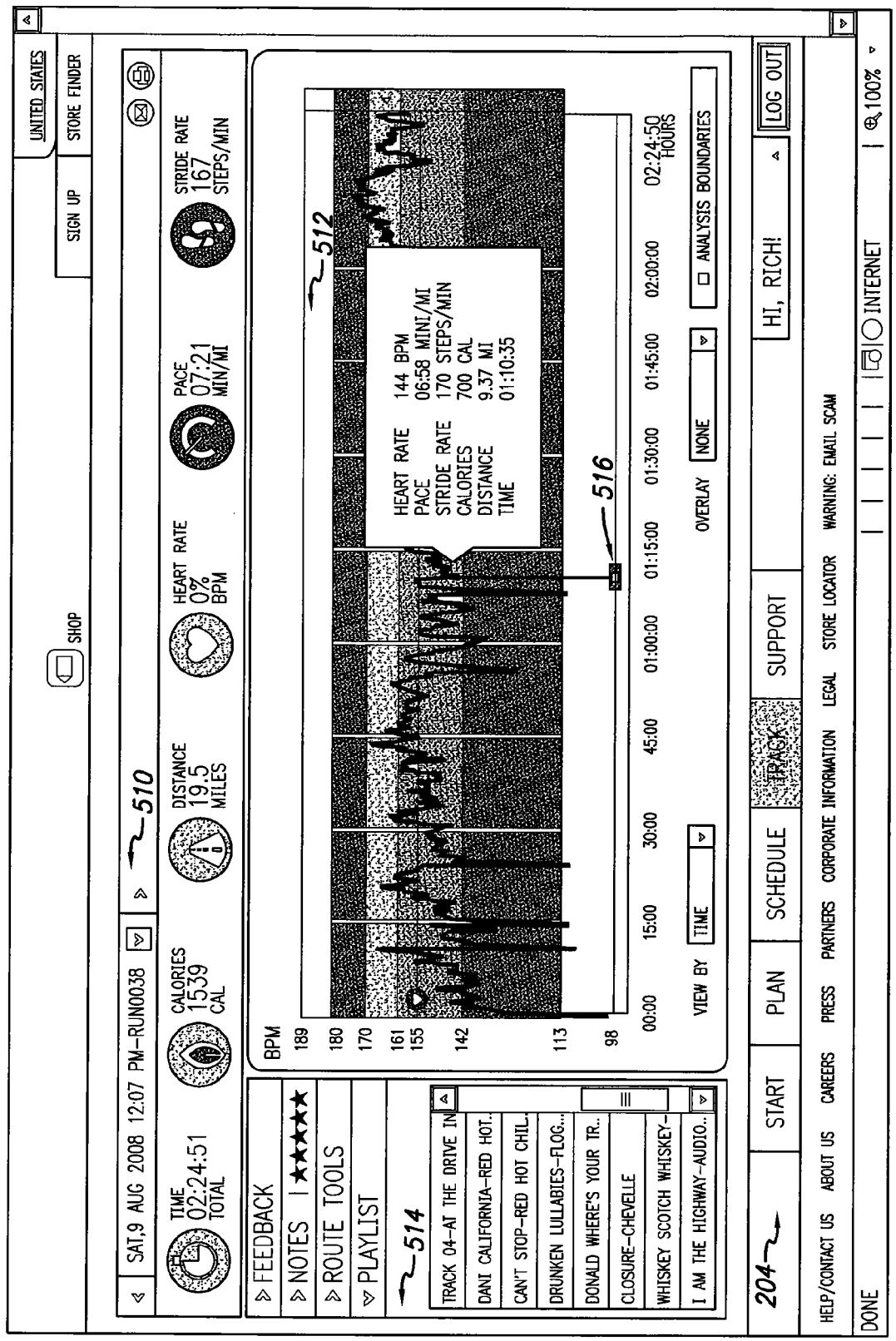
FIG. 32 is an exemplary GUI window according to an embodiment of the present invention.

The user 100 interested in viewing instantaneous performance statistics throughout the workout may be able to select and drag a scrollbar 516 with their cursor 206 along the x-axis. The scrollbar 516 of this embodiment may function similarly to the scrollbar 516 described with reference to FIG. 24. As the user 100 drags the scrollbar 516 across the x-axis, an icon may travel along the line graph plotted for the performance parameter of interest. In addition, a pop-up window displaying additional instantaneous performance data may appear and move across the screen along with the moving icon. FIG. 32 is an illustration of an icon and pop-up window containing instantaneous performance parameter information being moved across a GUI screen by means of a scrollbar 516.

Figure 33:
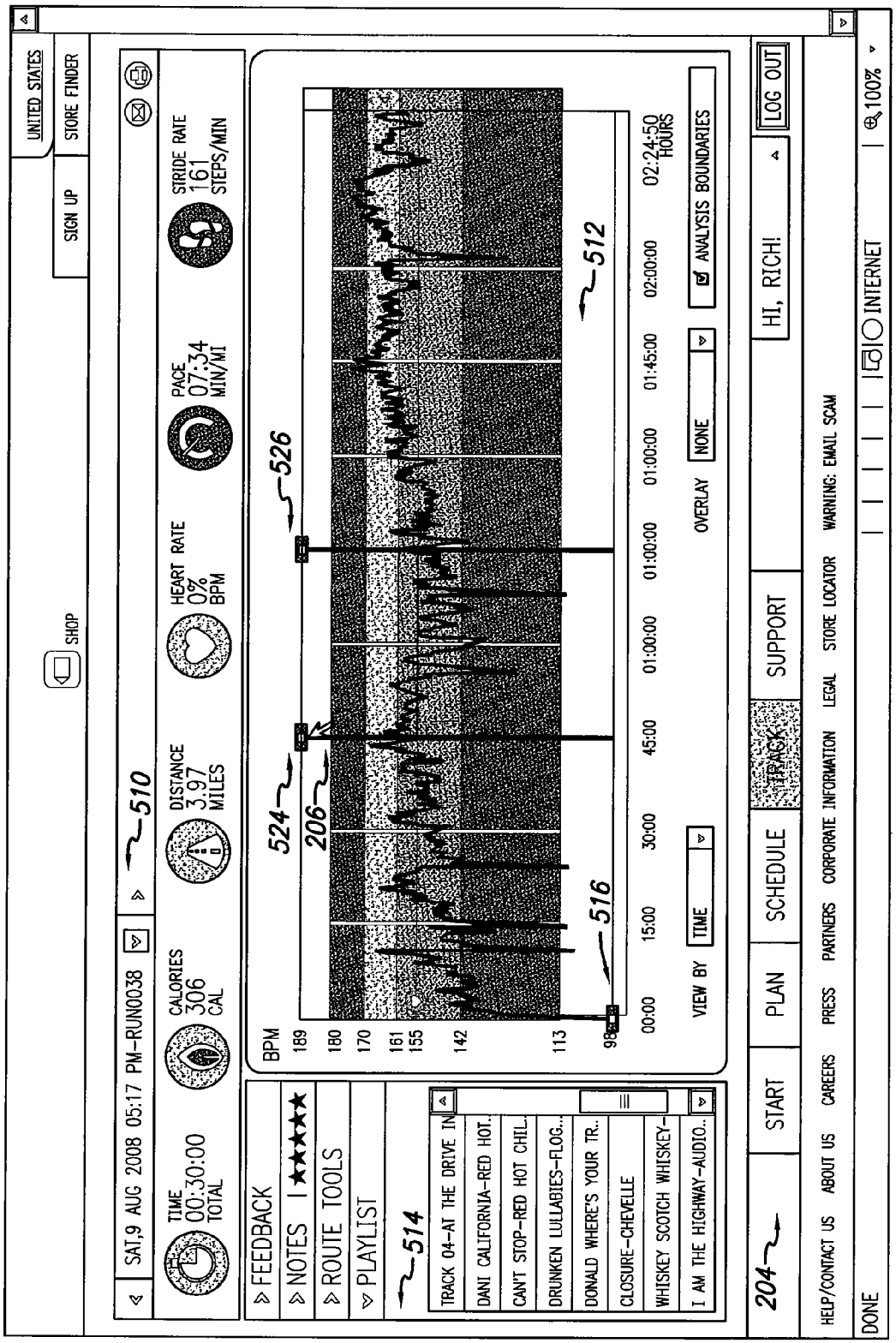
FIG. 33 is an exemplary GUI window according to an embodiment of the present invention.
Figure 34:
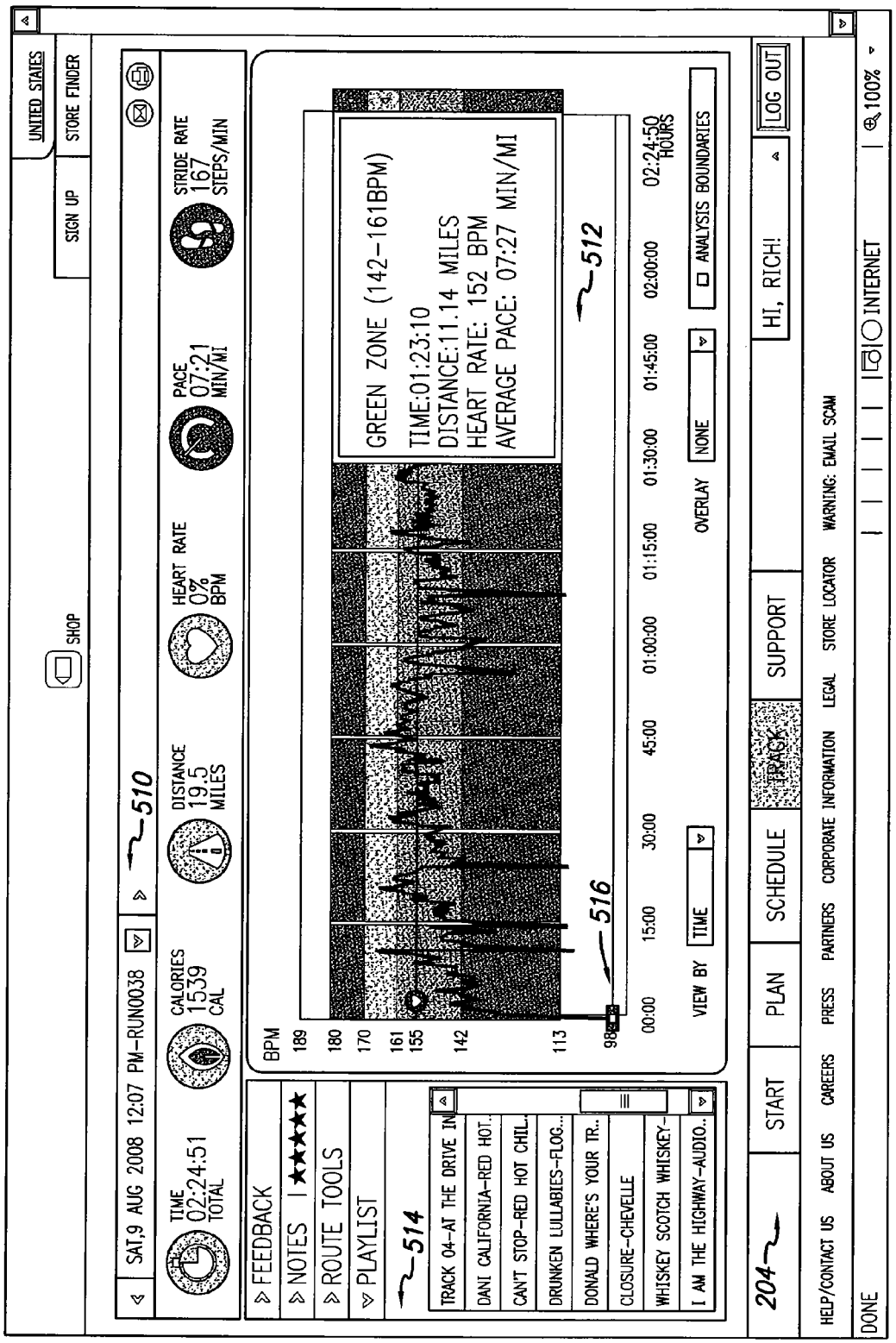
FIG. 34 is an exemplary GUI window according to an embodiment of the present invention.

In another embodiment, the user 100 may be able to display summary performance information for a subset of the workout in the dashboard 510. In one embodiment, the user 100 may manipulate first and second analysis boundaries 524 and 526. The user 100 may enable use of the analysis boundaries by selecting an icon with their cursor 206. Once analysis boundaries are enabled, a first analysis boundary marker 524 may appear on the left side of the performance parameter graph in primary display section 512, and a second analysis boundary marker 526 may appear on the right side of the performance parameter graph in primary display section 512. As shown in FIG. 33, using the cursor 206, the user may drag and drop the first and second analysis boundary markers 524 and 526 so that only a subset of the performance parameter graph (the portion remaining between the two analysis boundary markers) is highlighted. When analysis boundaries are enabled, the numerical performance parameter information displayed in the dashboard 510 is only summed and/or averaged for the subset of the workout highlighted within the analysis boundary markers.

When heart rate information is selected and displayed in the primary display 512, icons representing the red, yellow, green, and blue zones may be positioned on the right side of the heart rate graph in primary display section 512. The user 100 may select or hover the cursor 206 over one of these icons to display summary information for only the portions of the workout where the user 100 was performing in the zone associated with the selected icon. For example, in FIG. 34, the user 100 has selected the green icon on the right side of the heart rate graph. History sub-module 504 then displays a pop-up window that may detail, for example, the numerical heart rate range corresponding to the selected zone for the particular user 100 during that particular workout, as well as time, distance, heart rate, and pace information associated with the user's 100 activity in the selected zone during the workout.

Figure 35:
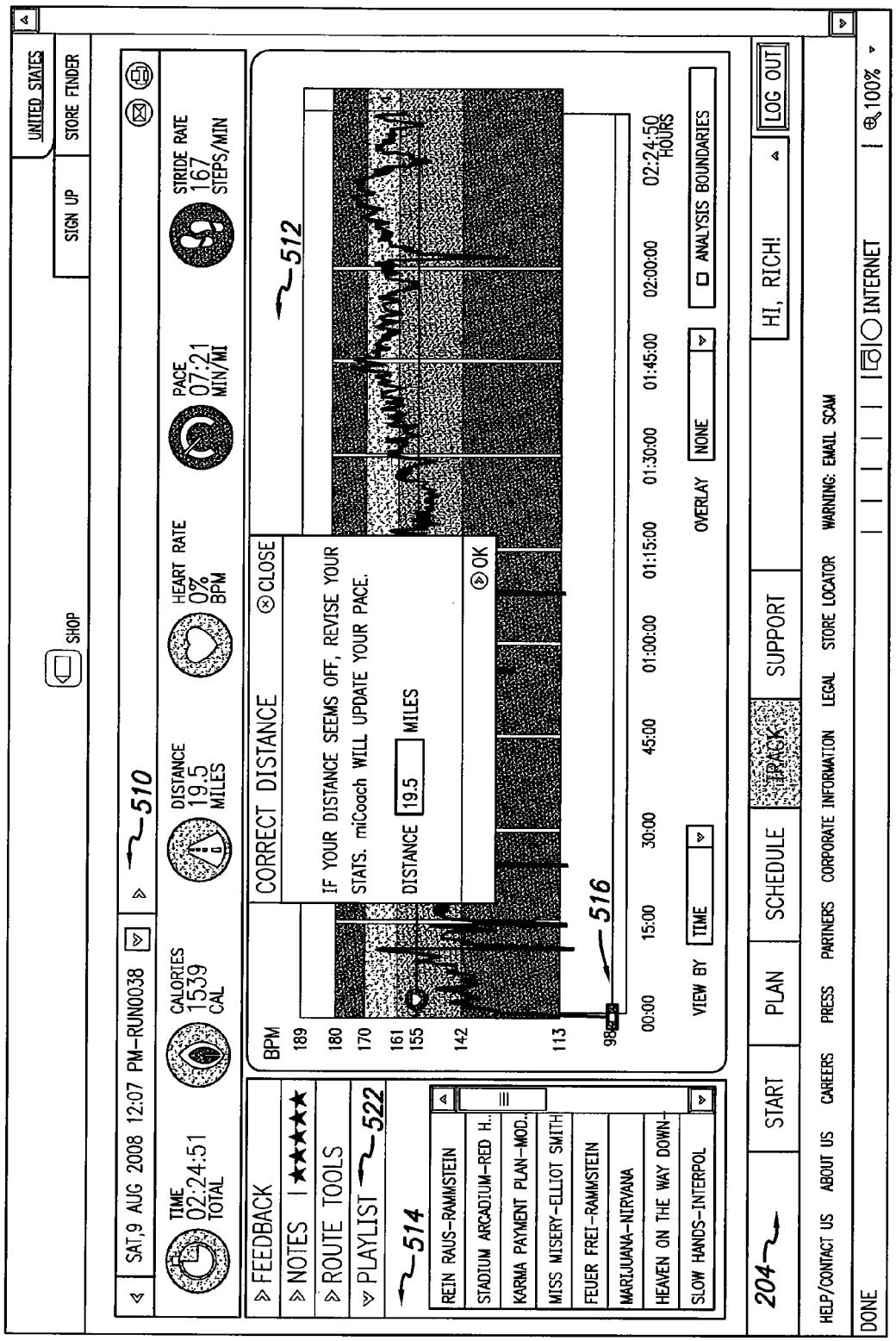
FIG. 35 is an exemplary GUI window according to an embodiment of the present invention.

In an embodiment, the user 100 may be able to manually correct any recorded parameters that they know are inaccurate. Inaccuracies may be due to, for example, errors with the sensors 104 employed by the portable fitness monitoring device 102 used by the athlete 100. As shown in FIG. 35, a user 100 may correct, for example, the distance they traveled during a workout. The user 100 may know the exact distance of a route routinely traveled and wish to update a distance inaccurately recorded by a distance sensor 104.

In another embodiment, when a parameter, such as distance, is corrected, the system may recalibrate the recorded and stored data. For example, when the distance traversed for a particular run is corrected, the distance data and corresponding distance graph for that run is corrected. In addition, data and graphical displays that depend on the distance data, such as pace data and graphical displays, are also corrected.

In a further embodiment, when a parameter, such as distance, is corrected, this corrected data may be transmitted to the portable fitness monitoring device 102 the next time the device is in communication with the network 112 so that the portable fitness monitoring device's 102 distance monitoring capability can be recalibrated, if necessary.

Figure 36:
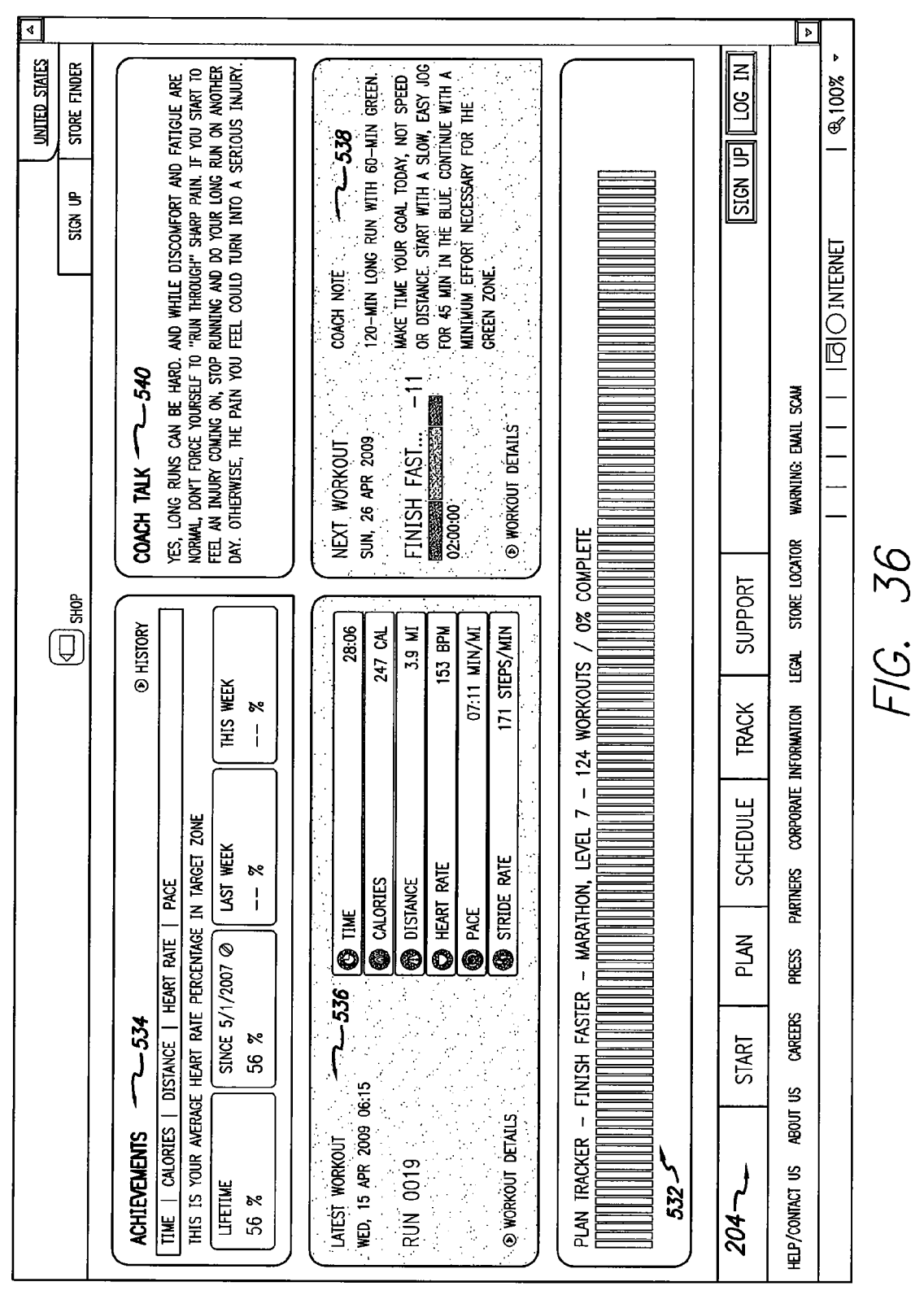

The track module 500 may also provide a front page sub-module 530. FIG. 36 is an exemplary GUI window that may be displayed by the front page sub-module 530. The front page GUI may include plan tracker 532, achievements 534, last workout 536, next workout 538, and coach talk 540 sections. In an embodiment, the contents of the front page may be customized and reordered similarly to customizable web portals such as, for example, the iGoogle web portal.

The achievements section 534 may provide icons that are correlated to particular performance parameters. In this way information displayed by the achievements section 534 on the front page may be similar to information displayed by the dashboard 510 of the other history pages. When a user 100 selects a performance parameter icon in the achievements section 534, cumulative and/or average information about that parameter for various time periods may be displayed in the achievements section 534. For example, as shown in FIG. 36, heart rate percentage in zone may be displayed for the entire time the user 100 has used the portable fitness monitoring system, since a specific date, in the last week, or in the current week. The particular information displayed in the achievement section may be set by the system or customized by the user 100. Various information may be added or removed by the user 100 as desired.

In an embodiment, the last workout section 536 displays stats for the last workout completed by the user 100, and the next workout section 538 displays information about upcoming planned workouts. The information provided by the achievements 534, last workout 536, and next workout 538 sections may be similar to information provided to the user 100 by other modules and sub-modules, but may conveniently be provided on a single page. The coach talk section 540 may provide information similar to that provided by the coaching tips included in the workout list 318, as described above with respect to FIG. 18. The coach talk section 540 may therefore provide motivation, point out a particular area of focus, or otherwise provide guidance to the athlete 100 related to the ultimate goal of their particular plan or workout.

In one embodiment, front page includes a plan tracker 532 section. The plan tracker 532 may graphically display an individual's 100 planned workouts, the number of planned workouts completed, and the number of planned workouts remaining to be completed. The plan tracker 532 may provide indication(s) about whether the individual 100 is meeting the specified goals for the completed workouts.

The particular information displayed in the plan tracker 532 section may be set by the system or customized by the user 100. Various information may be added or removed by the user 100 as desired. A user 100 engaged in multiple plans simultaneously (e.g. a running based plan and a non-running based plan) may choose to display multiple plan trackers 532 at once. In an embodiment, other trackers may be provided that display information similarly to the plan tracker 532. For example, an athlete with a goal to lose weight may chose to display a weight tracker that tracks their progress towards a weight loss goal.

Figure 37:
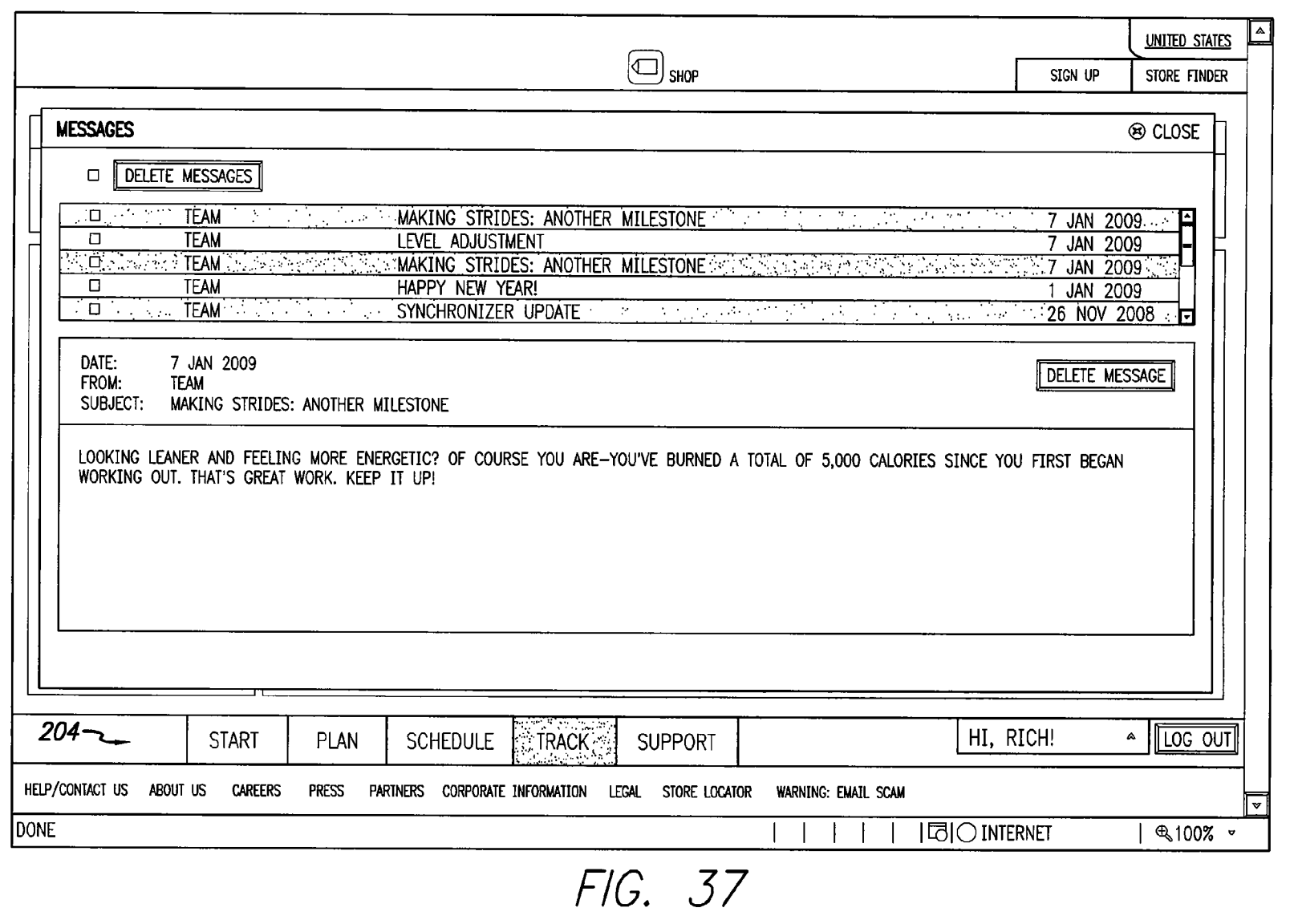

The track module 500 may also support a message sub-module 528. FIG. 37 is an exemplary GUI window that may be displayed by the message sub-module 528. The message sub-module GUIs may have the general look and functionality of an email application such as Windows Mail or Gmail. In an embodiment, the message sub-module may be linked to one or more email addresses. The email addresses may include an email address specifically associated with the user's 100 fitness monitoring system or general purpose email accounts provided by other providers.

At least some of the messages received by the user 100 via the message sub-module 528 may be automatically generated by the server 112. Messages may, for example, congratulate the athlete 100 for achieving certain training milestones or personal bests, may provide motivation or other training advice to the athlete 100, may provide new product or service updates and/or downloads, and may include other things such as birthday or holiday greetings.

As indicated above, the menu bar 204 may include several icons or indicia corresponding to the support 600, library 700, and forum 800 modules.

Figure 39:
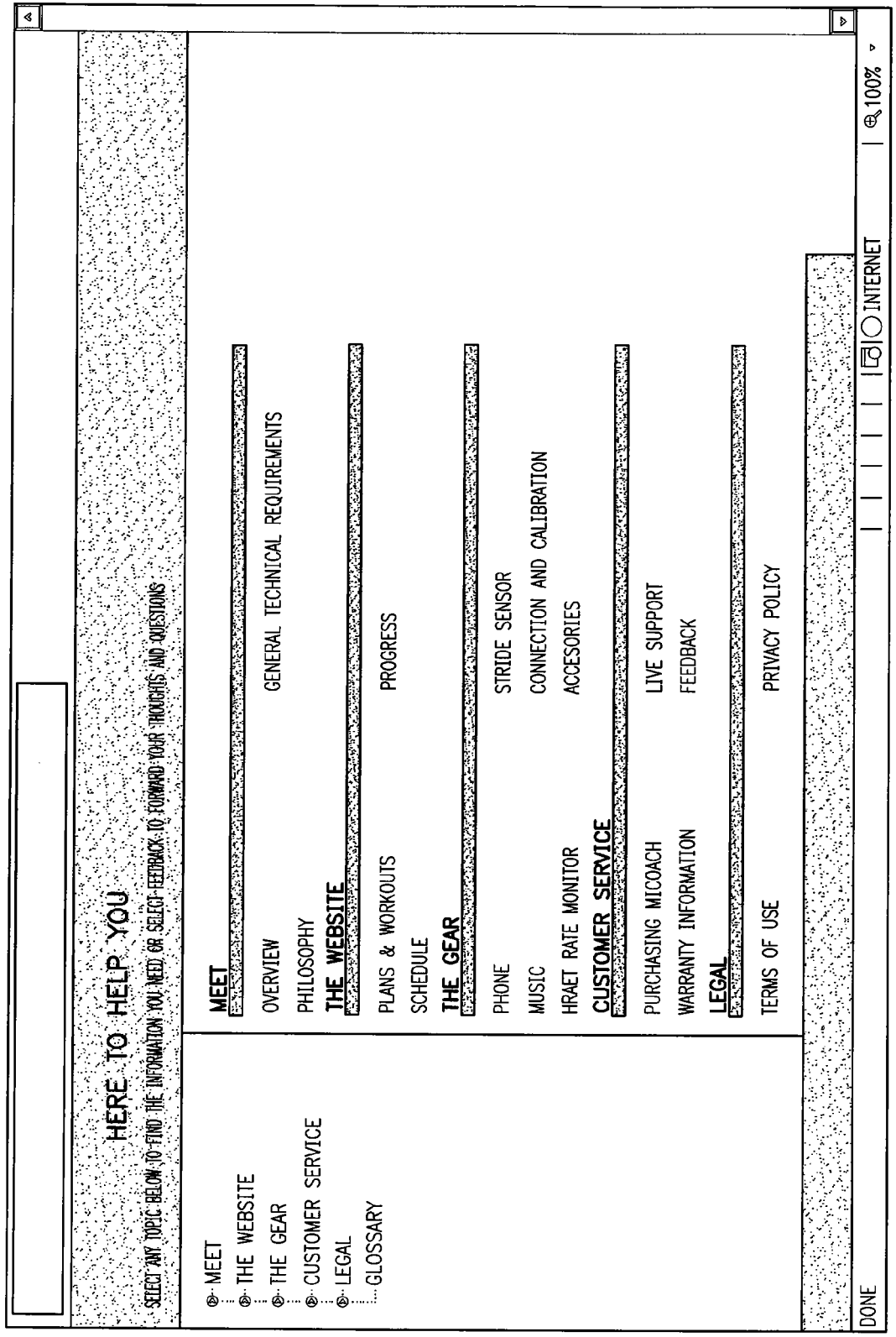
FIG. 39 is an exemplary GUI window according to an embodiment of the present invention.

The support module 600 may support help 602 and settings 604 sub-modules. FIG. 39 is an exemplary GUI window that may be displayed by the help sub-module 602. The help sub-module 602 may contain general information about the fitness monitoring system of the present invention, including a brief description of the system, its intended users, and the potential benefits available to those users The help sub-module 602 may provide a description of the various functions of the interactive website supported by the software and the underlying modules, sub-modules, and wizards.

The settings sub-module 604 may be able of displaying GUI windows for collecting, storing, and reviewing personal settings 606, workout settings 608, device settings 610, and privacy settings 612.

Figure 40:
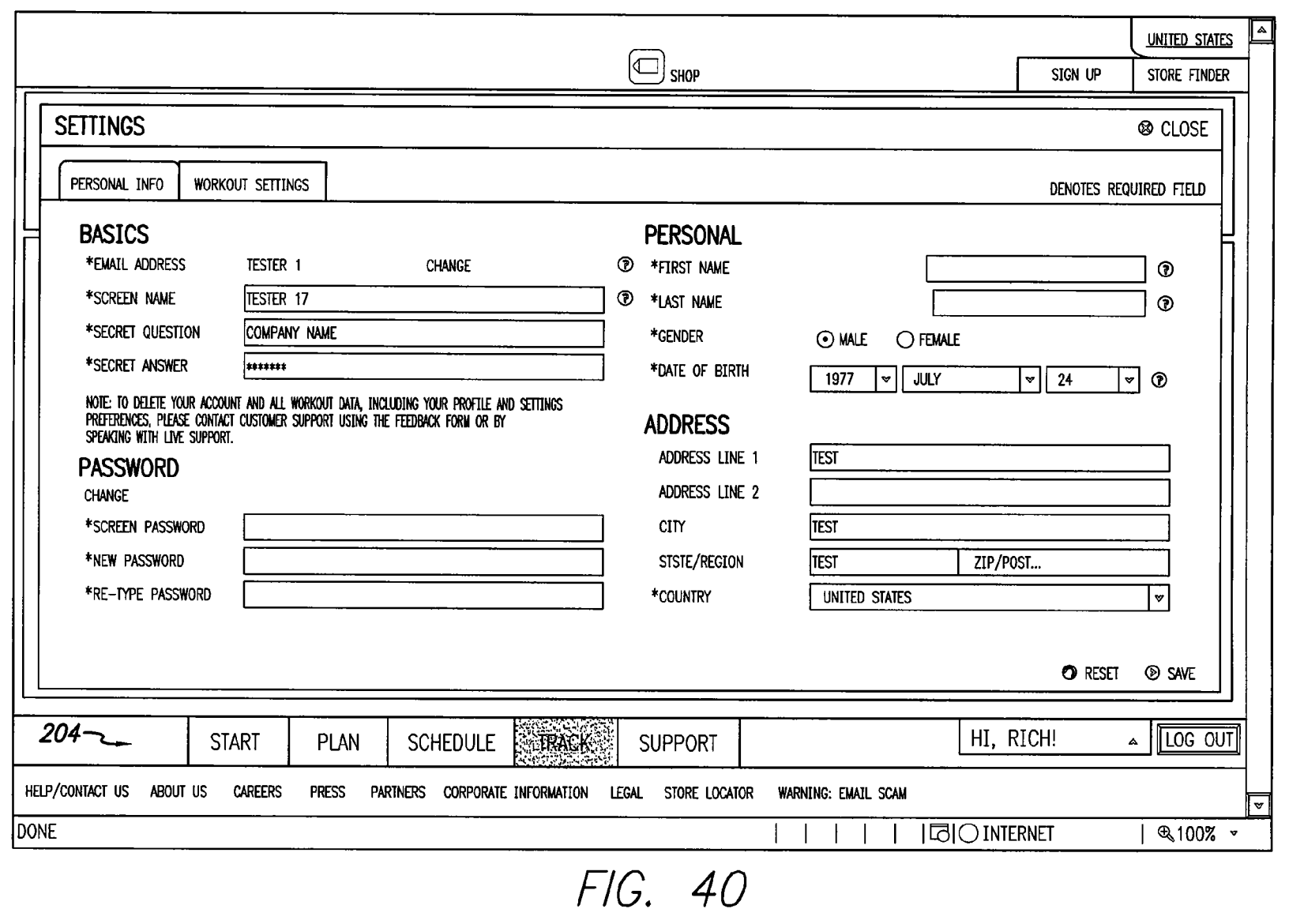

FIG. 40 is an exemplary GUI window that may be displayed by the settings sub-module 604 for collecting personal settings 606 information. Personal settings 606 information may include, for example, name, address, email address, password, gender, birth date, and address information. This information may be used to associate a specific user 100 with a particular user account. In an embodiment, some of this information may be used to tailor aspects of the portable fitness monitoring system to the user 100, or to provide messages, product offers, or other items of interest to the user 100.

FIG. 41 is an exemplary GUI window that may be displayed by the settings sub-module 604 for collecting workout settings 608 information. Workout settings 608 information may include preferences such as preferred distance units (miles vs. kilometers), height units (feet and inches vs. meters and centimeters), weight units (pounds vs. kilograms), time format (12 hour clock vs. 24 hour clock), and a preferred week start date (e.g. Sunday or Monday). Workout settings 608 information may also include fitness profile information such as the user's weight, height, and maximum heart rate (if known). In one embodiment, the user may be periodically prompted by the system to update their fitness profile information.

The workout settings page may graphically and/or numerically display the user's 100 current zone ranges according to the color-coded heart rate zone system described above. In an embodiment, the user 100 may be able to configure and customize heart rate, pace, or other custom workout interval settings via the workout settings page.

FIG. 42 is an exemplary GUI window that may be displayed by the settings sub-module 604 for collecting device settings 610 information. Device settings information may include settings for any peripheral devices the user 100 has and is using in conjunction with the system of the present invention. These devices may include, for example, the devices discussed above with respect to FIG. 11, including mobile fitness phones, dedicated portable fitness monitoring devices, non-dedicated portable fitness monitoring devices, sports mode-enabled MP3 players, sports-enabled dongles, sports watches, display devices, and sensors (e.g. pedometers or heart rate sensors). The user may indicate which, if any, sensors they may use during their workouts.

For example, via the settings page, the user 100 may be able to adjust the audio feedback options provided by their portable device(s) during a workout. In one embodiment, the user may select audio feedback with different types or styles of voices such as, for example, voices of different gendered speakers, voices with different accents, voices in different languages, voices from celebrities or fictional characters, and voices of different tones (e.g. supportive, calming, energizing, or stem). In another embodiment, the user may select specific performance parameter measurements to be recited via audio feedback during the workout. For example, a user may choose to have their elapsed time, calories burned, and distance traveled so far announced to them at regular intervals, on demand, or at predetermined times throughout the workout.

FIG. 43 is an exemplary GUI window that may be displayed by the settings sub-module 604 for collecting privacy settings 612 information. Privacy settings 612 information may include, for example, whether the user's 100 profile and/or history are accessible to all users 100 or only select users 100. For those users 100 with access, the privacy settings 612 may control specifically what historical workout information is accessible (e.g. only workout data from the last workout vs. all workout data).

The privacy settings page may also allow the user 100 to link their fitness monitoring account to a social networking site, such as, for example, Facebook, MySpace, Twitter, Friendster, LinkedIn, or the like. Users 100 who link their profile to a social networking site may be able to specify how often their fitness information is updated to their social networking site and specifically what type of information is provided.

The library module 700 may be capable of displaying GUI windows for videos 702 and articles 704. The videos 702 and articles 704 may provide the user 100 with additional resources for planning, preparing for, an executing their workouts.

Figure 44:
FIG. 44 is an exemplary GUI window according to an embodiment of the present invention.

FIG. 44 is an exemplary GUI window that may be displayed by the library module 700 for providing videos 702. The library module 700 may include a videos 702 section that provides short animations and/or videos teaching the user 100 proper stretching, warm-up, cool-down, and other exercising techniques. The user 100 may select a video 702 icon with their cursor 206 to display the video 702.

Figure 45:
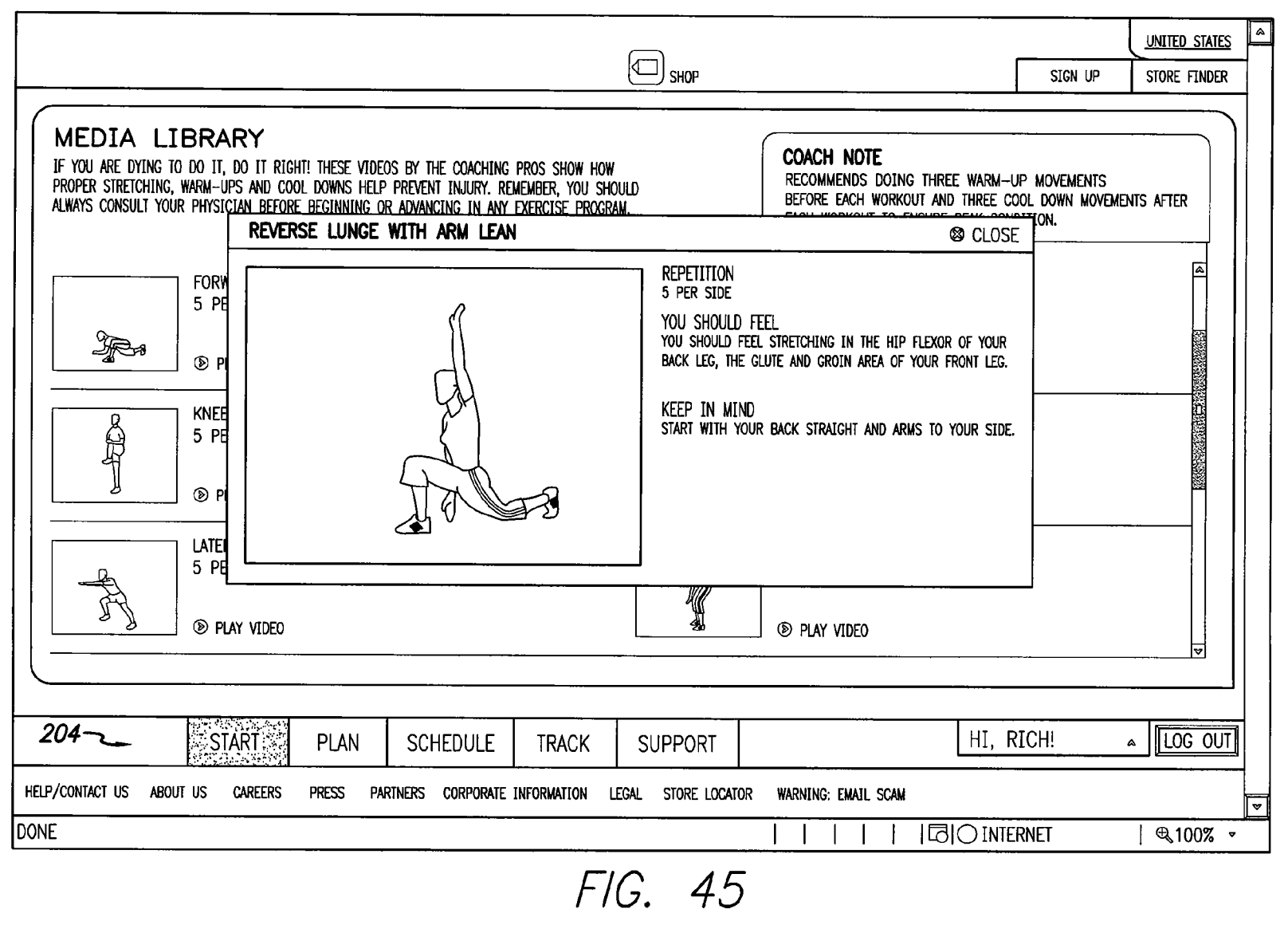

FIG. 45 is an exemplary GUI pop-up window that may appear in response to the user 100 selecting a particular video. The pop-up window may include the animation and/or video, a suggested number or time period for the activity, and other notes or comments about the activity.

In an embodiment, the user 100 may be able to download videos 702 from the server 112 to a portable fitness monitoring device 102 having a video screen so that they may be viewed remotely. This may allow the athlete 100 to view instructions regarding preparing for or executing their workouts at the site of their workout prior to or during their exercise routine.

Figure 46:
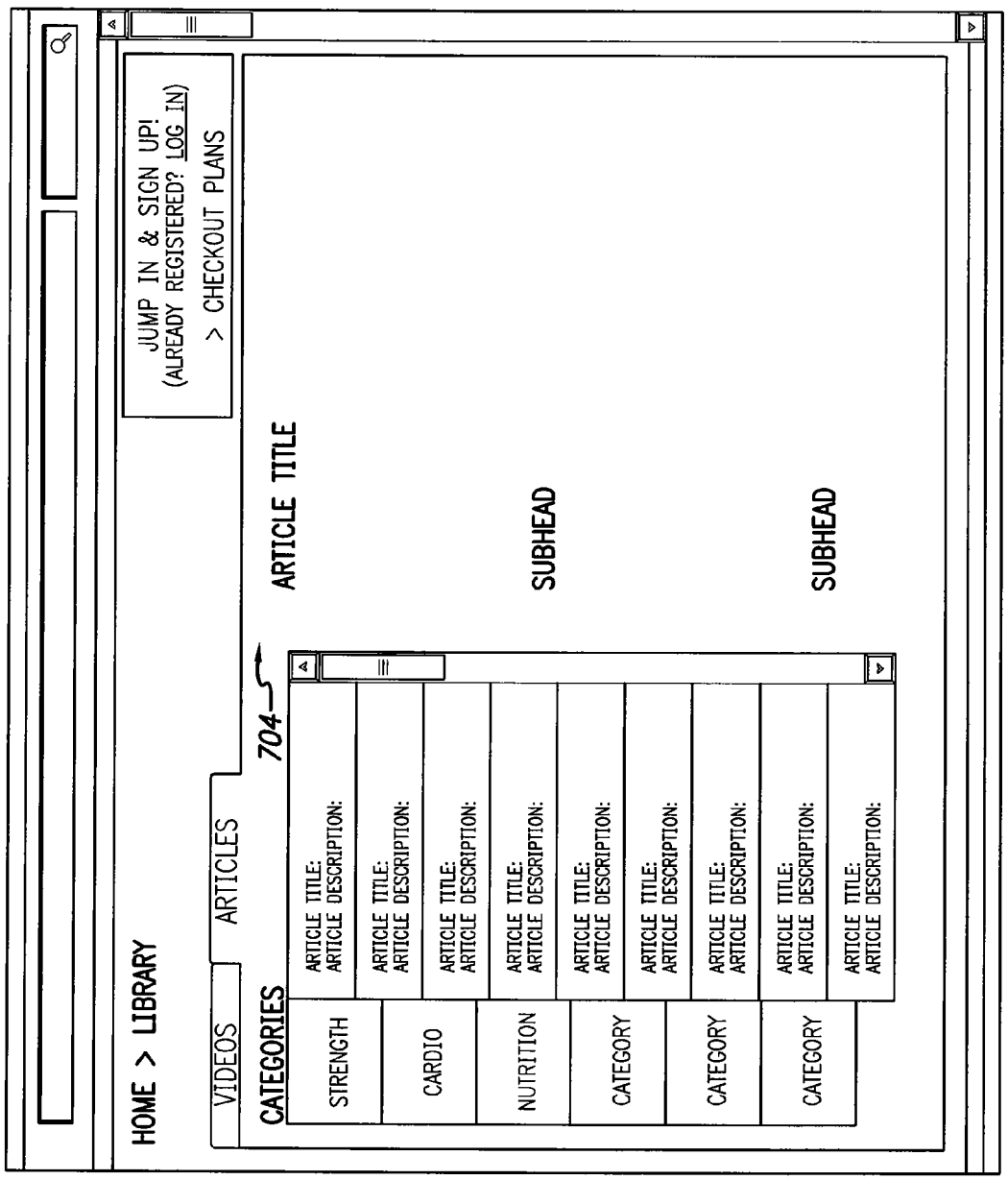
FIG. 46 is an exemplary GUI window according to an embodiment of the present invention.

FIG. 46 is an exemplary GUI window that may be displayed by the library module 700 for providing articles 704. The library module 700 may include an articles 704 section that provides articles information the user 100 about various health and fitness topics. Articles may focus on topics such as strength training, cardiovascular exercise, biking, running, or a variety of other topics. The articles 704 may not all relate directly to fitness activities. For example, some articles may be related to diet and nutrition.

Figure 47:
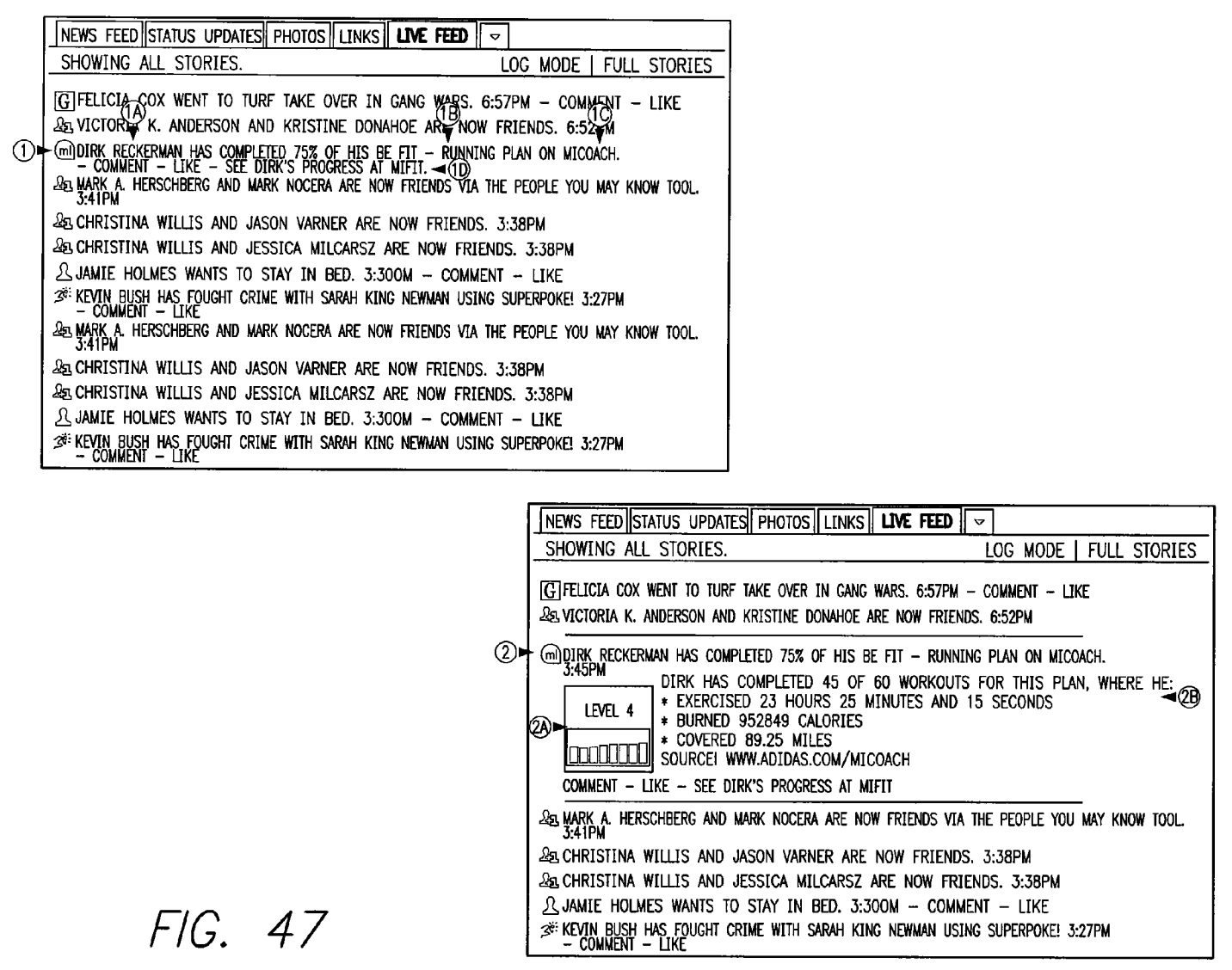

The forum module 800 may be capable of displaying GUI windows for user forums. In one embodiment, as illustrated in FIG. 47, the forum module 800 may employ a social networking application, such as, for example, Facebook. The social networking application may utilize an application programming interface that allows the social networking application, such as Facebook, to be embedded into the GUI windows of the present invention. In another embodiment, the social networking site provides a feed that can be transmitted and displayed via the GUI windows of the present invention.

The forum page may be a place where users 100 can exchange updates regarding their fitness planning and progress using the system of the present invention. Users 100 may also exchange information regarding the website, the particular training equipment and devices they are using, the athletic events or races they are participating in, and information giving and/or requesting coaching or other advice.

Various aspects of the present invention, or any parts or functions thereof, may be implemented using hardware, software, firmware, tangible computer readable or computer usable storage media having instructions stored thereon, or a combination thereof and may be implemented in one or more computer systems or other processing systems.

Program products, methods, and systems for providing fitness monitoring services of the present invention can include any software application executed by one or more computing devices. A computing device can be any type of computing device having one or more processors. For example, a computing device can be a workstation, mobile device (e.g., a mobile phone, personal digital assistant, or laptop), computer, server, compute cluster, server farm, game console, set-top box, kiosk, embedded system, a gym machine, a retail system or other device having at least one processor and memory. Embodiments of the present invention may be software executed by a processor, firmware, hardware or any combination thereof in a computing device.

Software of the present invention may be stored on any computer-usable medium. Such software, when executed in one or more data processing device, causes the data processing device to operate as described herein. Embodiments of the invention employ any computer-usable or -readable medium, known now or in the future. Examples of computer-usable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nanotechnological storage devices, etc.), and communication mediums (e.g., wired and wireless communications networks, local area networks, wide area networks, intranets, etc.).

While many of the exemplary embodiments discussed above make reference to a color-coded heart rate zone-based system, color-coded zone systems based on zones of other parameters including, but not limited to, speed, pace, stride rate, calories, respiration rate, blood oxygen level, blood flow, hydration status, or body temperature may also be employed. The present invention is therefore not to be limited to only heart rate based zone systems.

Furthermore, while many of the exemplary embodiments discussed above make reference to a color-coded heart rate zone-based system where the zones may be defined as ranges of percentages of an athlete's 100 maximum heart rate, heart rate zones may be defined based on other parameters as well.

In one embodiment, heart rate zones may be defined as ranges of percentages of an athlete's 100 maximum heart rate. In another embodiment, heart rate zones may be defined as ranges derived from parameters such as an athlete's 100 ventilation threshold heart rate. In a further embodiment, heart rate zones may be defined as ranges derived from both the athlete's 100 peak heart rate and the athlete's 100 ventilation threshold heart rate.

An athlete's 100 peak heart rate may or may not be the same as the athlete's 100 maximum heart rate. As used herein, "peak heart rate" refers to the highest heart rate that a particular athlete 100 can achieve during a training session. The athlete's physiologically possible maximum heart rate may be higher that the peak heart rate. For some athletes 100, typically those in top physical condition, their peak heart rate may be very close to their max heart rate. For other athletes 100, typically those who are less well conditioned, their peak heart rate may be far less than their true physiologically possible max heart rate. Accordingly, in an embodiment, an athlete 100 may enter their peak heart rate into their portable fitness monitoring device 102 or save this information on the server 112. The athlete 100 may also be able to capture peak heart rate information during an assessment run, as described in further detail above.

As an exercise progressively increases in intensity, the air into and out of your respiratory tract (called ventilation) increases linearly or similarly. As the intensity of exercise continues to increase, there becomes a point at which ventilation starts to increase in a non-linear fashion. This point where ventilation deviates from the progressive linear increase is called the "ventilation threshold." The ventilation threshold is closely related to the lactate threshold, or the point during intense exercise at which there is an abrupt increase in blood lactate levels. Research suggests that the ventilation and lactate thresholds may be some of the best and most consistent predictors of performance in endurance events. The athlete's 100 heart rate at the ventilation threshold point may be referred to as their ventilation threshold heart rate. Accordingly, in an embodiment, an athlete 100 may enter their ventilation threshold heart rate into their portable fitness monitoring device 102 or save this information on the server 112. The athlete 100 may also be able to capture ventilation threshold heart rate information during an assessment run, as described in further detail above, by using equipment necessary for determining ventilation and/or lactate threshold.

In an embodiment, the heart rate zones may be defined as ranges derived from both the athlete's 100 peak heart rate and the athlete's 100 ventilation threshold heart rate. For example, Table 1 illustrates an exemplary embodiment in which color-coded heart rate zones may be defined for an athlete 100 with a peak heart rate (PHR) of 200 beats per minute and a ventilation threshold heart rate (VTHR) of 170 beats per minute:

TABLE 1

| ZONE BOUNDARY | CALCULATION | HR VALUE | % MAX HR |
|---|---|---|---|
| Upper Red Zone Limit (URZ) | =PHR | 200 | 93.5% |
| Lower Red Zone Limit (LRZ) | =%110 of VTHR | 187 | 87.4% |
| Upper Yellow Zone Limit (UYZ) | =LRZ − 1 | 186 | 87.0% |
| Lower Yellow Zone Limit (LYZ) | =VTHR | 170 | 79.5% |
| Upper Green Zone Limit (UGZ) | =LYZ − 1 | 169 | 79.0% |
| Lower Green Zone Limit (LGZ) | =UBZ + 1 | 154 | 72.0% |
| Upper Blue Zone Limit (UBZ) | =90% of VTHR | 153 | 71.5% |
| Lower Blue Zone Limit (LBZ) | =80% of VTHR | 135 | 63.1% |

As illustrated by Table 1, each color coded zone may be defined as having upper and lower limits. Each zone limit may be calculated based on PHR, VTHR, and/or one of the other zone limits. A heart rate value associated with each zone limit may be correlated to a percentage of max heart rate if max heart rate is known or can be estimated. In an embodiment, PHR is assumed to be 93.5% of an athlete's 100 max heart rate value. Accordingly, physical activities may be carried out and content may be presented via GUIs according to the color-coded heart rate zone based system of the present invention.

As described above, color-coded pace or speed based systems may also be employed. In an embodiment, upper and lower pace or speed zone limits may be derived in part from PHR and VTHR values. For example, an athlete may conduct one or more physical activities using a heart rate monitor, a ventilation threshold (or lactate threshold) monitor, and/or pace or speed monitors. Measurements may be conducted by portable monitors, stationary monitors, or in a laboratory after the physical activities are conducted. A relationship between the pace or speed of the athlete and max heart rate, PHR, and/or VTHR may be established. Accordingly, color-coded pace or speed zone limits may be determined based on this information.

In another embodiment of the present invention, zones may be determined based on a measurement of power. Power measurements may be derived from pace calculations if other parameters such as, for example, the athlete's 100 body weight and the incline of the surface traversed (e.g. incline of a sidewalk, bike path, or treadmill surface).

In an embodiment, the athlete 100 may be able to download mobile applications to a mobile device such as a mobile phone, that are capable of presenting GUIs similar to those illustrated herein, from server 112. Accordingly, the athlete 100 may be able to interact with the server 112, access their account, and perform many of the other planning, tracking, and other functions described herein from a mobile device.

The present invention has been described above by way of exemplary embodiments. Accordingly, the present invention should not be limited by any of the above-described exemplary embodiments, but should be defined only in accordance with the following claims and their equivalences.

What is claimed is:

1. A tangible computer program product comprising a computer readable medium having computer program logic recorded thereon for causing at least one processor to:

graphically display a background comprising a plurality of color coded zones, wherein the plurality of color coded zones are associated with numerical ranges of a first performance parameter;

graphically display information about the first performance parameter to a user regarding the user's performance during a workout, wherein said first performance parameter information is displayed as a function of an interval parameter and overlaid on top of the color coded zone background; and graphically display second performance parameter information to the user regarding the user's performance during the workout, wherein said second performance parameter information is displayed as a function of the interval parameter, wherein the second performance parameter information is overlaid on top of the color coded zone background and the first performance parameter information.

2. The tangible computer program product of claim 1, wherein the interval parameter comprises time.

3. The tangible computer program product of claim 2, wherein first performance parameter information associated with a particular point in time is overlaid on top of the appropriate color coded zone based on a correspondence between a particular numerical value of the first performance parameter at the particular point in time and the numerical range associated with the color coded zone.

4. The tangible computer program product of claim 2, further comprising logic for causing the at least one processor to graphically display a pop-up display element for displaying instantaneous performance data about the first performance parameter at a particular point in time in response to the user indicating a particular point in time of interest.

5. The tangible computer program product of claim 1, wherein the interval parameter comprises distance.

6. The tangible computer program product of claim 5, wherein first performance parameter information associated with a particular distance is overlaid on top of the appropriate color coded zone based on a correspondence between a particular numerical value of the first performance parameter at the particular distance and the numerical range associated with the color coded zone.

7. The tangible computer program product of claim 5, further comprising logic for causing the at least one processor to graphically display a pop-up display element for displaying instantaneous performance data about the first performance parameter at a particular distance in response to the user indicating a particular distance of interest.

8. The tangible computer program product of claim 1, wherein the first and second performance parameter information was recorded over a portion of the workout.

9. The tangible computer program product of claim 1, wherein the first performance parameter information comprises heart rate.

10. The tangible computer program product of claim 9, wherein the second performance parameter information comprises pace.

11. The tangible computer program product of claim 9, wherein the second performance parameter information comprises speed.

12. The tangible computer program product of claim 1, wherein the first performance parameter information and the second performance parameter information are selected from the group consisting of: heart rate information and pace information.

13. The tangible computer program product of claim 1, further comprising logic for causing the at least one processor to graphically display an average line denoting the average value for the first performance parameter during the workout, wherein the average line is overlaid on top of the color coded zone background and the first performance parameter information.

14. A tangible computer program product comprising a computer readable medium having computer program logic recorded thereon for causing at least one processor to:
  graphically display performance parameter information to a user regarding the user's performance during a workout, wherein said performance parameter information is displayed as a function of an interval parameter;
  provide first and second analysis boundary markers capable of being manipulated by the user to define a subset of said graphically displayed performance parameter information; and
  in response to the user manipulation, display numerical performance parameter information corresponding to only the subset of graphically displayed performance parameter information defined by the analysis boundary markers.

15. The tangible computer program product of claim 14, wherein the interval parameter comprises time.

16. The tangible computer program product of claim 15, further comprising logic for causing the at least one processor to graphically display a pop-up display element for displaying instantaneous performance data about the performance parameter at a particular point in time in response to the user indicating a particular point in time of interest.

17. The tangible computer program product of claim 14, wherein the interval parameter comprises distance.

18. The tangible computer program product of claim 17, further comprising logic for causing the at least one processor to graphically display a pop-up display element for displaying instantaneous performance data about the performance parameter at a particular distance in response to the user indicating a particular distance of interest.

19. The tangible computer program product of claim 14, wherein the performance parameter information is selected from the group consisting of: heart rate information and pace information.

20. The tangible computer program product of claim 14, wherein the performance parameter information is overlaid on top of a color coded zone background.

21. The tangible computer program product of claim 14, further comprising logic for causing the at least one processor to graphically display an average line denoting the average value for the performance parameter during the workout, wherein the average line is overlaid on top of the performance parameter information.

22. The tangible computer program product of claim 14, further comprising logic for causing the at least one processor to, in response to the user manipulation of a graphical user interface element, disable use of the first and second analysis boundary markers.

23. The tangible computer program product of claim 14, wherein the numerical performance parameter information corresponding to only the subset of graphically displayed performance parameter information defined by the analysis boundary markers that is displayed is average numerical performance parameter information.

24. The tangible computer program product of claim 14, wherein the numerical performance parameter information corresponding to only the subset of graphically displayed performance parameter information defined by the analysis boundary markers that is displayed is summed numerical performance parameter information.

* * * * *